(12) United States Patent
Molnar et al.

(10) Patent No.: US 8,538,513 B2
(45) Date of Patent: Sep. 17, 2013

(54) STIMULATION ELECTRODE SELECTION

(75) Inventors: Gabriela C. Molnar, Fridley, MN (US); Jianping Wu, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 696 days.

(21) Appl. No.: 12/639,678

(22) Filed: Dec. 16, 2009

(65) Prior Publication Data

US 2011/0144521 A1 Jun. 16, 2011

(51) Int. Cl.
*A61B 5/04* (2006.01)

(52) U.S. Cl.
USPC .............................. 600/544; 607/45; 607/46

(58) Field of Classification Search
USPC .............................. 600/544, 545; 607/45, 46
See application file for complete search history.

(56) References Cited

U.S. PATENT DOCUMENTS

| | | | |
|---|---|---|---|
| 6,066,163 A | 5/2000 | John | |
| 7,519,431 B2 | 4/2009 | Goetz et al. | |
| 7,983,757 B2 * | 7/2011 | Miyazawa et al. | 607/45 |
| 2006/0217781 A1 | 9/2006 | John | |
| 2007/0129770 A1 | 6/2007 | Younis | |
| 2007/0203546 A1 | 8/2007 | Stone et al. | |
| 2007/0225674 A1 | 9/2007 | Molnar et al. | |
| 2007/0265489 A1 * | 11/2007 | Fowler et al. | 600/12 |
| 2008/0004675 A1 * | 1/2008 | King et al. | 607/59 |
| 2008/0183256 A1 * | 7/2008 | Keacher | 607/116 |
| 2008/0269836 A1 | 10/2008 | Foffani et al. | |
| 2009/0082691 A1 | 3/2009 | Denison et al. | |
| 2009/0099627 A1 | 4/2009 | Molnar et al. | |
| 2009/0192556 A1 | 7/2009 | Wu et al. | |
| 2009/0228070 A1 | 9/2009 | Goetz et al. | |
| 2009/0234422 A1 | 9/2009 | Goetz et al. | |
| 2010/0100153 A1 | 4/2010 | Carlson et al. | |

FOREIGN PATENT DOCUMENTS

| | | |
|---|---|---|
| WO | 0158351 A1 | 8/2001 |
| WO | WO 2006/110206 A1 | 10/2006 |
| WO | WO 2006/110690 A1 | 10/2006 |
| WO | 2007112061 A2 | 10/2007 |
| WO | 2009055127 A1 | 4/2009 |
| WO | 2009073891 A1 | 6/2009 |
| WO | 2009134475 A1 | 11/2009 |
| WO | 2010044989 A2 | 6/2011 |

OTHER PUBLICATIONS

Jensen et al., "Information, Energy, and Entropy: Design Principles for Adaptive, Therapeutic Modulation of Neural Circuits," European Patent Office, Downloaded on Dec. 22, 2009, from IEEE Xplore (8 pgs.).

(Continued)

*Primary Examiner* — Navin Natnithithadha
*Assistant Examiner* — Etsub Berhanu
(74) *Attorney, Agent, or Firm* — Shumaker & Sieffert, P.A.

(57) ABSTRACT

Bioelectrical signals may be sensed within a brain of a patient with a plurality of sense electrode combinations. A stimulation electrode combination for delivering stimulation to the patient to manage a patient condition can be selected based on a frequency domain characteristic of the sensed bioelectrical signals. In some examples, a stimulation electrode combination is selected based on a determination of which of the sense electrodes are located closest to a target tissue site, as indicated by the one or more sense electrodes that sensed a bioelectrical brain signal with a relatively highest value of the frequency domain characteristic. In some examples, determining which of the sense electrodes are located closest to the target tissue site may include executing an algorithm using relative values of the frequency domain characteristic.

67 Claims, 31 Drawing Sheets

(56) References Cited

OTHER PUBLICATIONS

Chen et al., "Intra-operative recordings of local field potentials can help localize the subthalamic nucleus in Parkinson's disease surgery," Exp Neurol, (2005) (8 pgs.).

Debatisse et al., "DBS in STN and macrorecording using electrodes of stimulation: what can be done and where we are?," http://files.chuv.ch/internet-docs/nch/posters/nch_dbs_in_stn.pdf, (1 pg.).

Wingeier et al. "Intra-operative STN DBS attenuates the prominent beta rhythm in the STN in Parkinson's disease," Experimental Neurology 197 (2006) pp. 244-251.

Kühn et al., "High-Frequency Stimulation of the Subthalamic Nucleus Suppresses Oscillatory β Activity in Patients with Parkinson's Disease in Parallel with Improvement in Motor Performance," Journal of Neuroscience, 28(24), Jun. 11, 2008, pp. 6165-6173.

Marceglia et al., "Basal ganglia local field potentials: applications in the development of new deep brain stimulation devices for movement disorders," Expert Rev. Med. Devices 4(5), (2007) pp. 605-614.

Rossi et al., "Subthalamic local field potential oscillations during ongoing deep brain stimulation in Parkinson's disease," Brain Research Bulletin 76 (2008) pp. 512-521.

U.S. Appl. No. 12/639,717, filed Dec. 16, 2009 entitled "Stimulation Electrode Selection," by Molnar et al.

U.S. Appl. No. 61/105,943, filed Oct. 16, 2008 entitled "Stimulation Electrode Selection," by Carlson et al.

U.S. Appl. No. 12/563,845, filed Sep. 21, 2009 entitled "Stimulation Electrode Selection," by Carlson et al.

International Search Report and Written Opinion for corresponding PCT Application No. PCT/US2010/059624, dated Mar. 3, 2011 (11 pgs.).

Office Action dated May 21, 2012 for U.S. Appl. No. 12/639,717 (10 pgs.).

Responsive Amendment dated Aug. 21, 2012 for U.S. Appl. No. 12/639,717, (27 pgs.).

Response to Office Action dated Sep. 28, 2012, from U.S. Appl. No. 12/639,717, filed Dec. 28, 2012, 28 pp.

Office Action from U.S. Appl. No. 12/639,717, dated Sep. 28, 2012, 9 pp.

Office Action for U.S. Appl. No. 12/639,717, dated Feb. 1, 2013, 5 pp.

Requirement for Election of Species for U.S. Appl. No. 12/768,403, dated Feb. 20, 2013, 6 pp.

Response to Office Action dated Feb. 1, 2013, from U.S. Appl. No. 12/639,717, filed Mar. 26, 2013, 3 pp.

Notice of Allowance for U.S. Appl. No. 12/639,717, mailed Apr. 22, 2013, 8 pp.

Response to Election of Species Requirement dated Feb. 20, 2013, from U.S. Appl. No. 12/768,403, filed Mar. 22, 2013, 4 pp.

* cited by examiner

STIMULATION ELECTRODE SELECTION

TECHNICAL FIELD

The disclosure relates to selection of sense and stimulation electrodes.

BACKGROUND

Implantable medical devices, such as electrical stimulators, may be used in different therapeutic applications. In some therapy systems, an implantable electrical stimulator delivers electrical therapy to a target tissue site within a patient with the aid of one or more medical leads that include electrodes. In addition to or instead of electrical stimulation therapy, a medical device may deliver a therapeutic agent to a target tissue site within a patient with the aid of one or more fluid delivery elements, such as a catheter.

During a programming session, which may occur during implant of the medical device, during a trial session, or during a follow-up session after the medical device is implanted in the patient, a clinician may generate one or more therapy programs that provide efficacious therapy to the patient, where each therapy program may define values for a set of therapy parameters. A medical device may deliver therapy to a patient according to one or more stored therapy programs. In the case of electrical stimulation, the therapy parameters may include the configuration of electrodes used to deliver the electrical stimulation therapy.

SUMMARY

In general, the disclosure is directed toward selecting one or more electrodes from a plurality of electrodes for delivering electrical stimulation therapy to a brain of a patient. The one or more selected electrodes used to deliver stimulation may be referred to as a stimulation electrode combination, and may include a first electrode positioned on a lead and a reference electrode positioned relatively far from the first electrode (e.g., unipolar stimulation) or two or more electrodes positioned on a lead (e.g., bipolar stimulation). In examples described herein, the stimulation electrode combination may be selected based on bioelectrical signals sensed within the patient's brain. In particular, bioelectrical signals may be sensed within the brain with a plurality of sense electrode combinations, and the stimulation electrode combination may be selected based on one or more frequency domain characteristics of the sensed signals. For example, the stimulation electrode combination may be selected by at least determining a frequency domain characteristic (e.g., an energy level within a particular frequency band) for each bioelectrical brain signal of a plurality of bioelectrical brain signals sensed via at least one respective electrode, and comparing the frequency domain characteristics. In some cases, a stimulation electrode combination is selected based on the one or more electrodes used to sense the bioelectrical brain signal that has the relatively highest energy level within a particular frequency band. However, other relative frequency domain characteristics can be used to select the stimulation electrode combination, such as the relatively lowest energy level within a particular frequency band.

In one example, the disclosure is directed to a method comprising determining a frequency domain characteristic for each bioelectrical brain signal of a plurality of bioelectrical signals sensed in a brain of a patient with a respective electrode, determining a plurality of relative values of the frequency domain characteristic, wherein each of the plurality of relative values is based on at least two of the frequency domain characteristics, and selecting at least one of the electrodes for delivering stimulation to the patient based on the plurality of relative values.

In another example, the disclosure is directed to a method comprising sensing a first group of bioelectrical signals in a brain of a patient with a first group of electrodes, sensing a second group of bioelectrical signals in the brain of the patient with a second group of electrodes, sensing a third group of bioelectrical signals in the brain of the patient with a third group of electrodes, sensing a fourth group of bioelectrical signals in the brain of the patient with a fourth group of electrodes, determining a frequency domain characteristic for each of the bioelectrical signals within each of the first, second, third, and fourth groups of bioelectrical signals, determining a first relative value of the frequency domain characteristic based on the frequency domain characteristics of the first and second groups of bioelectrical signals, determining a second relative value of the frequency domain characteristic based on the frequency domain characteristics of the second and third groups of bioelectrical signals, determining a third relative value of the frequency domain characteristic based on the frequency domain characteristics of the third and fourth groups of bioelectrical signals, determining a fourth relative value of the frequency domain characteristic based on the frequency domain characteristics of the first and fourth groups of bioelectrical signals, and selecting at least one of the first, second, third, or fourth groups of electrodes for delivering stimulation to a target tissue site of the patient based on the first, second, third, and fourth relative values.

In another aspect, the disclosure is directed to a system comprising a plurality of electrodes, a sensing module that senses a plurality of bioelectrical brain signals via at least one respective electrode of the plurality of electrodes, and a processor that determines a frequency domain characteristic for each of the plurality of bioelectrical signals, determines a plurality of relative values of the frequency domain characteristic, wherein each of the plurality of relative values is based on at least two of the frequency domain characteristics, and selects at least one of the plurality of electrodes for delivering stimulation to the patient based on the plurality of relative values In another aspect, the disclosure is directed to a system comprising a plurality of electrodes, a sensing module that senses a first group of bioelectrical signals in a brain of a patient via a first group of electrodes comprising at least one electrode from the plurality of electrodes, a second group of bioelectrical signals in the brain of the patient via a second group of electrodes comprising at least one electrode from the plurality of electrodes, a third group of bioelectrical signals in the brain of the patient via a third group of electrodes comprising at least one electrode from the plurality of electrodes, and a fourth group of bioelectrical signals in the brain of the patient via a fourth group of electrodes comprising at least one electrode from the plurality of electrodes, and a processor. The processor determines a frequency domain characteristic for each of the bioelectrical signals within each of the first, second, third, and fourth groups of bioelectrical signals, determines a first relative value of the frequency domain characteristic based on the frequency domain characteristics for the first and second groups of bioelectrical signals, determines a second relative value of the frequency domain characteristic based on the frequency domain characteristics for the second and third groups of bioelectrical signals, determines a third relative value of the frequency domain characteristic based on the frequency domain characteristics for the third and fourth groups of bioelectrical signals, determines a fourth relative value of the frequency domain characteristic based on the frequency domain characteristics for the first and fourth groups of bioelectrical signals, and selects at least one of the first, second, third, or fourth groups of electrodes for delivering stimulation to a target tissue site of the patient based on the first, second, third, and fourth relative values.

In another aspect, the disclosure is directed to a system comprising means for sensing a plurality of bioelectrical brain signals via respective electrodes, means for determining a frequency domain characteristic for each of the plurality of bioelectrical signals, means for determining a plurality of relative values of the frequency domain characteristics, wherein each of the plurality of relative values is based on at least two of the frequency domain characteristics, and means for selecting at least one of the plurality of electrodes for delivering stimulation to the patient based on the plurality of relative values.

In another aspect, the disclosure is directed to a system comprising means for sensing a first group of bioelectrical signals in a brain of a patient via a first group of electrodes comprising at least one electrode from the plurality of electrodes, a second group of bioelectrical signals in the brain of the patient via a second group of electrodes comprising at least one electrode from the plurality of electrodes, a third group of bioelectrical signals in the brain of the patient via a third group of electrodes comprising at least one electrode from the plurality of electrodes, and a fourth group of bioelectrical signals in the brain of the patient via a fourth group of electrodes comprising at least one electrode from the plurality of electrodes, means for determining a frequency domain characteristic for each of the bioelectrical signals within each of the first, second, third, and fourth groups of bioelectrical signals, means for determining a first relative value of the frequency domain characteristic based on the frequency domain characteristics for the first and second groups of bioelectrical signals, a second relative value of the frequency domain characteristic based on the frequency domain characteristics for the second and third groups of bioelectrical signals, a third relative value of the frequency domain characteristic based on the frequency domain characteristics for the third and fourth groups of bioelectrical signals, a fourth relative value of the frequency domain characteristic based on the frequency domain characteristics for the first and fourth groups of bioelectrical signals, and means for selecting at least one of the first, second, third, or fourth groups of electrodes for delivering stimulation to a target tissue site of the patient based on the first, second, third, and fourth relative values.

In another aspect, the disclosure is directed to a computer-readable storage medium comprising instructions. The instructions cause a programmable processor to determine a frequency domain characteristic for each of a plurality of bioelectrical signals sensed in a brain of a patient with respective electrodes, determine a plurality of relative values of the frequency domain characteristic, wherein each of the plurality of relative values is based on at least two of the frequency domain characteristics, and select at least one of the electrodes for delivering stimulation to the patient based on the plurality of relative values.

In another aspect, the disclosure is directed to a computer-readable storage medium comprising instructions. The instructions cause a programmable processor to determine a frequency domain characteristic each bioelectrical brain signal of a first group of bioelectrical signals in a brain of a patient with a first group of electrodes, a second group of bioelectrical signals in the brain of the patient with a second group of electrodes, a third group of bioelectrical signals in the brain of the patient with a third group of electrodes, and a fourth group of bioelectrical signals in the brain of the patient with a fourth group of electrodes, determine a first relative value of the frequency domain characteristic based on the frequency domain characteristics for the first and second groups of bioelectrical signals, determine a second relative value of the frequency domain characteristic based on the frequency domain characteristics for the second and third groups of bioelectrical signals, determine a third relative value of the frequency domain characteristic based on the frequency domain characteristics for the third and fourth groups of bioelectrical signals, determine a fourth relative value of the frequency domain characteristic based on the frequency domain characteristics for the first and fourth groups of bioelectrical signals; and select at least one of the first, second, third, or fourth groups of electrodes for delivering stimulation to a target tissue site of the patient based on the first, second, third, and fourth relative values.

In another aspect, the disclosure is directed to a computer-readable storage medium comprising instructions. The instructions cause a programmable processor to perform any part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, random access memory or RAM) or any other type of volatile or non-volatile memory that stores instructions (e.g., in the form of a computer program or other executable) to cause a programmable processor to perform the techniques described herein.

The details of one or more embodiments of the disclosure are set forth in the accompanying drawings and the description below. Other features, objects, and advantages of the disclosure will be apparent from the description and drawings, and from the claims.

DETAILED DESCRIPTION

Figure 1:
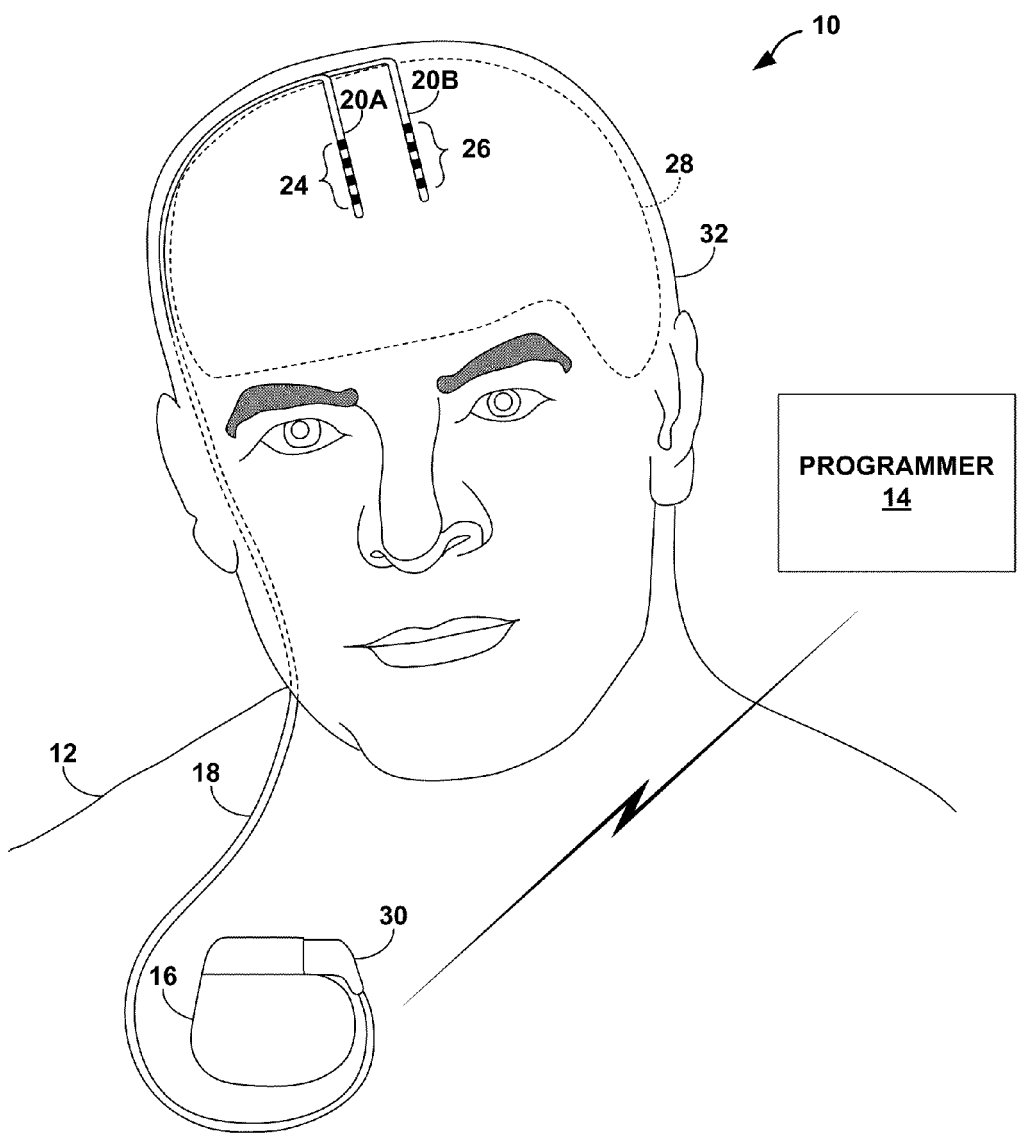
FIG. 1 is a conceptual diagram illustrating an example deep brain stimulation (DBS) system.

FIG. 1 is a conceptual diagram illustrating an example therapy system 10 that delivers therapy to control a patient condition, such as a movement disorder, neurodegenerative impairment, a mood disorder or a seizure disorder of patient 12. Patient 12 ordinarily will be a human patient. In some cases, however, therapy system 10 may be applied to other mammalian or non-mammalian, non-human patients. While movement disorders and neurodegenerative impairment are primarily referred to herein, in other examples, therapy system 10 may provide therapy to manage symptoms of other patient conditions, such as, but not limited to, seizure disorders (e.g., epilepsy) or mood (or psychological) disorders (e.g., major depressive disorder (MDD), bipolar disorder, anxiety disorders, post traumatic stress disorder, dysthymic disorder, and obsessive-compulsive disorder (OCD)).

A movement disorder or other neurodegenerative impairment may include symptoms such as, for example, muscle control impairment, motion impairment or other movement problems, such as rigidity, bradykinesia, rhythmic hyperkinesia, nonrhythmic hyperkinesia, and akinesia. In some cases, the movement disorder may be a symptom of Parkinson's disease. However, the movement disorder may be attributable to other patient conditions. Although movement disorders are primarily referred to throughout the remainder of the disclosure, the therapy systems and methods described herein are also useful for managing (e.g., controlling patient symptoms) other patient conditions, such as neurodegenerative impairment or mood disorders.

Therapy system 10 includes medical device programmer 14, implantable medical device (IMD) 16, lead extension 18, and leads 20A and 20B with respective sets of electrodes 24, 26. In the example shown in FIG. 1, electrodes 24, 26 of leads 20A, 20B are positioned to deliver electrical stimulation to a tissue site within brain 28, such as a deep brain site under the dura mater of brain 28 of patient 12. In some examples, delivery of stimulation to one or more regions of brain 28, such as the subthalamic nucleus, globus pallidus or thalamus, may be an effective treatment to manage movement disorders, such as Parkinson's disease. Electrodes 24, 26 are also positioned to sense bioelectrical brain signals within brain 28 of patient 12. In some examples, some of electrodes 24, 26 may be configured to sense bioelectrical brain signals and others of electrodes 24, 26 may be configured to deliver electrical stimulation to brain 28. In other examples, all of electrodes 24, 26 are configured to both sense bioelectrical brain signals and deliver electrical stimulation to brain 28.

IMD 16 includes a therapy module that includes a stimulation generator that generates and delivers electrical stimulation therapy to patient 12 via a subset of electrodes 24, 26 of leads 20A and 20B, respectively. The subset of electrodes 24, 26 that are used to deliver electrical stimulation to patient 12, and, in some cases, the polarity of the subset of electrodes 24, 26, may be referred to as a stimulation electrode combination. As described in further detail below, the stimulation electrode combination can be selected for a particular patient 12 and target tissue site (e.g., selected based on the patient condition) based on one or more frequency domain characteristics of a bioelectrical brain signal that is sensed by one or more groups of electrodes 24, 26 that are associated with the stimulation electrode combination. The group of electrodes 24, 26 includes at least one electrode and can include a plurality of electrodes. In some examples, the bioelectrical signals sensed within brain 28 may reflect changes in electrical current produced by the sum of electrical potential differences across brain tissue. Examples of bioelectrical brain signals include, but are not limited to, electrical signals generated from local field potentials (LFP) sensed within one or more regions of brain 28, such as an electroencephalogram (EEG) signal, or an electrocorticogram (ECoG) signal. Local field potentials, however, may include a broader genus of electrical signals within brain 28 of patient 12.

In some examples, the bioelectrical brain signals that are used to select a stimulation electrode combination may be sensed within the same region of brain 28 as the target tissue site for the electrical stimulation. As previously indicated, these tissue sites may include tissue sites within the thalamus, subthalamic nucleus or globus pallidus of brain 28, as well as other target tissue sites. The specific target tissue sites and/or regions within brain 28 may be selected based on the patient condition. Thus, in some examples, both a stimulation electrode combination and sense electrode combinations may be selected from the same set of electrodes 24, 26. In other examples, the electrodes used for delivering electrical stimulation may be different than the electrodes used for sensing bioelectrical brain signals.

In some examples, the stimulation electrode combination may be selected during a programming session following the implantation of IMD 16 and leads 20A, 20B in patient 12. For example, during the programming session, bioelectrical brain signals may be sensed within brain 28 via one or more of electrodes 24, 26. Each sense electrode combination may include a different subset of one or more electrodes 24, 26. Frequency domain characteristics of each of the sensed bioelectrical brain signals may be compared to each other and one or more stimulation electrode combinations may be selected based on the comparison. An example of a frequency domain characteristic may include power level (or energy level) within a particular frequency band. The power level may be determined based on, for example, a spectral analysis of a bioelectrical brain signal. The spectral analysis may indicate the distribution over frequency of the power contained in a signal, based on a finite set of data.

In some examples, a stimulation electrode combination can be selected based on the one or more electrodes with which the bioelectrical brain signal with the highest relative band power (or energy) level in a selected frequency band was sensed. This may indicate, for example, that the one or more electrodes with which the bioelectrical brain signal with the highest relative band power level was sensed is located closest to the target tissue site, which can be a region within brain 28 that produces a bioelectrical signal with the highest relative power level within a selected frequency band. The particular frequency band of interest is selected based on the patient condition. For example, it is believed that abnormal activity within a beta band (e.g., about 8 hertz (Hz) to about 30 Hz or about 16 Hz to about 30 Hz) of a bioelectrical brain signal is indicative of brain activity associated with a movement disorder (e.g., Parkinson's disease), as well as revealing of a target tissue site for therapy delivery to manage the patient condition. Therefore, in some examples, the power level within a beta band of a bioelectrical brain signal can be used to identify a target tissue site for stimulation therapy to manage a movement disorder.

In other examples, depending on the patient condition, electrical activity within a gamma band (e.g., about 35 Hz to about 120 Hz) of a bioelectrical brain signal may be revealing of a target tissue site. For example, a target tissue site, e.g., the subthalamic nucleus, within the brain of a patient with Parkinson's disease or another movement disorder may exhibit bioelectrical brain signals with high gamma band activity when the patient is treated with medication or when the patient moves. Therefore, in some examples, the power level within a gamma band of a bioelectrical brain signal can be used to identify a target tissue site.

Some algorithms described herein help identify the location of a target tissue site in a direction substantially along a longitudinal axis of one or both leads 20. That is, some algorithms described herein help identify which electrode 24, 26 along the respective lead 20 is closest to the target tissue site, whereby each of the electrodes 24 is displaced from an adjacent electrode in an axial direction along the longitudinal axis of lead 20A, and each of the electrodes 26 is displaced from an adjacent electrode in an axial direction along the longitudinal axis of lead 20B. In addition, in some examples, some algorithms described herein help identify the location of a target tissue site in a direction other than a direction indicated by the longitudinal axis of one or both leads 20. For example, algorithms described herein help identify the location of a target tissue site in a direction indicated by each of a plurality of segmented or partial ring electrodes that share an axial position along a longitudinal axis of one or both leads 20, but have different radial positions (e.g., a direction substantially perpendicular to the longitudinal axis of one or both leads 20). When both types of algorithms are combined, such that the location of a target tissue site is determined in two directions, the combined algorithm can be referred to as a three-dimensional (3D) algorithm, which can be used to locate a relative target tissue site in three dimensions.

In some cases, the target tissue site for therapy delivery may be located between two sense electrodes. If the target tissue site is located directly between two sense electrodes, determining which of the sense electrodes is closest to the target tissue site may require a more complex technique than simply determining the electrode or electrodes that sensed the bioelectrical signal with the highest relative power level within the selected frequency band. In examples described herein, an algorithm that determines whether the target tissue site is located between sensed electrodes may be applied to determine the electrode or electrodes that are located closest to a target tissue site.

In some examples, the algorithm includes sensing a plurality of bioelectrical brain signals and determining the relative beta band power levels. The relative beta band power may be a ratio of the power in a beta band of the sensed signal to the overall power of the sensed signal. The relative beta band power may be used instead of the beta band power in order to normalize the bioelectrical signals sensed by sense electrodes located in different regions of a patient's brain. This normalization of sensed brain signals applies to the power level within any selected frequency band. Thus, while "power levels" within a selected frequency band of a sensed brain signal are generally referred to herein, the power level may be a relative power level, which is a ratio of a power level in a selected frequency band of a sensed brain signal to the overall power of the sensed brain signal.

The power level in the selected frequency band may be determined using any suitable technique. In some examples, a processor of IMD 16 may average the power level of the selected frequency band of a sensed brain signal over a predetermined time period, such as about ten seconds to about two minutes, although other time ranges are also contemplated. In other examples, the selected frequency band power level may be a median power level over a predetermined range of time, such as about ten seconds to about two minutes. The activity within the selected frequency band of a brain signal, as well as other frequency bands of interest, may fluctuate over time. Thus, the power level in the selected frequency band at one instant in time may not provide an accurate and precise indication of the energy of the brain signal in the selected frequency band. Averaging or otherwise monitoring the power level in the selected frequency band over time may help capture a range of power levels, and, therefore, a better indication of the patient's pathological state in the particular brain region sensed by IMD 16.

The overall power of a sensed bioelectrical brain signal may be determined using any suitable technique. In one example, a processor of IMD 16 (or another device, such as programmer 14) may determine an overall power level of a sensed bioelectrical brain signal based on the total power level of a swept spectrum of the brain signal. To generate the swept spectrum, the processor may control a sensing module to tune to consecutive frequency bands over time, and the processor may assemble a pseudo-spectrogram of the sensed bioelectrical brain signal based on the power level in each of the extracted frequency bands. The pseudo-spectrogram may be indicative of the energy of the frequency content of the bioelectrical brain signal within a particular window of time.

The algorithm further includes determining a plurality of relative values of the relative beta band power level, where each relative value is based on the relative beta band power levels of two bioelectrical signals sensed by two different electrodes, and selecting the sense electrode or electrodes that are closest to the target tissue site based on the plurality of relative values. The selected electrode or electrodes may be associated with one or more stimulation electrode combinations, which may be programmed into IMD 16 for the delivery of stimulation therapy to brain 28. In this way, the stimulation electrode combination may be selected based on a frequency domain characteristic of a bioelectrical brain signal.

In some examples, other stimulation parameter values may be selected based on the frequency domain characteristics of a bioelectrical brain signal sensed via one or more groups of sense electrodes associated with a stimulation electrode combination. For example, a beta band power level may be associated with a stimulation amplitude value that may provide efficacious therapy to patient 12.

For a particular patient condition, one or more specific frequency bands may be more revealing of a useful target tissue site for providing stimulation therapy to patient 12 than other frequency bands. Processor 40 (shown in FIG. 3) of IMD 16 may perform a spectral analysis of the bioelectrical brain signal in the revealing frequency bands. The spectral analysis of a bioelectrical signal may indicate the power level of each bioelectrical signal within each given frequency band over a range of frequencies. While the beta frequency band is primarily referred to herein, in other examples, processor 40 may select a stimulation electrode combination based on the power level within one or more frequency bands other than the beta band. For example, processor 40 may compare the power levels of a frequency band other than the beta band in bioelectrical signals sensed by different electrodes to determine relative values of the power levels for combinations of electrodes. Processor 40 may then determine which of the electrodes is closest to a target tissue site based on the relative values. In some examples, the beta band includes a frequency range of about 10 Hertz (Hz) to about 35 Hz, such as about 10 Hz to about 30 Hz or 13 Hz to about 30 Hz.

Different frequency bands are associated with different activity in brain 28. It is believed that some frequency band components of a biosignal from within brain 28 may be more revealing of particular patient condition and abnormal brain activity associated with the particular patient condition than other frequency components. One example of the frequency bands is shown in Table 1:

TABLE 1

Frequency bands

| Frequency (f) Band Hertz (Hz) | Frequency Information |
|---|---|
| f < 5 Hz | δ (delta frequency band) |
| 5 Hz ≤ f ≤ 10 Hz | α (alpha frequency band) |
| 10 Hz ≤ f ≤ 30 Hz | β (beta frequency band) |
| 50 Hz ≤ f ≤ 100 Hz | γ (gamma frequency band) |
| 100 Hz ≤ f ≤ 200 Hz | high γ (high gamma frequency band) |

The frequency ranges for the frequency bands shown in Table 1 are merely examples. The frequency ranges may differ in other examples. For example, another example of frequency ranges for frequency bands are shown in Table 2:

TABLE 2

Frequency bands

| Frequency (f) Band Hertz (Hz) | Frequency Information |
|---|---|
| f < 5 Hz | δ (delta frequency band) |
| 5 Hz ≤ f ≤ 8 Hz | q (theta frequency band) |
| 8 Hz ≤ f ≤ 12 Hz | α (alpha frequency band) |
| 12 Hz ≤ f ≤ 16 Hz | s (sigma or low beta frequency band) |
| 16 Hz ≤ f ≤ 30 Hz | High β (high beta frequency band) |
| 50 Hz ≤ f ≤ 100 Hz | γ (gamma frequency band) |
| 100 Hz ≤ f ≤ 200 Hz | high γ (high gamma frequency band) |

In one example, a clinician may select the frequency band of a bioelectrical brain signal for selecting stimulation electrode combinations based on information specific to patient 12 or based on data gathered from more than one patient 12. The frequency bands that are useful for identifying a target tissue site for stimulation to manage a patient condition can be specific to a particular patient 12 or general to a group of patients with similar conditions. In some examples, a clinician may utilize medical imaging techniques to identify which portions of brain 28 exhibit abnormal activity when symptoms of the patient condition are observed. For example, the clinician may utilize an imaging device, such as magnetoencephalography (MEG), positron emission tomography (PET) or functional magnetic resonance imaging (fMRI) to identify the region of brain 28 associated that exhibits the greatest detectable change when certain patient symptoms (e.g., a difficulty initiating movement) are observed. In other examples, the clinician can select the target tissue site known to be associated with the patient condition based on, e.g., past knowledge or past studies on subjects with similar patient conditions. In the examples described below, the beta band is used as an example to describe the techniques for selecting stimulation electrode combinations based on a bioelectrical brain signal. However, the techniques described below are applicable to other frequency bands.

Figure 2:
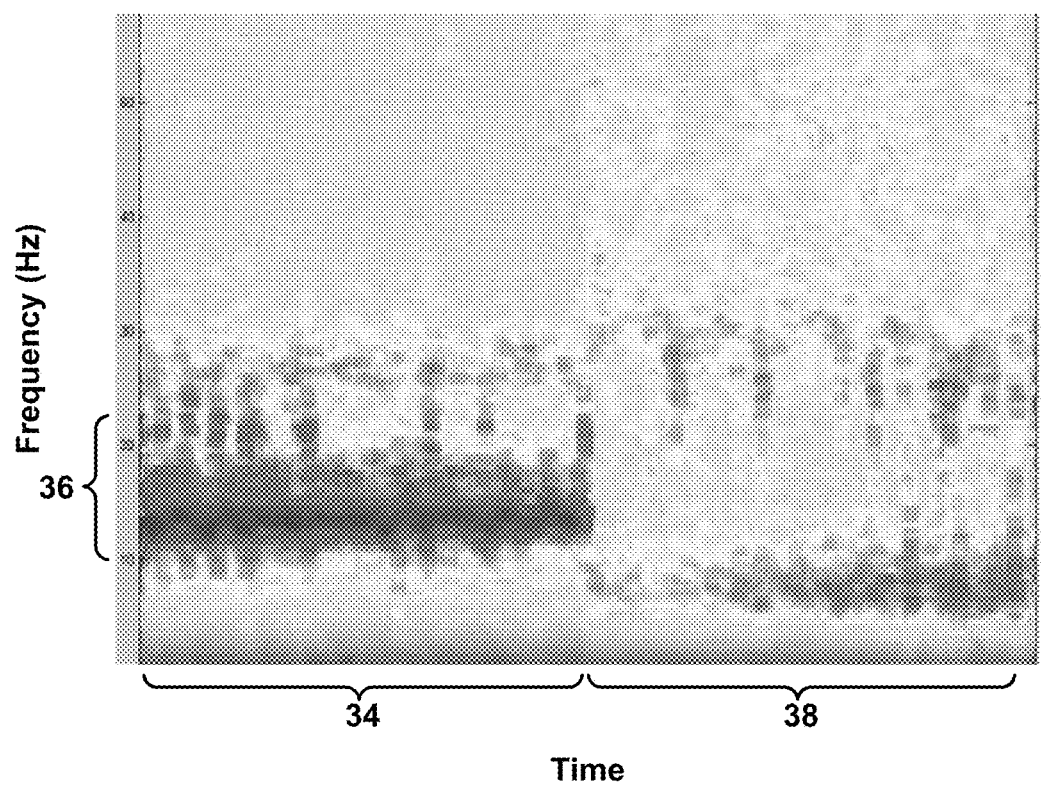
FIG. 2 is an example spectrogram of a bioelectrical brain signal sensed within a brain of a patient.

Some movement disorder symptoms of patient 12, such as bradykinesia, may be associated with abnormal synchronization of beta frequency band activity within particular structures of brain 28 of patient 12. FIG. 2 is an example spectrogram of bioelectrical brain signals sensed within a subthalamic nucleus of a brain of a human subject. The y-axis of the spectrogram indicates the frequency band of the bioelectrical brain signal, the x-axis indicates time, and the z-axis, which extends substantially perpendicular to the plane of the image of FIG. 2, as indicated by the intensity of the spectrogram, indicates a power level of the bioelectrical brain signal. The spectrogram provides a three-dimensional plot of the energy of the frequency content of a bioelectrical brain signal as it changes over time.

In a first time period 34, the human subject is in a pathological state and is not under the influence of therapy to mitigate effects of a movement disorder. As shown in FIG. 2, in the first time period 34, a power level of the bioelectrical brain signal of the human subject in a subset of the beta band 36 is relatively high, as indicated by the relatively intense color in FIG. 2. The subset of the beta band 36 in the example shown in FIG. 2 includes a frequency range of about 10 Hz to about 20 Hz. In a second time period 38, the human subject is under the influence of pharmaceutical agents to mitigate effects of the movement disorder. As shown in FIG. 2, compared to the first time period 34, the beta band activity decreases during the second time period 38 in which the human subject is receiving movement disorder therapy.

The spectrogram shown in FIG. 2 demonstrates that a power level in a beta band of a bioelectrical brain signal may be relatively high in patients suffering from movement disorder symptoms, and the power level may decrease upon the receipt of therapy to manage the movement disorder symptoms. Thus, a high beta band power level may be a marker for a movement disorder. In addition, a tissue site within brain 28 that exhibits a relatively high beta band power level may be an efficacious target tissue site for providing stimulation therapy to patient 12.

In some patients, identifying the location within brain 28 that exhibits the highest relative beta band activity may indicate the location at which electrical stimulation may relatively effectively suppress the abnormal synchronization of beta frequency band activity associated with the patient's movement disorder. The location within brain 28 that demonstrates the highest relative beta band activity may indicate the location within brain 28 that is a suitable stimulation target for electrical stimulation to manage the patient's movement disorder. As a result of directing stimulation to this stimulation target that exhibits a relatively high level of beta band energy, the intensity of stimulation that IMD 16 may deliver in order to provide efficacious stimulation therapy may be lower than the intensity of stimulation that may be required to provide efficacious stimulation therapy to other tissue sites that may be further from the stimulation target or less functionally related to the stimulation target. An intensity of stimulation may be related to the current or voltage amplitude of a stimulation signal, a frequency of the stimulation signal, and, if the signal comprises a pulse, a pulse width, and/or pulse shape of the stimulation signal.

In some examples, the groups of sense electrodes that are closest to the tissue site with the highest relative beta band (or other selected frequency band) activity within brain 28 may provide the best relative efficacy when stimulation therapy is delivered via the subset of electrodes of the sense electrode combination. Thus, in some examples, the stimulation electrode combination may comprise one or more electrodes from these groups of sense electrodes. In some examples, electrical stimulation may be delivered to substantially the same location at which a bioelectrical brain signal having a relatively high relative beta band power was sensed in order to effectively suppress the abnormal synchronization of beta frequency band activity associated with the patient's movement disorder.

In other examples, the stimulation electrode combination may comprise a different subset of electrodes than the groups of sense electrodes that are closest to the tissue site with the highest relative beta band activity. For example, a sense electrode combination may include at least two electrodes 24, 26 of leads 20A, 20B, whereas a stimulation electrode combination may include a single electrode of leads 20A, 20B (e.g., to provide unipolar stimulation) or more than two electrodes. In a unipolar configuration, stimulation may be provided between an electrode of one of the leads 20A, 20B and a housing of IMD 16 or another reference electrode located farther away. In the case of stimulation electrode combinations, it may be possible for more than one electrode to share a polarity. Therefore, in some cases, the stimulation electrode combination can include more electrodes than the sense electrode combination. If the stimulation electrode combination and an associated group of sense electrodes include at least one different electrode, the stimulation electrode combination and sense electrode combination may be positioned within different regions of brain 28. The regions may or may not overlap.

In some examples, the sense electrodes closest to the highest relative beta band activity within brain 28 may be mapped to a stimulation electrode combination that may provide relatively efficacious stimulation therapy. For example, the sense electrode combinations and the stimulation electrode combinations may be related by a functional relationship between different regions of brain 28. For example, a group of sense electrodes that senses a bioelectrical signal having a relatively high beta band power within a first part of the thalamus of brain 28 may be mapped to a second part of the thalamus that is functionally connected to first part. This functional relationship may indicate that if electrical stimulation is delivered to the second part of the thalamus via a particular stimulation electrode combination, any irregular oscillations or other irregular brain activity within the first part of the thalamus may be effectively suppressed.

One example method in which relative beta band power levels are recorded, analyzed, and compared to one another, and in which the sense electrode with the highest power level is selected as the sense electrode closest to the target tissue site is described in U.S. patent application Ser. No. 12/563,845 by Carlson et al., entitled "STIMULATION ELECTRODE SELECTION," which was filed on Sep. 21, 2009 and is incorporated herein by reference in its entirety. This technique is useful for selecting stimulation electrode combinations based on the frequency domain characteristics of one or more bioelectrical brain signals sensed with respective sense electrode combinations. In some cases, however, when the bioelectrical brain signals are sensed with a bipolar sensing configuration (e.g., sensing between electrodes of leads 20A, 20B), the sense electrode combination with the highest recorded relative beta band power level may not be the closest to the target tissue site. For example, if the target tissue site (e.g., the site within brain 28 that exhibits the highest relative beta band power) is situated between two electrodes, the relative value for the electrode combination may have the lowest relative beta band power instead of the highest.

Techniques such as those described herein may facilitate determining the sense electrode or electrodes closest to a target tissue site, including in cases in which the target tissue site is between two sense electrodes. By comparing the relative beta band power levels of bioelectrical brain signals sensed with different electrodes (or different combinations of electrodes), a processor of a device (e.g., IMD 16 or programmer 14) can determine whether the target tissue site is closer to certain electrodes because the strength of the relative beta band power level is revealing of the location of the target tissue site relative to the electrodes.

Selecting one or more stimulation electrode combinations for therapy system 10 based on sensed bioelectrical brain signals may be useful for minimizing the amount of time required to select efficacious stimulation electrode combinations. In the example shown in FIG. 1, therapy system 10 comprises eight electrodes 24, 26, whereby any combination of the eight electrodes 24, 26 may be selected to provide stimulation therapy to brain 28. In existing techniques, a clinician may randomly select and test stimulation electrode combinations in order to find an efficacious stimulation electrode combination. In some cases, the clinician's knowledge and experience selecting stimulation electrode combinations may help limit the amount of time required to select stimulation electrode combinations. The clinician may select a stimulation electrode combination based on a balance of side effects experienced by patient 12 and the extent to which the symptoms of the patient's movement disorder (or other patient condition) are mitigated. In these existing techniques, the clinician may not consider the specific anatomical make-up of brain 28 of patient 12 to select electrode combinations to test, nor the particular physiological characteristics of patient 12 and the particular dysfunctional state of the patient's brain 28. The existing techniques for selecting and testing stimulation electrode combinations and identifying a relatively efficacious stimulation electrode combination may be relatively time consuming and tedious.

In contrast, the systems, devices, and techniques described herein for selecting a stimulation electrode combination utilize information that is specific to patient 12. In particular, sensed bioelectrical brain signals may provide a clinician with useful information that suggests an efficacious stimulation electrode combination for patient 12. The information for selecting an efficacious stimulation electrode combination may be in the form of one or more frequency domain characteristics of a bioelectrical brain signal sensed by a particular group of sense electrodes. Differences in the amplitude of the one or more frequency domain characteristics of bioelectrical signals sensed with different electrodes may provide additional information for determining a sense electrode or electrodes that are closest to a target tissue site within brain 28 and may facilitate selection of an efficacious stimulation electrode combination. The sensed bioelectrical brain signals are specific to patient 12 because they are sensed within the patient's brain 28, and, therefore, may be used to relatively quickly ascertain the stimulation electrode combinations that may provide efficacious therapy to the specific patient 12.

In addition to decreasing the time required to select an efficacious stimulation electrode combination, the techniques described herein may also help decrease the amount of expertise or experience required to find an efficacious stimulation electrode combination in an efficient manner. For example, as described in further detail below, programmer 14 or another computing device may automatically evaluate one or more groups of sense electrodes and determine which particular group of sense electrodes is associated with a stimulation electrode combination that may provide efficacious therapy to patient 12 based on the bioelectrical brain signals specific to patient 12 and specific to the actual lead placement within the patient's brain 28.

After selecting stimulation electrode combinations in accordance with the systems and techniques described herein, a clinician, alone or with the aid of a computing device, such as programmer 14, may select the other stimulation parameter values that provide efficacious therapy to patient 12. These other stimulation parameter values may include, for example, a frequency and amplitude of stimulation signals, and, in the case of stimulation pulses, a duty cycle and pulse width of the stimulation signals.

In some examples, after IMD 16 is implanted within patient 12 and programmed for chronic therapy delivery, IMD 16 may periodically reassess the selected stimulation electrode combination to determine whether another stimulation electrode combination may provide more efficacious therapy. IMD 16 may determine, for example, whether the target tissue site for stimulation therapy has changed, e.g., based on physiological changes in brain 28 or whether one or both leads 20A, 20B have migrated away from the original implant site within brain 28. In some examples, in order to periodically reassess the selected stimulation electrode combination, a processor of IMD 16 may periodically sense bioelectrical brain signals with one or more groups of sense electrodes comprising electrodes 24, 26 of leads 20A, 20B, respectively. The processor may determine whether stimulation should be delivered to brain 28 with a different stimulation electrode combination based on an analysis of the frequency band characteristics of the sensed bioelectrical brain signals. For example, the processor of IMD 16 may switch the subset of electrodes with which IMD 16 delivers stimulation to patient 12 if the currently selected stimulation electrode combination is not associated with a group of sense electrodes that is closest to a target tissue site exhibiting a bioelectrical signal having the highest relative beta band power. In this way, the stimulation electrode combination used by IMD 16 to deliver electrical stimulation to patient 12 may be dynamically changed in a closed-loop system.

Electrical stimulation generated by IMD 16 may be configured to manage a variety of disorders and conditions. In some examples, the stimulation generator of IMD 16 is configured to generate and deliver electrical pulses to patient 12 via electrodes of a selected stimulation electrode combination. However, in other examples, the stimulation generator of IMD 16 may be configured to generate and deliver a continuous wave signal, e.g., a sine wave or triangle wave. In either case, a signal generator within IMD 16 may generate the electrical stimulation therapy for DBS according to a therapy program that is selected at that given time in therapy. In examples in which IMD 16 delivers electrical stimulation in the form of stimulation pulses, a therapy program may include a set of therapy parameter values, such as a stimulation electrode combination for delivering stimulation to patient 12, pulse frequency, pulse width, and a current or voltage amplitude of the pulses. As previously indicated, the stimulation electrode combination may indicate the specific electrodes 24, 26 that are selected to deliver stimulation signals to tissue of patient 12 and the respective polarity of the selected electrodes.

IMD 16 may be implanted within a subcutaneous pocket above the clavicle, or, alternatively, the abdomen, back or buttocks of patient 12, on or within cranium 32 or at any other suitable site within patient 12. Generally, IMD 16 is constructed of a biocompatible material that resists corrosion and degradation from bodily fluids. IMD 16 may comprise a hermetic housing to substantially enclose components, such as a processor, therapy module, and memory.

As shown in FIG. 1, implanted lead extension 18 is coupled to IMD 16 via connector 30 (also referred to as a connector block or a header of IMD 16). In the example of FIG. 1, lead extension 18 traverses from the implant site of IMD 16 and along the neck of patient 12 to cranium 32 of patient 12 to access brain 28. In the example shown in FIG. 1, leads 20A and 20B (collectively "leads 20") are implanted within the right and left hemispheres, respectively, of patient 12 in order deliver electrical stimulation to one or more regions of brain 28, which may be selected based on the patient condition or disorder controlled by therapy system 10. The specific target tissue site and the stimulation electrodes used to deliver stimulation to the target tissue site, however, may be selected, e.g., using the algorithms described herein, e.g., with respect to FIGS. 7A, 7B, 9A-9C, 10, 14, and 21. Other lead 20 and IMD 16 implant sites are contemplated. For example, IMD 16 may be implanted on or within cranium 32, in some examples. Or leads 20 may be implanted within the same hemisphere or IMD 16 may be coupled to a single lead.

Although leads 20 are shown in FIG. 1 as being coupled to a common lead extension 18, in other examples, leads 20 may be coupled to IMD 16 via separate lead extensions or directly to connector 30. Leads 20 may be positioned to deliver electrical stimulation to one or more target tissue sites within brain 28 to manage patient symptoms associated with a movement disorder of patient 12. Leads 20 may be implanted to position electrodes 24, 26 at desired locations of brain 28 through respective holes in cranium 32. Leads 20 may be placed at any location within brain 28 such that electrodes 24, 26 are capable of providing electrical stimulation to target tissue sites within brain 28 during treatment. For example, electrodes 24, 26 may be surgically implanted under the dura mater of brain 28 or within the cerebral cortex of brain 28 via a burr hole in cranium 32 of patient 12, and electrically coupled to IMD 16 via one or more leads 20.

Example techniques for delivering therapy to manage a movement disorder are described in U.S. Patent Application Publication No. 2009/0099627 by Molnar et al., entitled, "THERAPY CONTROL BASED ON A PATIENT MOVEMENT STATE," which was filed on Sep. 25, 2008, which is incorporated herein by reference in its entirety. In some examples described by U.S. Patent Application Publication No. 2009/0099627 by Molnar et al., a brain signal, such as an EEG or ECoG signal, may be used to determine whether a patient is in a movement state or a rest state. The movement state includes the state in which the patient is generating thoughts of movement (i.e., is intending to move), attempting to initiate movement or is actually undergoing movement. The movement state or rest state determination may then be used to control therapy delivery. For example, upon detecting a movement state of the patient, therapy delivery may be activated in order to help patient 12 initiate movement or maintain movement, and upon detecting a rest state of patient 12, therapy delivery may be deactivated or otherwise modified.

In the example shown in FIG. 1, electrodes 24, 26 of leads 20 are shown as ring electrodes. Ring electrodes may be used in DBS applications because they are relatively simple to program and are capable of delivering an electrical field to any tissue adjacent to electrodes 24, 26. In other examples, electrodes 24, 26 may have different configurations. For example, in some examples, at least some of the electrodes 24, 26 of leads 20 may have a complex electrode array geometry that is capable of producing shaped electrical fields. The complex electrode array geometry may include multiple electrodes (e.g., partial ring or segmented electrodes) around the outer perimeter of each lead 20, rather than one ring electrode. In this manner, electrical stimulation may be directed in a specific direction from leads 20 to enhance therapy efficacy and reduce possible adverse side effects from stimulating a large volume of tissue. An example of a complex electrode array geometry including segmented electrodes is shown and described with reference to FIGS. 4A and 4B. In some examples, a housing of IMD 16 may include one or more stimulation and/or sensing electrodes. In alternative examples, leads 20 may have shapes other than elongated cylinders as shown in FIG. 1. For example, leads 20 may be paddle leads, spherical leads, bendable leads, or any other type of shape effective in treating patient 12 and/or minimizing invasiveness of leads 20.

In the example shown in FIG. 1, IMD 16 includes a memory (shown in FIG. 3) to store a plurality of therapy programs that each define a set of therapy parameter values. In some examples, IMD 16 may select a therapy program from the memory based on various parameters, such as a detected patient activity level, a detected patient state, based on the time of day, and the like. IMD 16 may generate electrical stimulation based on the selected therapy program to manage the patient symptoms associated with a movement disorder.

During a trial stage in which IMD 16 is evaluated to determine whether IMD 16 provides efficacious therapy to patient 12, a plurality of therapy programs may be tested and evaluated for efficacy. In addition, one or more stimulation electrode combinations may be selected for the one or more therapy programs based on frequency band characteristics of sensed bioelectrical brain signals, as described in further detail below. Therapy programs may be selected for storage within IMD 16 based on the results of the trial stage.

During chronic therapy in which IMD 16 is implanted within patient 12 for delivery of therapy on a non-temporary basis, IMD 16 may generate and deliver stimulation signals to patient 12 according to different therapy programs. In addition, in some examples, patient 12 may modify the value of one or more therapy parameter values within a single given program or switch between programs in order to alter the efficacy of the therapy as perceived by patient 12 with the aid of programmer 14. The memory of IMD 16 may store instructions defining the extent to which patient 12 may adjust therapy parameters, switch between programs, or undertake other therapy adjustments. Patient 12 may generate additional programs for use by IMD 16 via external programmer 14 at any time during therapy or as designated by the clinician.

External programmer 14 wirelessly communicates with IMD 16 as needed to provide or retrieve therapy information. Programmer 14 is an external computing device that the user, e.g., the clinician and/or patient 12, may use to communicate with IMD 16. For example, programmer 14 may be a clinician programmer that the clinician uses to communicate with IMD 16 and program one or more therapy programs for IMD 16. Alternatively, programmer 14 may be a patient programmer that allows patient 12 to select programs and/or view and modify therapy parameters. The clinician programmer may include more programming features than the patient programmer. In other words, more complex or sensitive tasks may only be allowed by the clinician programmer to prevent an untrained patient from making undesirable changes to IMD 16.

Programmer 14 may be a hand-held computing device with a display viewable by the user and an interface for providing input to programmer 14 (i.e., a user input mechanism). For example, programmer 14 may include a small display screen (e.g., a liquid crystal display (LCD) or a light emitting diode (LED) display) that presents information to the user. In addition, programmer 14 may include a touch screen display, keypad, buttons, a peripheral pointing device or another input mechanism that allows the user to navigate though the user interface of programmer 14 and provide input. If programmer 14 includes buttons and a keypad, the buttons may be dedicated to performing a certain function, i.e., a power button, or the buttons and the keypad may be soft keys that change in function depending upon the section of the user interface currently viewed by the user. Alternatively, the screen (not shown) of programmer 14 may be a touch screen that allows the user to provide input directly to the user interface shown on the display. The user may use a stylus or a finger to provide input to the display.

In other examples, programmer 14 may be a larger workstation or a separate application within another multi-function device, rather than a dedicated computing device. For example, the multi-function device may be a notebook computer, tablet computer, workstation, cellular phone, personal digital assistant or another computing device that may run an application that enables the computing device to operate as medical device programmer 14. A wireless adapter coupled to the computing device may enable secure communication between the computing device and IMD 16.

When programmer 14 is configured for use by the clinician, programmer 14 may be used to transmit initial programming information to IMD 16. This initial information may include hardware information, such as the type of leads 20 and the electrode arrangement, the position of leads 20 within brain 28, the configuration of electrode array 24, 26, initial programs defining therapy parameter values, and any other information the clinician desires to program into IMD 16. Programmer 14 may also be capable of completing functional tests (e.g., measuring the impedance of electrodes 24, 26 of leads 20).

The clinician may also store therapy programs within IMD 16 with the aid of programmer 14. During a programming session, the clinician may determine one or more therapy programs that may provide efficacious therapy to patient 12 to address symptoms associated with the patient condition, and, in some cases, specific to one or more different patient states, such as a sleep state, movement state or rest state. For example, the clinician may select one or more stimulation electrode combination with which stimulation is delivered to brain 28. During the programming session, patient 12 may provide feedback to the clinician as to the efficacy of the specific program being evaluated or the clinician may evaluate the efficacy based on one or more physiological parameters of patient 12 (e.g., muscle activity or muscle tone). Programmer 14 may assist the clinician in the creation/identification of therapy programs by providing a methodical system for identifying potentially beneficial therapy parameter values.

Programmer 14 may also be configured for use by patient 12. When configured as a patient programmer, programmer 14 may have limited functionality (compared to a clinician programmer) in order to prevent patient 12 from altering critical functions of IMD 16 or applications that may be detrimental to patient 12. In this manner, programmer 14 may only allow patient 12 to adjust values for certain therapy parameters or set an available range of values for a particular therapy parameter.

Programmer 14 may also provide an indication to patient 12 when therapy is being delivered, when patient input has triggered a change in therapy or when the power source within programmer 14 or IMD 16 needs to be replaced or recharged. For example, programmer 14 may include an alert LED, may flash a message to patient 12 via a programmer display, generate an audible sound or somatosensory cue to confirm patient input was received, e.g., to indicate a patient state or to manually modify a therapy parameter.

Programmer 14 is configured to communicate to IMD 16 and, optionally, another computing device, via wireless communication. Programmer 14, for example, may communicate via wireless communication with IMD 16 using radio frequency (RF) telemetry techniques known in the art. Programmer 14 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 14 may also communicate with other programming or computing devices via exchange of removable media, such as magnetic or optical disks, memory cards or memory sticks. Further, programmer 14 may communicate with IMD 16 and another programmer via remote telemetry techniques known in the art, communicating via a local area network (LAN), wide area network (WAN), public switched telephone network (PSTN), or cellular telephone network, for example.

Therapy system 10 may be implemented to provide chronic stimulation therapy to patient 12 over the course of several months or years. However, system 10 may also be employed on a trial basis to evaluate therapy before committing to full implantation. If implemented temporarily, some components of system 10 may not be implanted within patient 12. For example, patient 12 may be fitted with an external medical device, such as a trial stimulator, rather than IMD 16. The external medical device may be coupled to percutaneous leads or to implanted leads via a percutaneous extension. If the trial stimulator indicates DBS system 10 provides effective treatment to patient 12, the clinician may implant a chronic stimulator within patient 12 for relatively long-term treatment.

Figure 3:
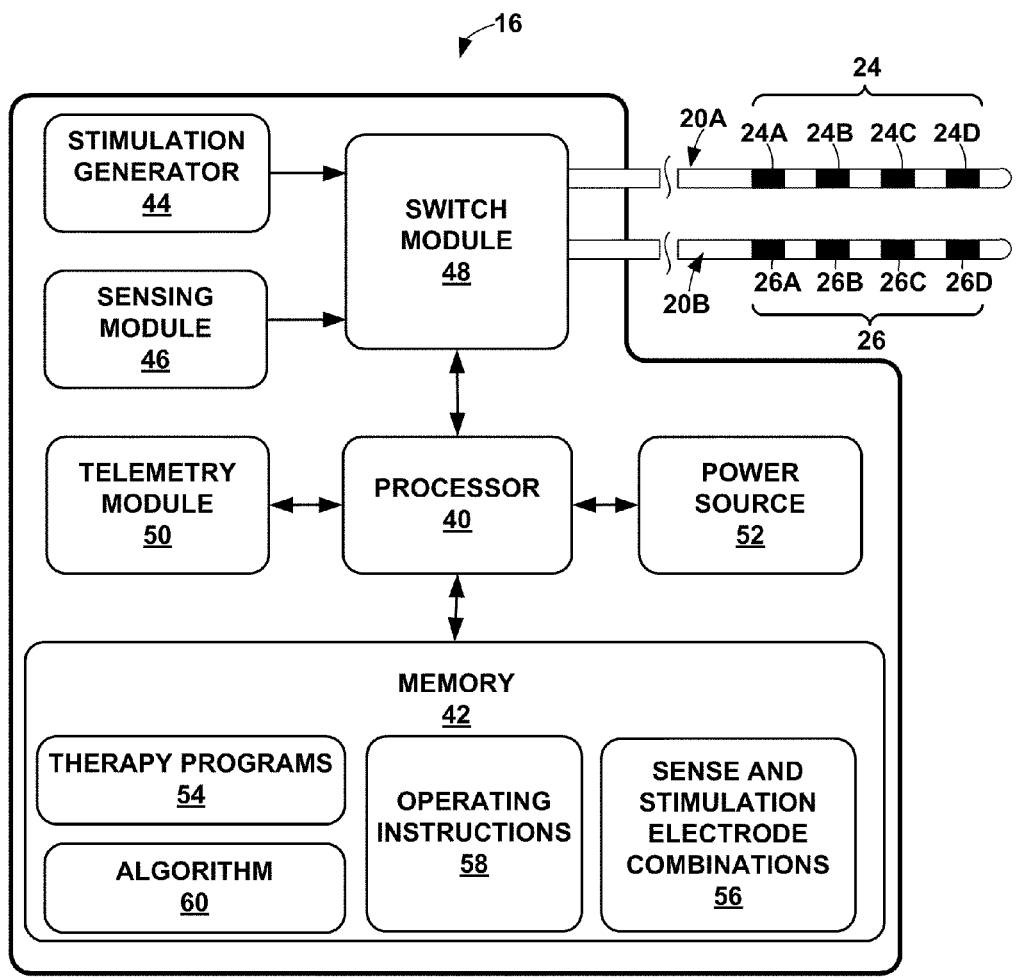
FIG. 3 is functional block diagram illustrating components of an example medical device.

FIG. 3 is a functional block diagram illustrating components of an example IMD 16. In the example shown in FIG. 3, IMD 16 includes processor 40, memory 42, stimulation generator 44, sensing module 46, switch module 48, telemetry module 50, and power source 52. Memory 42 may include any volatile or non-volatile media, such as a random access memory (RAM), read only memory (ROM), non-volatile RAM (NVRAM), electrically erasable programmable ROM (EEPROM), flash memory, and the like. Memory 42 may store computer-readable instructions that, when executed by processor 40, cause IMD 16 to perform various functions.

In the example shown in FIG. 3, memory 42 stores therapy programs 54, sense electrode combinations and associated stimulation electrode combinations 56, operating instructions 58, and algorithm 60 in separate memories within memory 42 or separate areas within memory 42. In addition, in some examples, memory 42 may store a bioelectrical brain signal sensed via at least some of the stored sense electrode combinations and/or one or more frequency band characteristics of the bioelectrical brain signals. Each stored therapy program 52 defines a particular set of electrical stimulation parameters, such as a stimulation electrode combination, electrode polarity, current or voltage amplitude, pulse width, and pulse rate. In some examples, individual therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis.

Sense and stimulation electrode combinations 56 stores sense electrode combinations and associated stimulation electrode combinations. As described above, in some examples, the sense and stimulation electrode combinations may include the same subset of electrodes 24, 26, or may include different subsets of electrodes. Thus, memory 42 can store a plurality of sense electrode combinations and, for each sense electrode combination, store information identifying the stimulation electrode combination that is associated with the respective sense electrode combination. The associations between sense and stimulation electrode combinations can be determined, e.g., by a clinician or automatically by processor 40. In some examples, corresponding sense and stimulation electrode combinations may comprise some or all of the same electrodes. In other examples, however, some or all of the electrodes in corresponding sense and stimulation electrode combinations may be different. For example, a stimulation electrode combination may include more electrodes than the corresponding sense electrode combination in order to increase the efficacy of the stimulation therapy. In some examples, as discussed above, stimulation may be delivered via a stimulation electrode combination to a tissue site that is different than the tissue site closest to the corresponding sense electrode combination but is within the same region, e.g., the thalamus, of brain 28 in order to mitigate any irregular oscillations or other irregular brain activity within the tissue site associated with the sense electrode combination.

Operating instructions 58 guide general operation of IMD 16 under control of processor 40, and may include instructions for measuring the impedance of electrodes 24, 26 and/or determining the distance between electrodes 24, 26. Algorithm 60 includes instructions for an algorithm that processor 40 may execute in order to determine which electrodes from a sense electrode combination are, for example, closest to a target tissue site for stimulation therapy to manage a particular patient. As described in further detail below, in some cases, the target tissue site is a tissue site within brain 28 that exhibits a high relative beta band power level based on bioelectrical signals measured by the sense electrode combination. However, the specific frequency band that is revealing of the target tissue site can differ depending on the anatomical region of brain 28 in which leads are implanted (e.g., the thalamus, anterior nucleus, and the like) or based on the patient condition. Different frequency bands may be biomarkers for different patient conditions.

Stimulation generator 44, under the control of processor 40, generates stimulation signals for delivery to patient 12 via selected combinations of electrodes 24, 26. An example range of electrical stimulation parameters believed to be effective in DBS to manage a movement disorder of patient include:

1. Frequency: between approximately 100 Hz and approximately 500 Hz, such as approximately 130 Hz.

2. Voltage Amplitude: between approximately 0.1 volts and approximately 50 volts, such as between approximately 0.5 volts and approximately 20 volts, or approximately 5 volts.

3. Current Amplitude: A current amplitude may be defined as the biological load in which the voltage is delivered. In a current-controlled system, the current amplitude, assuming a lower level impedance of approximately 500 ohms, may be between approximately 0.2 milliAmps to approximately 100 milliAmps, such as between approximately 1 milliAmps and approximately 40 milliAmps, or approximately 10 milliAmps. However, in some examples, the impedance may range between about 200 ohms and about 2 kiloohms.

4. Pulse Width: between approximately 10 microseconds and approximately 5000 microseconds, such as between approximately 100 microseconds and approximately 1000 microseconds, or between approximately 180 microseconds and approximately 450 microseconds.

Accordingly, in some examples, stimulation generator 44 generates electrical stimulation signals in accordance with the electrical stimulation parameters noted above. Other ranges of therapy parameter values may also be useful, and may depend on the target stimulation site within patient 12. While stimulation pulses are described, stimulation signals may be of any form, such as continuous-time signals (e.g., sine waves) or the like.

In each of the examples described herein, if stimulation generator 44 shifts the delivery of stimulation energy between two therapy programs, processor 40 of IMD 16 may provide instructions that cause stimulation generator 44 to time-interleave stimulation energy between the electrode combinations of the two therapy programs, as described in commonly-assigned U.S. patent application Ser. No. 11/401,100 by Steven Goetz et al., entitled, "SHIFTING BETWEEN ELECTRODE COMBINATIONS IN ELECTRICAL STIMULATION DEVICE," and filed on Apr. 10, 2006, the entire content of which is incorporated herein by reference. In the time-interleave shifting example, the amplitudes of the electrode combinations of the first and second therapy program are ramped downward and upward, respectively, in incremental steps until the amplitude of the second electrode combination reaches a target amplitude. The incremental steps may be different between ramping downward or ramping upward. The incremental steps in amplitude can be of a fixed size or may vary, e.g., according to an exponential, logarithmic or other algorithmic change. When the second electrode combination reaches its target amplitude, or possibly before, the first electrode combination can be shut off. Other techniques for shifting the delivery of stimulation signals between two therapy programs may be used, in other examples.

Processor 40 may include any one or more of a microprocessor, a controller, a digital signal processor (DSP), an application specific integrated circuit (ASIC), a field-programmable gate array (FPGA), discrete logic circuitry, and the functions attributed to processor 40 herein may be embodied as firmware, hardware, software or any combination thereof. Processor 40 controls stimulation generator 44 according to therapy programs 54 stored in memory 42 to apply particular stimulation parameter values specified by one or more of programs, such as amplitude, pulse width, and pulse rate.

In the example shown in FIG. 3, the set of electrodes 24 includes electrodes 24A, 24B, 24C, and 24D, and the set of electrodes 26 includes electrodes 26A, 26B, 26C, and 26D. Processor 40 also controls switch module 48 to apply the stimulation signals generated by stimulation generator 44 to selected combinations of electrodes 24, 26. In particular, switch module 48 may couple stimulation signals to selected conductors within leads 20, which, in turn, deliver the stimulation signals across selected electrodes 24, 26. Switch module 46 may be a switch array, switch matrix, multiplexer, or any other type of switching module configured to selectively couple stimulation energy to selected electrodes 24, 26 and to selectively sense bioelectrical brain signals with selected electrodes 24, 26. Hence, stimulation generator 44 is coupled to electrodes 24, 26 via switch module 46 and conductors within leads 20. In some examples, however, IMD 16 does not include switch module 46.

Stimulation generator 44 may be a single channel or multi-channel stimulation generator. In particular, stimulation generator 44 may be capable of delivering a single stimulation pulse, multiple stimulation pulses, or a continuous signal at a given time via a single electrode combination or multiple stimulation pulses at a given time via multiple electrode combinations. In some examples, however, stimulation generator 44 and switch module 48 may be configured to deliver multiple channels on a time-interleaved basis. For example, switch module 48 may serve to time divide the output of stimulation generator 44 across different electrode combinations at different times to deliver multiple programs or channels of stimulation energy to patient 12.

In some examples, processor 40 may dynamically change the selected combinations of electrodes 24, 26, i.e., the stimulation electrode combination, based on one or more frequency domain characteristics of bioelectrical signals sensed within brain 28. Sensing module 46, under the control of processor 40, may sense bioelectrical brain signals and provide the sensed bioelectrical brain signals to processor 40. Processor 40 may control switch module 48 to couple sensing module 46 to a selected combinations of electrodes 24, 26, i.e., a sense electrode combination. In this way, IMD 16 is configured such that sensing module 46 may sense bioelectrical brain signals with a plurality of different sense electrode combinations. Switch module 48 may be electrically coupled to the selected electrodes 24, 26 via the conductors within the respective leads 20, which, in turn, deliver the bioelectrical brain signal sensed across the selected electrodes 24, 26 to sensing module 46. The bioelectrical brain signal may include electrical signals that are indicative of electrical activity within brain 28 of patient 12.

Although sensing module 46 is incorporated into a common housing with stimulation generator 44 and processor 40 in FIG. 3, in other examples, sensing module 46 may be in a separate housing from IMD 16 and may communicate with processor 40 via wired or wireless communication techniques. Example bioelectrical brain signals include, but are not limited to, a signal generated from local field potentials within one or more regions of brain 28. EEG and ECoG signals are examples of local field potentials that may be measured within brain 28. However, local field potentials may include a broader genus of electrical signals within brain 28 of patient 12.

Processor 40 may analyze a plurality of bioelectrical brain signals, e.g., by determining relative values of signal characteristics (e.g., potentials or frequency domain characteristics) of the biosignal, to evaluate different stimulation electrode combinations. As previously indicated, a stimulation electrode combination may be associated with a sense electrode combination in memory 42. Processor 40 may evaluate different stimulation electrode combinations by, at least in part, sensing bioelectrical brain signals with one or more of the sense electrode combinations associated with a respective one of the stimulation electrode combinations and analyzing a frequency domain characteristic of the sensed bioelectrical brain signals. For example, processor 40 may determine a relative value of the frequency domain characteristic, e.g., relative beta band power level, based on bioelectrical signals sensed by two sense electrodes, may compare the relative values of a plurality of sense electrode combinations, and may determine the sense electrode or electrodes that are located closest to the target tissue site based on the relative values.

A frequency domain characteristic of the biosignal may include, for example, a power level (or energy) within one or more frequency bands of the biosignal, a ratio of the power level in two or more frequency bands, a correlation in change of power between two or more frequency bands, a pattern in the power level of one or more frequency bands over time, and the like. In some examples, processor 40 may adjust a previously selected stimulation electrode combination (e.g., by changing a polarity of an electrode of the combination or by adding or removing an electrode from the combination) or otherwise select a stimulation electrode combination by selecting a stimulation electrode combination that is associated with one or more sense electrodes that are closest to a target tissue site, as indicated by a bioelectrical signal comprising the highest relative beta band power level compared to the other sensed bioelectrical brain signals. In other examples, processor 40 may select a stimulation electrode combination that is associated with the sense electrode combination that is closest to a target tissue site, as indicated by a bioelectrical brain signal comprising a power level in a particular frequency band above a threshold value, which may be stored in memory 42.

In some examples, processor 40 implements algorithm 60 stored by memory 42 in order to determine which individual sense electrodes are located closest to a target tissue site, e.g., a region of brain 28 that exhibits a bioelectrical signal with the highest relative beta band power level. Processor 40 may then select a stimulation electrode combination based on determining which sense electrodes are located closest to the target tissue site in order to provide the most effective therapy to brain 28. For example, processor 40 may select a stimulation electrode combination in order to provide stimulation therapy In some examples, algorithm 60 includes instructions that cause processor 40 to evaluate the relative beta band power levels for a plurality of bioelectrical signals measured by a plurality of sense electrode combinations and determine which sense electrode combination is closest to the target tissue site with the highest relative beta band power level. Processor 40 implements algorithm 60 to determine the individual sense electrode within the sense electrode combination that is closest to the target tissue site with the highest relative beta band power level.

Telemetry module 50 supports wireless communication between IMD 16 and an external programmer 14 or another computing device under the control of processor 40. Processor 40 of IMD 16 may receive, as updates to programs, values for various stimulation parameters such as amplitude and electrode combination, from programmer 14 via telemetry module 50. The updates to the therapy programs may be stored within therapy programs 54 portion of memory 42. Telemetry module 50 in IMD 16, as well as telemetry modules in other devices and systems described herein, such as programmer 14, may accomplish communication by radiofrequency (RF) communication techniques. In addition, telemetry module 50 may communicate with external medical device programmer 14 via proximal inductive interaction of IMD 16 with programmer 14. Accordingly, telemetry module 50 may send information to external programmer 14 on a continuous basis, at periodic intervals, or upon request from IMD 16 or programmer 14.

Power source 52 delivers operating power to various components of IMD 16. Power source 52 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

Throughout the disclosure, a group of electrodes may refer to any electrodes located at the same position along the longitudinal axis of one or more leads. A group of electrodes may include one or more electrodes.

Figure 4A:
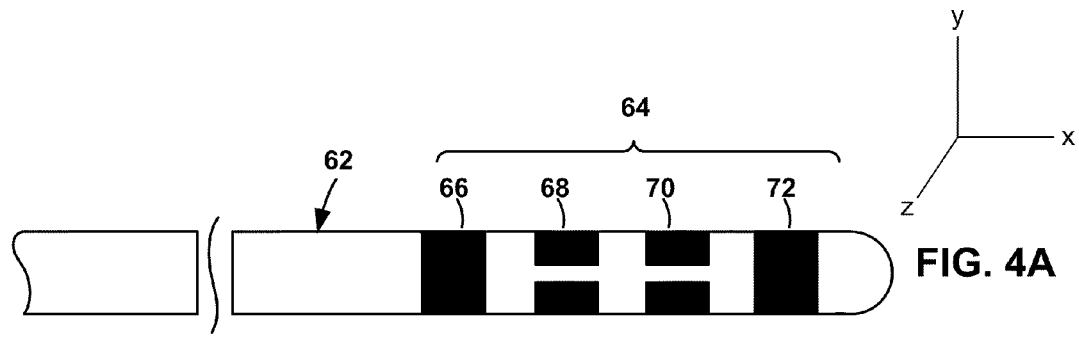
FIGS. 4A and 4B are diagrams illustrating another example electrode configuration of a medical lead.
Figure 4B:
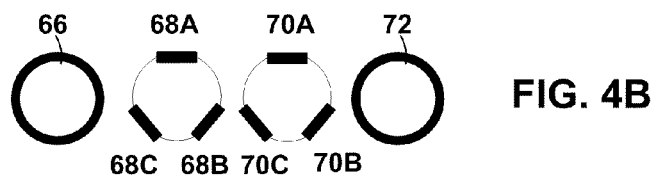

FIGS. 4A and 4B illustrate an example lead 62 and groups of electrodes 64 that may be used with IMD 16 instead of or in addition to one or both leads 20A, 20B including respective sets of electrodes 24, 26. FIG. 4A shows a two-dimensional side view in the x-y plane of lead 62, which includes four groups of electrodes 66, 68, 70, and 72. FIG. 4B shows a cross-sectional view in the y-z plane of each of the four groups of electrodes. Groups of electrodes 66 and 72 each comprise one ring electrode, which may be similar to each of electrodes 24, 26 shown in FIG. 3. In contrast, groups of electrodes 68 and 70 each comprise three segmented electrodes 68A-68C and 70A-70C distributed around the outer perimeter of lead 62. In other examples, lead 62 may comprise any number and combination of groups of ring electrodes or segmented electrodes. For example, lead 62 may comprise only groups of segmented electrodes. As another example, groups 68, 70 of electrodes may comprise more than three segmented (or partial ring) electrodes or one or two segmented or partial ring electrodes.

Figure 5:
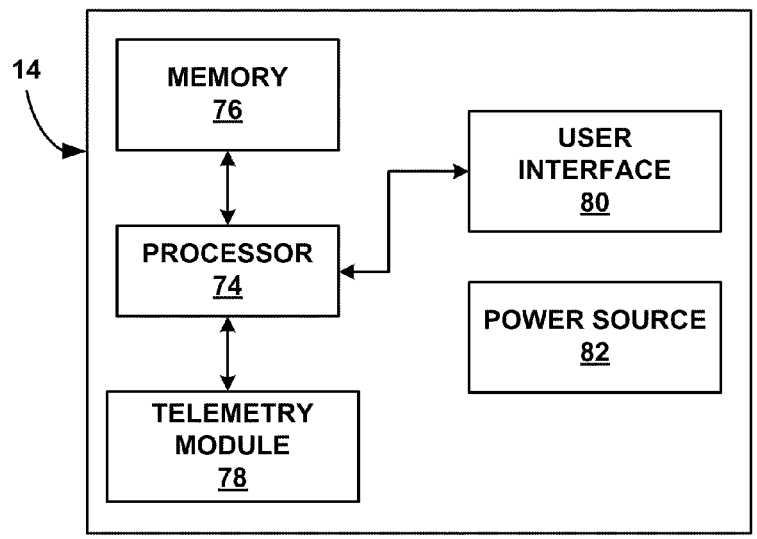
FIG. 5 is a functional block diagram illustrating components of an example medical device programmer.

FIG. 5 is a conceptual block diagram of an example external medical device programmer 14, which includes processor 74, memory 76, telemetry module 78, user interface 80, and power source 82. Processor 74 controls user interface 80 and telemetry module 78, and stores and retrieves information and instructions to and from memory 76. Programmer 14 may be configured for use as a clinician programmer or a patient programmer. Processor 74 may comprise any combination of one or more processors including one or more microprocessors, DSPs, ASICs, FPGAs, or other equivalent integrated or discrete logic circuitry. Accordingly, processor 74 may include any suitable structure, whether in hardware, software, firmware, or any combination thereof, to perform the functions ascribed herein to processor 74.

A user, such as a clinician or patient 12, may interact with programmer 14 through user interface 80. User interface 80 includes a display (not shown), such as a LCD or LED display or other type of screen, to present information related to the therapy, such as information related to bioelectrical signals sensed via a plurality of sense electrode combinations. In addition, user interface 80 may include an input mechanism to receive input from the user. The input mechanisms may include, for example, buttons, a keypad (e.g., an alphanumeric keypad), a peripheral pointing device or another input mechanism that allows the user to navigate though user interfaces presented by processor 74 of programmer 14 and provide input.

If programmer 14 includes buttons and a keypad, the buttons may be dedicated to performing a certain function, i.e., a power button, or the buttons and the keypad may be soft keys that change in function depending upon the section of the user interface currently viewed by the user. Alternatively, the screen (not shown) of programmer 14 may be a touch screen that allows the user to provide input directly to the user interface shown on the display. The user may use a stylus or a finger to provide input to the display. In other examples, user interface 80 also includes audio circuitry for providing audible instructions or sounds to patient 12 and/or receiving voice commands from patient 12, which may be useful if patient 12 has limited motor functions. Patient 12, a clinician or another user may also interact with programmer 14 to manually select therapy programs, generate new therapy programs, modify therapy programs through individual or global adjustments, and transmit the new programs to IMD 16.

In some examples, at least some of the control of therapy delivery by IMD 16 may be implemented by processor 74 of programmer 14. For example, in some examples, processor 74 may receive a bioelectrical brain signal from IMD 16 or from a sensing module that is separate from IMD 16. The separate sensing module may, but need not be, implanted within patient 12. In some examples, processor 74 may select one or more stimulation electrode combinations based on the differences in amplitude of a frequency domain characteristic of bioelectrical brain signals sensed with different sense electrode combinations associated with at least one of the stimulation electrode combinations. Processor 74 may select a stimulation electrode combination for IMD 16 based on the analysis of the frequency domain characteristics of the sensed bioelectrical brain signals, e.g., by implementing an algorithm similar or identical to that implemented by IMD 16 and stored by memory 42 of IMD 16. Example algorithms are described below with respect to FIGS. 7A, 7B, 9A-9C, 10, 14, and 21. In some cases, e.g., after determining another stimulation electrode combination is desirable based on a comparison of the frequency domain characteristics of a plurality of bioelectrical brain signals sensed by a respective electrode combination, processor 74 may transmit a signal to IMD 16 to instruct IMD 16 to switch stimulation electrode combinations.

Processor 40 of IMD 16 may receive the signal from programmer 14 via its respective telemetry module 50 (FIG. 3). Processor 40 of IMD 16 may switch stimulation electrode combinations by selecting a stored therapy program from memory 42 based on the signal from processor 74 of programmer 14. Alternatively, processor 74 of programmer 14 may select a therapy program or a specific stimulation electrode combination and transmit a signal to IMD 16, where the signal indicates the therapy parameter values to be implemented by IMD 16 to help improve the efficacy of the stimulation to manage the patient's movement disorder. The indication may be, for example, an alphanumeric identifier or symbol that is associated with the therapy program in memory 42 of IMD 16.

Memory 76 may include instructions for operating user interface 80 and telemetry module 78, and for managing power source 82. Memory 76 may also store any therapy data retrieved from IMD 16 during the course of therapy. The clinician may use this therapy data to determine the progression of the patient condition in order to predict future treatment. Memory 76 may include any volatile or nonvolatile memory, such as RAM, ROM, EEPROM or flash memory. Memory 76 may also include a removable memory portion that may be used to provide memory updates or increases in memory capacities. A removable memory may also allow sensitive patient data to be removed before programmer 14 is used by a different patient.

Wireless telemetry in programmer 14 may be accomplished by RF communication or proximal inductive interaction of external programmer 14 with IMD 16. This wireless communication is possible through the use of telemetry module 78. Accordingly, telemetry module 78 may be similar to the telemetry module contained within IMD 16. In alternative examples, programmer 14 may be capable of infrared communication or direct communication through a wired connection. In this manner, other external devices may be capable of communicating with programmer 14 without needing to establish a secure wireless connection.

Power source 82 delivers operating power to the components of programmer 14. Power source 82 may include a battery and a power generation circuit to produce the operating power. In some examples, the battery may be rechargeable to allow extended operation. Recharging may be accomplished by electrically coupling power source 82 to a cradle or plug that is connected to an alternating current (AC) outlet. In addition, recharging may be accomplished through proximal inductive interaction between an external charger and an inductive charging coil within programmer 14. In other examples, traditional batteries (e.g., nickel cadmium or lithium ion batteries) may be used. In addition, programmer 14 may be directly coupled to an alternating current outlet to operate. Power source 82 may include circuitry to monitor power remaining within a battery. In this manner, user interface 80 may provide a current battery level indicator or low battery level indicator when the battery needs to be replaced or recharged. In some cases, power source 82 may be capable of estimating the remaining time of operation using the current battery.

Figure 6:
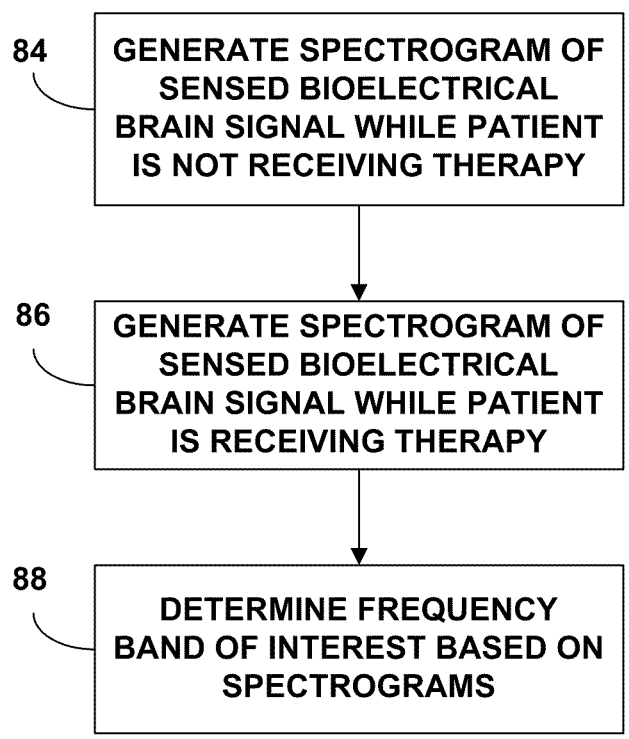
FIG. 6 is a flow diagram of an example technique for determining a frequency band of interest for evaluating sense electrode combinations.

FIG. 6 is a flow diagram of an example technique that processor 40 of IMD 16, processor 74 of programmer 14, or another computing device can implement to identify a frequency band of interest. Processor 40 can utilize the frequency band of interest as a signal characteristic with which to compare bioelectrical brain signals and select a stimulation electrode combination, as described in further detail below. Processor 40 is referred to throughout the description of FIG. 6, as well as FIGS. 7A, 7B, 9A-9C, 10, 14, and 21. In other examples, processor 74 of programmer 14 or another computing device may implement the technique shown in FIGS. 6, 7A, 7B, 9A-9C, 10, 14, and 21.

In the example shown in FIG. 6, processor 40 generates a spectrogram (e.g., as shown in FIG. 2) of a bioelectrical brain signal of patient 12 during a first time period in which patient 12 is in a pathological state, e.g., is not receiving any therapy to manage the movement disorder or other patient condition (84). Processor 40 generates a spectrogram during a second time period in which patient 12 is receiving therapy to manage the movement disorder or other patient condition (86). Processor 40 determines a frequency band of interest that indicates a biomarker for the patient's condition based on the spectrograms (88). In some examples, processor 40 may determine which frequency bands exhibited a relatively large and/or discernable change between the first and second time periods. For example, in the spectrogram shown in FIG. 2, the beta band activity decreased after the human subject began receiving a pharmaceutical agent to manage a movement disorder, as indicated by time period 38.

Processor 40 may utilize the frequency band of interest in order to select a sense electrode or electrode combination that is closest to a target tissue site in accordance with the techniques described herein. Additionally, processor 40 may select a stimulation electrode combination based on the frequency band of interest. In some examples, processor 40 may sense bioelectrical brain signals within brain 28 of patient 12 with each sense electrode combination of a plurality of stored sense electrode combinations. Processor 40 may select a stimulation electrode combination based on the sense electrode combination associated with one or more sensed bioelectrical brain signals having the greatest relative power level in the frequency band of interest. In other examples, processor 40 may select a stimulation electrode combination based on the sense electrode combination associated with a sensed bioelectrical brain signal having a lowest relative power level in the frequency band of interest. In some examples, the different sense electrode combinations and associated beta band power levels may be presented to a user, such as a clinician, via a display of a device, such as programmer 14.

Figure 7A:
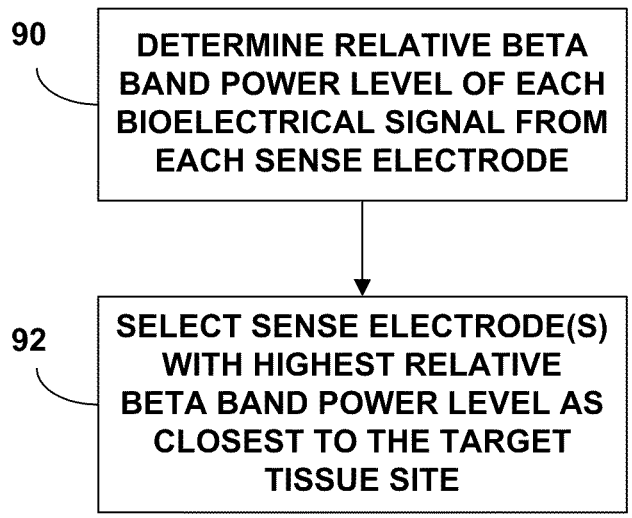
FIGS. 7A and 7B are flow diagrams illustrating general techniques for selecting sense electrode combinations that are closest to a target tissue site.
Figure 7B:
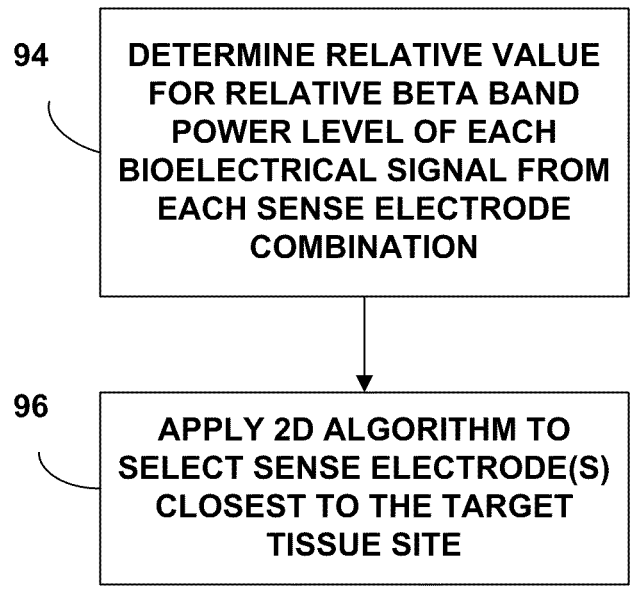

FIGS. 7A and 7B are flow diagrams of example techniques for selecting sense electrode combinations that are closest to a target tissue site. The target tissue site may be the tissue site within brain 28 of patient 12 that exhibits a bioelectrical signal with the highest relative power level in a particular frequency band or that exhibits another predetermined frequency domain characteristic (e.g., a lowest relative power level). As discussed above, with respect to movement disorders, a high relative beta band power level may be associated with abnormal oscillations or activity within brain 28. Selection of sense electrode combinations that are closest to the target tissue site may facilitate selection of stimulation electrode combinations that are most effective in providing stimulation therapy to patient 12.

Processor 40 controls sensing module 46 of IMD 16 to sense bioelectrical signals in the brain of patient 12 with a plurality of sense electrode combinations including one or more electrodes from electrodes 24, 26. In some examples, processor 40 controls sensing module 46 to sense bioelectrical signals with unipolar electrode configurations, in which sensing module 46 senses a bioelectrical signal between each of one or more individual electrodes 24, 26 and the housing of IMD 16 (e.g., a housing electrode coupled to or defined by an outer housing of IMD 16) or another reference. While sensing in a unipolar configuration may be useful for sensing bioelectrical brain signals, sensing between an electrode of one of the leads 20A, 20B and a housing of IMD 16 or another reference may introduce noise into the sensed brain signal and, in some cases, distort the sensed bioelectrical brain signal. For example, unipolar sensing of bioelectrical signals in brain 28 of patient 12 may result in the sensing of a relatively high amount of electrical cardiac activity of patient 12 or other electrical activity of patient 12 or external to patient 12 compared to bipolar sensing between electrodes 24, 26 of leads 20. Therefore, in other examples, processor 40 controls sensing module 46 to sense bioelectrical signals with bipolar electrode configurations, in which sensing module 46 senses a bioelectrical signal between pairs of electrodes 24, 26, e.g., between electrodes 24A and 24B, between electrodes 24A and 24D, etc. Unipolar and bipolar sensing configurations may also be used with other electrode configurations, such as the configuration defined by electrodes 66, 68, 70, and 72 of lead 62 (FIGS. 4A and 4B).

FIG. 7A is a flow diagram illustrating a general technique for selecting a group of sense electrodes when using a unipolar sensing configuration. As an example, processor 40 can control sensing module 46 (FIG. 3) of IMD 16 to sense bioelectrical signals with each of electrodes 24 in a unipolar configuration. For example, processor 40 may control sensing module 46 to sense a first bioelectrical signal between electrode 24A and the housing of IMD 16 (e.g., an electrically conductive outer housing of IMD 16 or an electrode coupled to a conductive or nonconductive outer housing), a second bioelectrical signal between electrode 24B and the housing of IMD 16, a third bioelectrical signal between electrode 24C and the housing of IMD 16, and a fourth bioelectrical signal between electrode 24D and the housing of IMD 16.

Processor 40 determines the relative beta band power level for each of the first, second, third, and fourth bioelectrical signals (90). Processor 40 selects the one or more sense electrodes that sensed the bioelectrical signal with the highest relative beta band power as the sense electrode closest to the target tissue site (92). In some examples, processor 40 selects a stimulation electrode combination or a therapy program based on selecting the sense electrodes closest to the target tissue site. In some examples, the stimulation electrode combination may comprise some or all of the sense electrodes closest to the target tissue site. In other examples, the stimulation electrode combination may comprise different electrodes than the sense electrodes closest to the target tissue site.

FIG. 7B is a flow diagram illustrating an example technique for selecting a group of sense electrodes based on relative values of relative power levels in a selected frequency band in order to simulate a bipolar sensing configuration. In an example of the technique shown in FIG. 7B, processor 40 controls sensing module 46 of IMD 16 to sense bioelectrical signals with each of the electrodes 24 in a unipolar configuration. For example, processor 40 may control sensing module 46 to sense a first bioelectrical signal with electrode 24A and a reference (e.g., a housing electrode), a second bioelectrical signal with electrode 24B and a reference, a third bioelectrical signal with electrode 24C and a reference, and a fourth bioelectrical signal with electrode 24D and a reference.

After sensing the bioelectrical brain signals with electrodes 24, processor 40 determines the relative value of the relative beta band power level for each combination of the first, second, third, and fourth bioelectrical signals (94). For example, processor 40 determines a first relative value by determining the absolute difference in the relative beta band power levels of the first and second bioelectrical signals, a second relative value by determining the absolute difference in the relative beta band power levels of the first and third bioelectrical signals, a third relative value by determining the absolute difference in the relative beta band power levels of the first and fourth bioelectrical signals, a fourth relative value by determining the absolute difference in the relative beta band power levels of the second and third bioelectrical signals, a fifth relative value by determining the absolute difference in the relative beta band power levels of the second and fourth bioelectrical signals, and a sixth relative value by determining the absolute difference in the relative beta band power levels of the third and fourth bioelectrical signals.

Each of the determined relative values indicates the difference in relative beta band power levels for signals sensed by respective electrodes. Therefore, the relative value indicates the relative beta band power level of a bioelectrical signal that is sensed between the electrodes associated with the sensed bioelectrical brain signals, i.e., in a bipolar electrode configuration. For example, a relative value determined based on the first and second bioelectrical signals indicates (e.g., is substantially equal to) the relative beta band power level of a bioelectrical signal that is sensed between electrodes 24A, 24B. As a result, the technique for determining the relative values of the relative beta band power level of bioelectrical brain signals sensed via different electrodes can be used as a surrogate for bipolar sensing and determining a beta band power level of a bioelectrical signal sensed via the bipolar sensing configuration. In each example described herein that utilizes a relative value of the relative beta band power levels of bioelectrical brain signals sensed in a unipolar configuration, the relative beta band power level of a bioelectrical signal that is sensed between electrodes in a multipolar (e.g., bipolar) configuration can be substituted to arrive at the same stimulation electrode combination selection.

After determining the relative value of the relative beta band power level for each combination of the first, second, third, and fourth bioelectrical signals (94), processor 40 accesses and execute algorithm 60 in order to select the one or more sense electrodes closest to the target tissue site based on the relative values for the relative beta band power levels (96). In some examples, processor 40 selects a stimulation electrode combination or a therapy program based on the pair of sense electrodes determined to be closest to the target tissue site. In some examples, the stimulation electrode combination may comprise some or all of the sense electrodes closest to the target tissue site. In other examples, the stimulation electrode combination may comprise different electrodes than the sense electrodes closest to the target tissue site.

Figure 8:
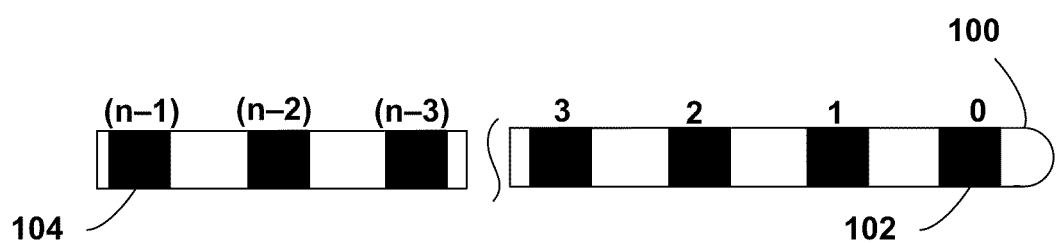
FIG. 8 is a diagram illustrating a medical lead with a plurality of electrodes.

The systems and techniques described herein for selecting one or more sense electrodes that are closest to a target tissue site may be applicable to medical leads with any number and configuration of electrodes. FIG. 8 illustrates an example lead 100 with a number n of electrodes between the most distal electrode 102 of lead 100, numbered 0, to the most proximal electrode 104 of lead 100, numbered n−1. With respect to the flow diagrams in FIGS. 9A-9C, combinations of sense electrodes will be identified using the electrode numbering system illustrated in FIG. 8 that includes electrodes numbered 0 through n−1. For example, the electrode combination of the most distal pair of electrodes on lead 100 will be referred to as E10, the electrode combination between the second most distal pair of electrodes on lead 100 will be referred to as E21, the electrode combination between the most distal and the most proximal electrodes on lead 100 will be referred to as E(n−1)0, and so forth.

Figure 9A:
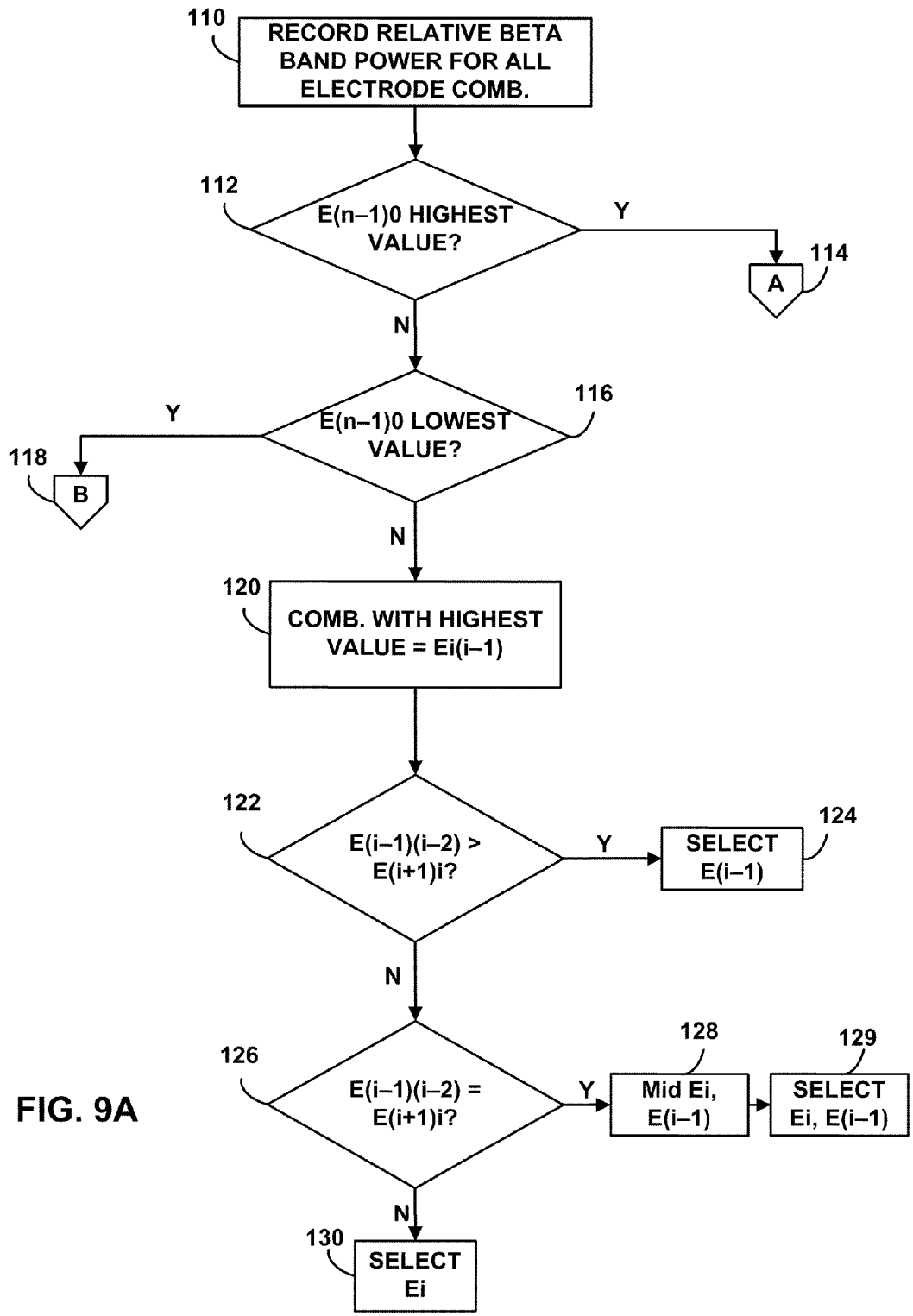
FIGS. 9A-9C are flow diagrams illustrating a general algorithm that can be implemented to select electrodes that are closest to a target tissue site.
Figure 9B:
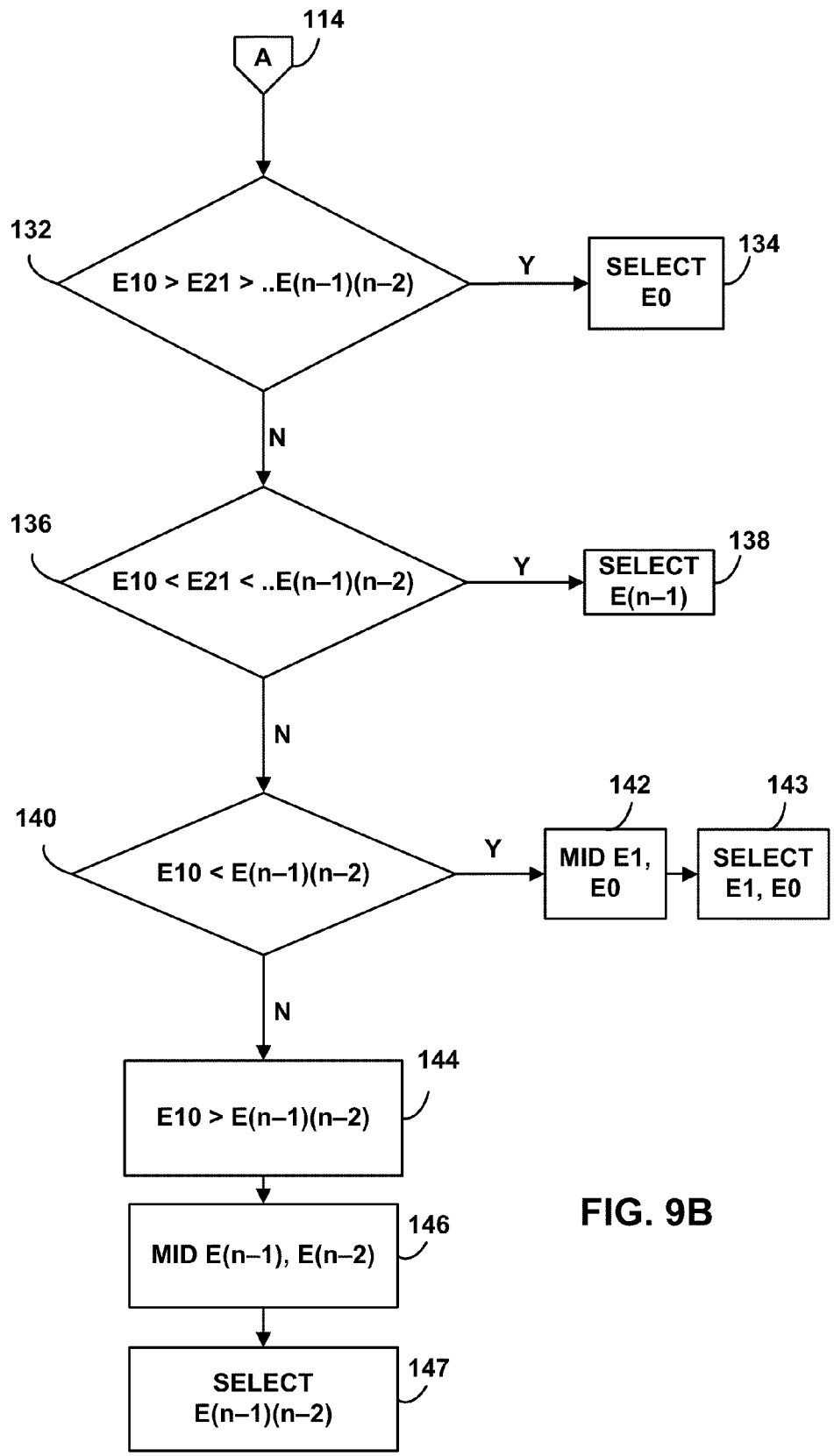
Figure 9C:
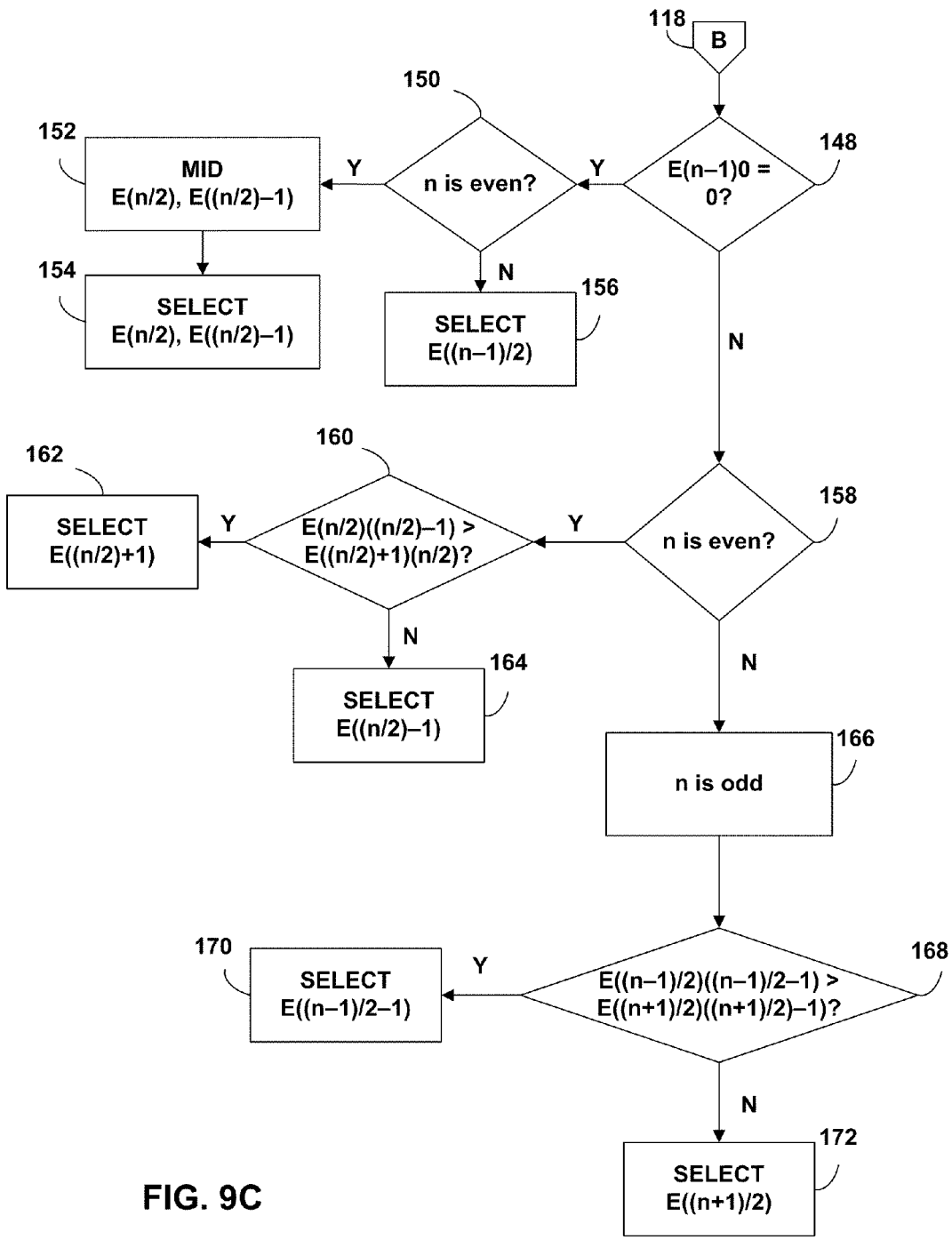

FIGS. 9A, 9B, and 9C illustrate an example technique for selecting one or more sense electrodes of lead 100 (FIG. 8) that are closest to a target tissue site within brain 28. As previously described, the target tissue site can be, for example, the tissue site exhibiting a relatively high beta band energy or the tissue site within brain 28 that exhibits another predetermined frequency band characteristic. The target tissue site can be, for example, the tissue site at which therapy delivery (e.g., stimulation or drug delivery) provides efficacious therapy to patient 12 to mitigate symptoms of the patient condition. Processor 40 of IMD 16 can implement algorithm 60 to execute each of the steps of algorithm 60. However, in other examples, the techniques shown in FIGS. 9A-9C can be carried out by a different processor, such as processor 74.

The relative beta band power level may be a ratio of the power in a beta band of the sensed signal to the overall power of the sensed signal, and may be used instead of the beta band power in order to normalize the bioelectrical signals sensed by sense electrodes located in different regions of brain 28. The relative value of the relative beta band power level between two electrodes (i.e., the electrodes of an electrode combination) may be defined as the magnitude of the difference in amplitude between the relative beta band power levels sensed with each of the two electrodes in the electrode combination in a unipolar configuration. For example, the relative value of the relative beta band power levels for electrode combination 24A-24B may be defined as the magnitude of the difference in the amplitude of the relative beta band power level sensed by electrode 24A and a reference electrode and the amplitude of the relative beta band power level sensed by electrode 24B and a reference electrode.

In general, the technique shown in FIGS. 9A-9C comprises determining if the target tissue site is closest to either of the most distal or the most proximal electrodes, i.e., either of electrodes 0 or n−1, by determining whether the relative value of the relative beta band power level between these two electrodes is the highest. If this relative value is the highest, the target tissue site is closest to either the most distal or the most proximal electrode. If this relative value is not the highest, the technique comprises determining if the target tissue site is closest to the electrodes in the middle of the lead by determining whether the relative value of the relative beta band power level between the most distal and the most proximal electrodes is the lowest. If this relative value is the lowest, the target tissue site is closest to the middle electrode or electrodes. If this value is neither the highest nor the lowest, the technique comprises determining which pair of adjacent electrodes sensed the highest relative value of the relative beta band power level and determining that the target tissue site is closest to one of this pair of adjacent electrodes.

As shown in FIG. 9A, processor 40 determines the relative beta band power level for each bioelectrical signal sensed by each adjacent electrode combination, i.e., E10, E21, E32, etc. and for the electrode combination comprising the most proximal and the most distal electrodes, i.e., E(n−1)0 (110). Next, processor 40, while implementing algorithm 60, determines whether electrode combination E(n−1)0 has the highest relative value (112). If processor 40 determines that electrode combination E(n−1)0 has the highest relative value, processor 40 executes the portion of algorithm 60 referred to as "part A" for ease of description (114), which will be described with respect to FIG. 9B.

If, on the other hand, processor 40 determines that electrode combination E(n−1)0 does not have the highest relative value, processor 40 determines whether electrode combination E(n−1)0 instead has the lowest relative value (116). If processor 40 determines that electrode combination E(n−1)0 has the lowest relative value, processor 40 executes the portion of algorithm 60 referred to as "part B" for ease of description, which will be described with respect to FIG. 9C (118).

If processor 40 determines that electrode combination E(n−1)0 has neither the highest nor the lowest relative value, processor 40 determines which electrode combination has the highest relative value. The electrode combination with the highest relative value is referred to as electrode combination Ei(i−1) (120). Next, processor 40 determines whether the electrode combination proximal to the electrode combination with the highest relative value, i.e., electrode combination E(i−1)(i−2), has a higher relative value than the electrode combination distal to the electrode combination with the highest relative value, i.e., electrode combination E(i+1)i (122). If processor 40 determines that electrode combination E(i−1)(i−2) has a higher relative value than electrode combination E(i+1)i, processor 40 selects the proximal electrode, i.e., E(i−1), of the electrode combination with the highest relative value as the electrode closest to the target tissue site (124). Processor 40 may select a stimulation electrode combination based on determining that E(i−1) is the electrode closest to the target tissue site. In some examples, processor 40 selects a stimulation electrode combination including electrode E(i−1) based on determining that E(i−1) is the electrode closest to the target tissue site.

If, on the other hand, processor 40 determines that electrode combination E(i−1)(i−2) does not have a higher relative value than electrode combination E(i+1)i, processor 40 determines whether electrode combination E(i−1)(i−2) has a relative value substantially equal to the relative value of electrode combination E(i+1)i (126). If processor 40 determines that electrode combination E(i−1)(i−2) has a relative value equal to the relative value of electrode combination E(i+1)i, processor 40 determines that the target tissue site is located closest to the midpoint of electrodes Ei and E(i−1) (128) and selects electrodes Ei and E(i−1) as the electrodes closest to the target tissue site (129). Processor 40 may select a stimulation electrode combination based on determining that Ei and E(i−1) are the electrodes closest to the target tissue site. In some examples, processor 40 selects a stimulation electrode combination including electrodes Ei and E(i−1) based on determining that Ei and E(i−1) are the electrodes closest to the target tissue site.

If processor 40 determines that electrode combination E(i−1)(i−2) does not have a relative value equal to the relative value of electrode combination E(i+1)i, processor 40 selects the distal electrode, i.e., electrode Ei, of the electrode combination with the highest relative value as the electrode closest to the target tissue (130).

FIG. 9B, as mentioned above, illustrates part A of algorithm 60, which processor 40 implements upon determining that electrode combination E(n−1)0 has the highest relative value (114). Processor 40 determines whether the most distal pair of adjacent electrodes, i.e., electrode combination E10, has a higher relative value than the second most distal pair of adjacent electrodes, i.e., electrode combination E21, and whether electrode combination E21 has a higher relative value than the third most distal pair of adjacent electrodes, i.e., electrode combination E32, and whether electrode combination E32 has a higher relative value than the fourth most distal pair of adjacent electrodes, i.e., electrode combination E43, and so on until processor 40 determines whether electrode combination E(n−2)(n−3) has a higher relative value than electrode combination E(n−1)(n−2) (132). If processor 40 determines that electrode combination E10 has a higher relative value than electrode combination E21 and that electrode combination E21 has a higher relative value than electrode combination E32 and that electrode combination E32 has a higher relative value than electrode combination E43 and so on until processor 40 determines that electrode combination E(n−2)(n−3) has a higher relative value than electrode combination E(n−1)(n−2), processor 40 selects the most distal electrode E0 as the electrode closest to the target tissue site (134).

If, on the other hand, processor 40 determines that these criteria are not met, processor 40 determines whether the most distal pair of adjacent electrodes, i.e., electrode combination E10, has a lower relative value than the second most distal pair of adjacent electrodes, i.e., electrode combination E21, and whether electrode combination E21 has a lower relative value than the third most distal pair of adjacent electrodes, i.e., electrode combination E32, and whether electrode combination E32 has a lower relative value than the fourth most distal pair of adjacent electrodes, i.e., electrode combination E43, and so on until processor 40 determines whether electrode combination E(n−2)(n−3) has a lower relative value than electrode combination E(n−1)(n−2) (136). If processor 40 determines that electrode combination E10 has a lower relative value than electrode combination E21 and that electrode combination E21 has a lower relative value than electrode combination E32 and that electrode combination E43 has a lower relative value than electrode combination E32 and so on until processor 40 determines that electrode combination E(n−2)(n−3) has a lower relative value than electrode combination E(n−1)(n−2), processor 40 selects the most proximal electrode E(n−1) as the electrode closest to the target tissue site (138).

If processor 40 determines that these criteria are not met, processor 40 determines whether the most distal pair of electrodes E10 has a lower relative value than the most proximal pair of electrodes E(n−1)(n−2) (140). If processor 40 determines that electrode combination E10 has a lower relative value than electrode combination E(n−1)(n−2), processor 40 determines that the target tissue site is closest to the midpoint of the most distal electrode pair E10 (142) and selects electrodes E1 and E0 as the electrodes closest to the target tissue site (143). If processor 40 determines that electrode combination E10 does not have a lower relative value than electrode combination E(n−1)(n−2), processor 40 determines that electrode combination E10 has a higher relative value that electrode combination E(n−1)(n−2) (144) and determines that the target tissue site is closest to the midpoint of the most proximal electrode pair E(n−1)(n−2) (146). Processor 40 then selects electrodes E(n−1) and E(n−2) as being closest to the target tissue site (147).

FIG. 9C, as mentioned above, illustrates part B of algorithm 60, which processor 40 executes upon determines that electrode combination E(n−1)0 has the lowest relative value (118) (FIG. 9A). Processor 40 determines whether electrode combination E(n−1)0 has a relative value equal to zero. If processor 40 determines that electrode combination E(n−1)0 has a relative value equal to zero, processor 40 determines whether the number of electrodes n is even (150). If the number of electrodes n is even, processor 40 determines that the target tissue site is located closest to the midpoint between the middle two electrodes E(n/2) and E((n/2)−1) (152). Processor 40 then selects E(n/2) and E((n/2)−1) as the electrodes closest to the target tissue site (154). If processor 40 determines that the number of electrodes n is not even (150), processor 40 determines that the middle electrode E((n−1)/2) is the electrode closest to the target tissue site (156).

If processor 40 determines that electrode combination E(n−1)0 does not have a relative value equal to 0 (148), processor 40 determines whether the number of electrodes n of the lead is even (158). If processor 40 determines that the number of electrodes n is even, processor 40 determines whether the middle electrode combination E(n/2)((n/2)−1) has a higher relative value than the electrode combination comprising the proximal electrode of the middle electrode pair and the electrode proximal to the proximal electrode of the middle electrode pair, electrode combination E((n/2)+1)(n/2) (160). If processor 40 determines that electrode combination E(n/2)((n/2)−1) has a higher relative value than electrode combination E((n/2)+1)(n/2), processor 40 determines that the electrode proximal to the proximal electrode of the middle electrode pair E((n/2)+1) is the electrode closest to the target tissue site (162). If processor 40 determines that electrode combination E(n/2)((n/2)−1) does not have a higher relative value than electrode combination E((n/2)+1)(n/2), processor 40 determines that the distal middle electrode E((n/2)−1) is the electrode closest to the target tissue site (164).

If processor 40 determines that the number of electrodes n is not even (158), processor 40 determines that the number of electrodes n of the lead is odd (166). Processor 40 then determines if the electrode combination comprising the middle electrode and the electrode adjacent and distal to the middle electrode, electrode combination E((n−1)/2)((n−1)/2−1), has a higher relative value than the electrode combination comprising the middle electrode and the electrode adjacent and proximal to the middle electrode, electrode combination E((n+1)/2)((n+1)/2)−1) (168). If processor 40 determines that electrode combination E((n−1)/2)((n−1)/2−1) has a value higher than E((n+1)/2)((n+1)/2)−1), processor 40 selects the middle electrode E((n−1)/2−1) as the electrode closest to the target tissue site (170). If processor 40 determines that electrode combination E((n−1)/2)((n−1)/2−1) does not have a higher relative value than electrode combination E((n+1)/2)((n+1)/2)−1), processor 40 selects the electrode adjacent and proximal to the middle electrode E((n+1)/2) as the electrode closest to the target tissue (172).

Figure 10:
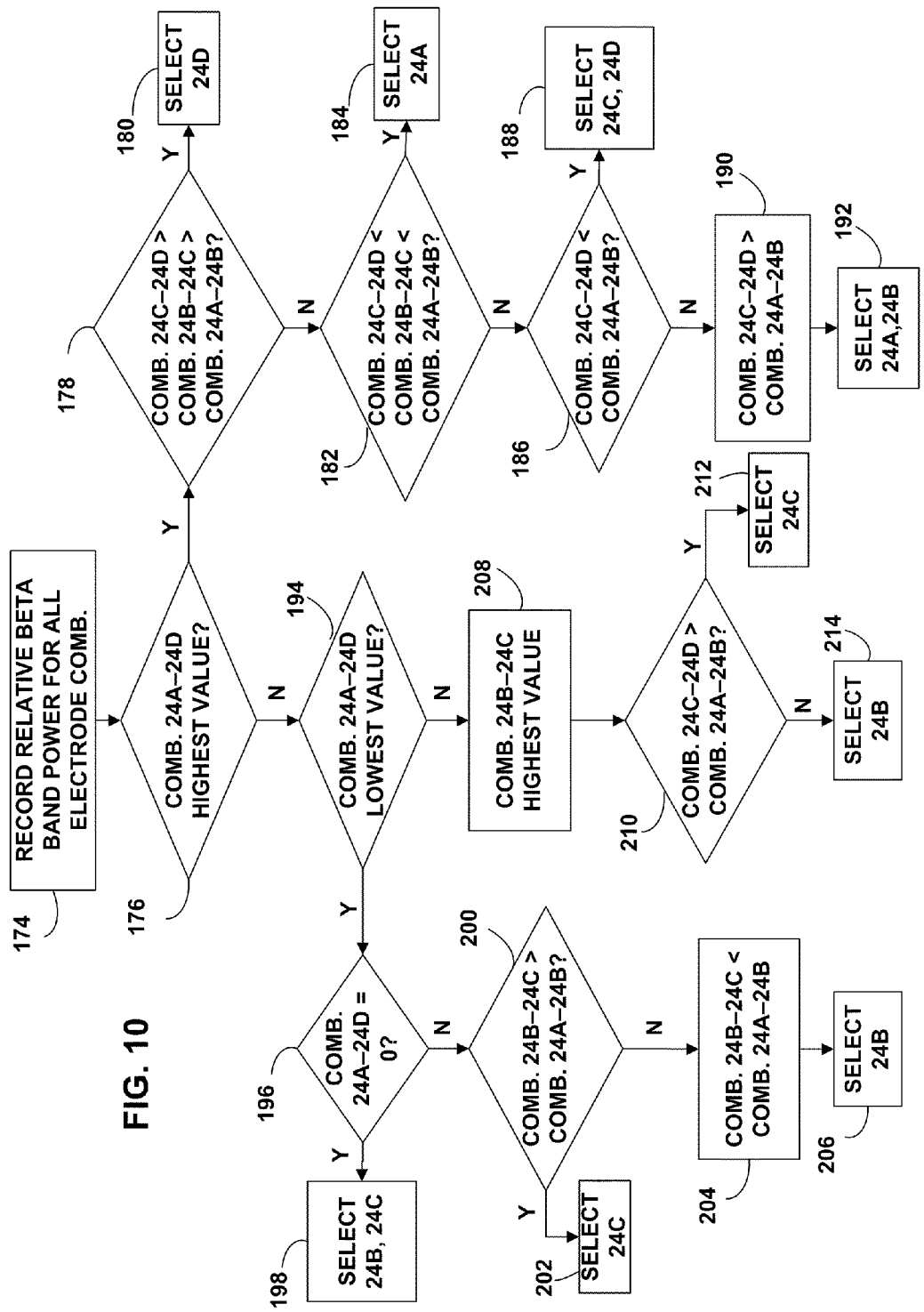
FIG. 10 is a flow diagram illustrating an algorithm that can be implemented to select electrodes that are closest to a target tissue site on a lead with four ring electrodes.

FIG. 10 is a flow diagram illustrating the general technique shown in FIGS. 9A-9C for determining which one or more sense electrodes are closest to a target tissue site as applied to a bipolar sensing technique with electrodes 24 of lead 20A

(FIG. 3). As with FIGS. 9A-9C, algorithm 60 may comprise instructions that cause processor 40 of IMD 16 to carry out each of the steps of the algorithm 60. However, in other examples, the process may be carried out by a different processor, such as processor 74 of programmer 14, with steps contained in a different algorithm.

Processor 40 determines the relative values of the relative beta band power level for each adjacent electrode combination and for the electrode combination comprising the most proximal and most distal electrodes is recorded (174). As described above, the relative beta band power level may be a ratio of the power in a beta band of the sensed signal to the overall power of the sensed signal and the relative value of the relative beta band power level is defined as the magnitude of the difference in amplitude between the relative beta band power levels sensed with each of two electrodes in an electrode combination in a unipolar configuration. Throughout the description, the electrode combination comprising electrodes 24A and 24B is referred to as 24A-24B, the electrode combination comprising electrodes 24B and 24C is referred to as 24B-24C, the electrode combination comprising electrodes 24C and 24D is referred to as 24C-24D, and the electrode combination comprising electrodes 24A and 24D is referred to as 24A-24D.

In accordance with the technique shown in FIG. 10, processor 40 determines whether electrode combination 24A-24D (i.e., the electrode combination comprising electrodes at each of the first and last positions along the longitudinal axis of lead 20A) has the highest relative value of the relative beta band power level values of all the electrode combinations (176). If electrode combination 24A-24D has the highest relative value, processor 40 determines whether electrode combination 24C-24D (i.e., the electrode combination comprising the most distal pair of adjacent electrodes of lead 20A) has a higher relative value than electrode combination 24B-24C and if electrode combination 24B-24C has a higher relative value than electrode combination 24A-24B (i.e., the electrode combination comprising the most proximal pair of adjacent electrodes of lead 20A) (178). If electrode combination 24C-24D has a higher relative value than electrode combination 24B-24C and electrode combination 24B-24C has a higher relative value than electrode combination 24A-24B, processor 40 selects electrode 24D (i.e., the most distal electrode of lead 20A) as the sense electrode closest to the target tissue site (180).

If, on the other hand, processor 40 determines that these criteria are not met, processor 40 determines whether electrode combination 24C-24D has a lower relative value than electrode combination 24B-24C and electrode combination 24B-24C has a lower relative value than electrode combination 24A-24B (182). If electrode combination 24C-24D has a lower relative value than electrode combination 24B-24C and electrode combination 24B-24C has a lower relative value than electrode combination 24A-24B, processor 40 selects electrode 24A (i.e., the most proximal electrode of lead 20A) as the sense electrode closest to the target tissue site (184). If, on the other hand, these criteria are not met, processor 40 determines whether electrode combination 24C-24D has a lower relative value than electrode combination 24A-24B (186). If electrode combination 24C-24D has a lower relative value than electrode combination 24A-24B, processor 40 determines that the target tissue site is closest to the midpoint between electrodes 24C and 24D on lead 20A, and selects electrodes 24C and 24D as being closest to the target tissue site (188).

If electrode combination 24C-24D does not have a lower relative value than electrode combination 24A-24B, processor 40 determines that electrode combination 24C-24D has a higher relative value than electrode combination 24A-24B (190). Processor 40 determines that the target tissue site is located closest to the midpoint between electrodes 24A and 24B on lead 20A and selects electrodes 24A and 24B as the sense electrodes closest to the target tissue site (192).

If processor 40 determines that electrode combination 24A-24D does not have the highest relative value (176), processor 40 determines whether electrode combination 24A-24D has the lowest relative value (194). If processor 40 determines that electrode combination 24A-24D has the lowest relative value, processor 40 then determines whether electrode combination 24A-24D has a relative value equal to zero (196). If electrode combination 24A-24D has a value equal to zero, processor 40 determines that the target tissue site is located closest to the midpoint between electrodes 24A and 24D of lead 20A, which is also the midpoint between electrodes 24B and 24C of lead 20A, and selects electrodes 24B and 24C as the sense electrodes closest to the target tissue site (198).

If processor 40 determines that electrode combination 24A-24D has a relative value that is not equal to zero, processor 40 determines whether electrode combination 24B-24C has a higher relative value than electrode combination 24A-24B (200). If electrode combination 24B-24C has a higher relative value than electrode combination 24A-24B, processor 40 selects electrode 24C as the sense electrode closest to the target tissue site (202). If electrode combination 24B-24C does not have a higher relative value than electrode combination 24A-24B, processor 40 determines that electrode combination 24B-24C has a lower relative value than electrode combination 24A-24B (204) and selects electrode 24B as the sense electrode closest to the target tissue site (206).

If processor 40 determines that electrode combination 24A-24D does not have the highest relative value or the lowest relative value (194), processor 40 determines that electrode combination 24B-24C has the highest relative value (208). Processor 40 then determines whether electrode combination 24C-24D has a higher relative value than electrode combination 24A-24B (210). If processor 40 determines that electrode combination 24C-24D has a higher relative value than electrode combination 24A-24B, processor 40 selects electrode 24C as the sense electrode closest to the target tissue site (212). If processor 40 determines that electrode combination 24C-24D does not have a higher relative value than electrode combination 24A-24B (210), processor 40 selects electrode 24B as the sense electrode closest to the target tissue site (214).

FIGS. 11A-11H, 12A-12E, and 13A-13B are graphs illustrating relative values of relative beta band power levels of each electrode combination of lead 20A (including electrodes 24A-24D) for each of a plurality of scenarios in which the target tissue site is located closest to different electrodes. The graphs were generated using Microsoft Office Excel, made commercially available by Microsoft Corporation of Redmond, Wash. The target tissue site was modeled as a point source and the extracellular electrical potentials sensed by each of the sense electrodes were determined using the following equation:

$$Ve = \frac{Isrc}{4\pi\sigma r}$$

where Ve is the extracellular potential, Isrc (Isource) is the magnitude of the modeled point source, σ is the conductivity of the extracellular medium tissue and r is the distance between the point source and the recording site. In this case, σ was modeled as 0.23 Siemens per meter and r was modeled as 1 millimeter from a longitudinal axis of a lead on which the electrodes are positioned. The electrical potentials (e.g., which can be representative of bioelectrical brain signals) were sensed at four locations along a linear lead. Three millimeter spacing between each location was used to model the spacing between electrodes on one type of commonly-used linear lead, which includes multiple electrodes with three millimeter spacing between each. In other examples, electrodes may have different spacing, e.g., two millimeters.

Figure 11A:
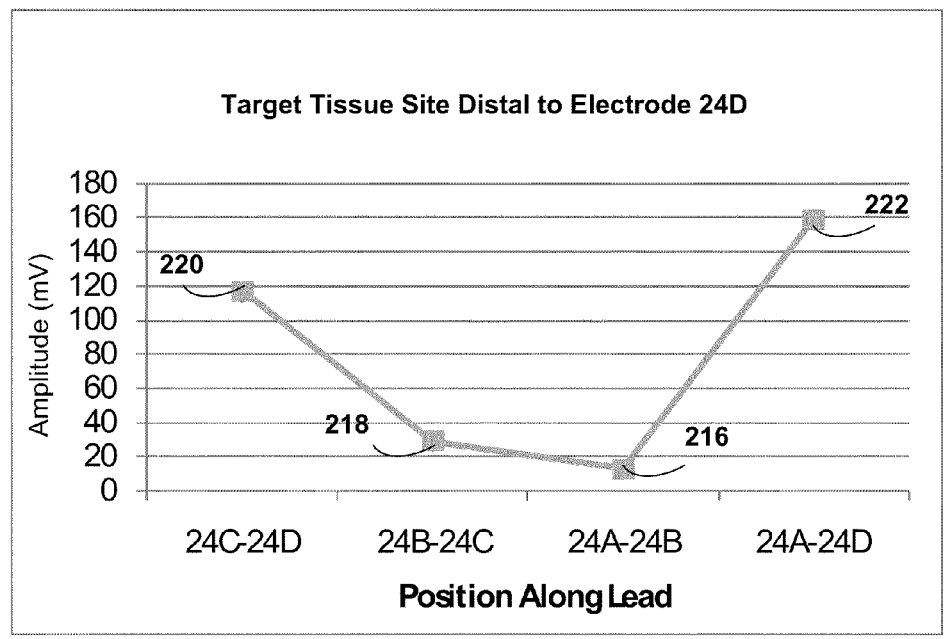
FIGS. 11A-11H, 12A-12E, and 13A-13B are graphs illustrating the relative values of beta band power levels for electrode combinations when a target tissue site is located closest to different electrodes along a lead with four ring electrodes.

FIG. 11A-11H represent scenarios in which electrode combination 24A-24D has the greatest relative value of the relative beta band power level, which correspond to the technique associated with blocks 178-192 in FIG. 10. FIGS. 11A-11H each illustrate the relative values of the relative beta band power level for a plurality of electrode combinations, whereby the relative value of the relative beta band power level indicates the absolute difference in a beta band power level of a first bioelectrical brain signal sensed with a first electrode in a unipolar configuration and a beta band power level of a second bioelectrical brain signal sensed with a second electrode 24D in a unipolar configuration. For example, FIG. 11A illustrates a scenario in which electrode combination 24A-24B has a relative value 216 of approximately 12.9243 milliVolts (mV), electrode combination 24B-24C has a relative value 218 of approximately 29.3284 mV, electrode combination 24C-24D has a relative value 220 of approximately 116.865 mV, and electrode combination 24A-24D has a relative value 222 of approximately 159.117 mV. Because relative value 220 is greater than relative value 218 and relative value 218 is greater than relative value 216, processor 40, when implementing algorithm 60, determines that the target tissue site is closest to electrode 24D compared to electrodes 24A-24C, as shown in steps 178 and 180 of FIG. 10.

Figure 11B:
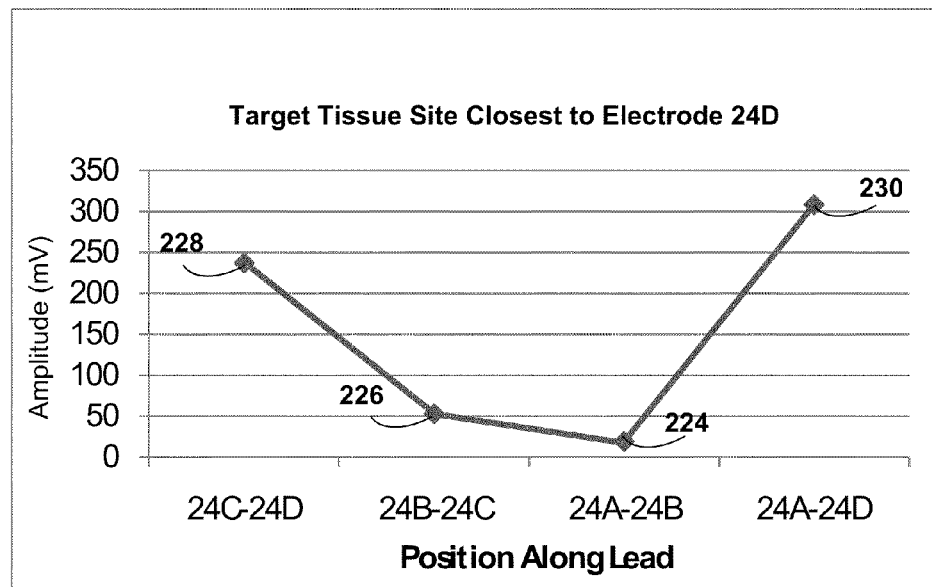

FIG. 11B illustrates a scenario in which electrode combination 24A-24B has a relative value 224 of approximately 18.6721 milliVolts (mV), electrode combination 24B-24C has a relative value 226 of approximately 52.5311 mV, electrode combination 24C-24D has a relative value 228 of approximately 236.578 mV, and electrode combination 24A-24D has a relative value 230 of approximately 307.781 mV. Because relative value 228 is greater than relative value 226 and relative value 226 is greater than relative value 224, processor 40, when implementing algorithm 60, determines that the target tissue site is closest to electrode 24D, as shown in steps 178 and 180 of FIG. 10.

Figure 11C:
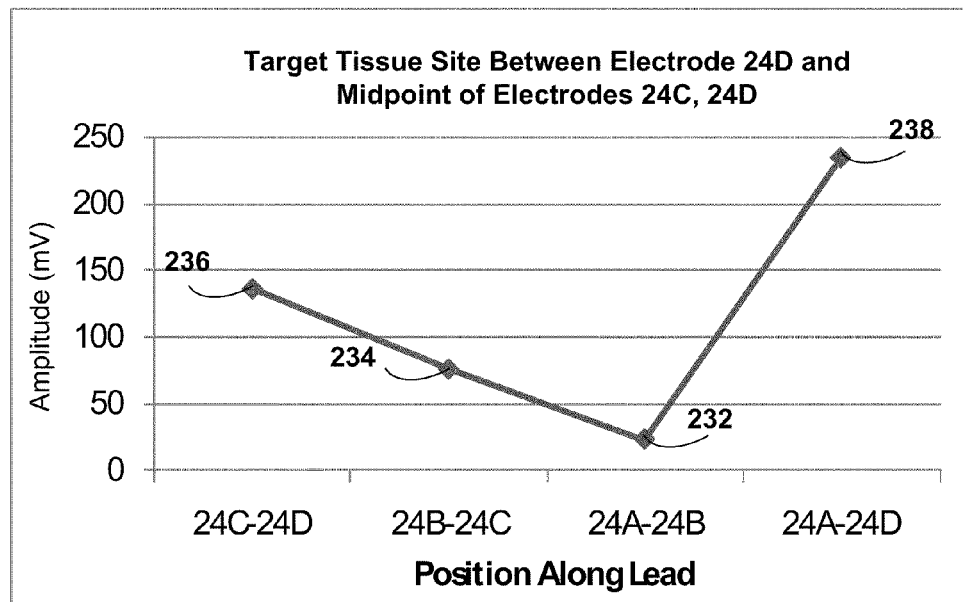

FIG. 11C illustrates a scenario in which electrode combination 24A-24B has a relative value 232 of approximately 23.1054 milliVolts (mV), electrode combination 24B-24C has a relative value 234 of approximately 75.7807 mV, electrode combination 24C-24D has a relative value 236 of approximately 136.272 mV, and electrode combination 24A-24D has a relative value 238 of approximately 235.158 mV. Because relative value 236 is greater than relative value 234 and relative value 234 is greater than relative value 232, processor 40, when implementing algorithm 60, determines that the target tissue site is closest to electrode 24D, as shown in steps 178 and 180 of FIG. 10. More specifically, the target tissue site is between electrode 24D and the midpoint of electrodes 24C and 24D.

Figure 11D:
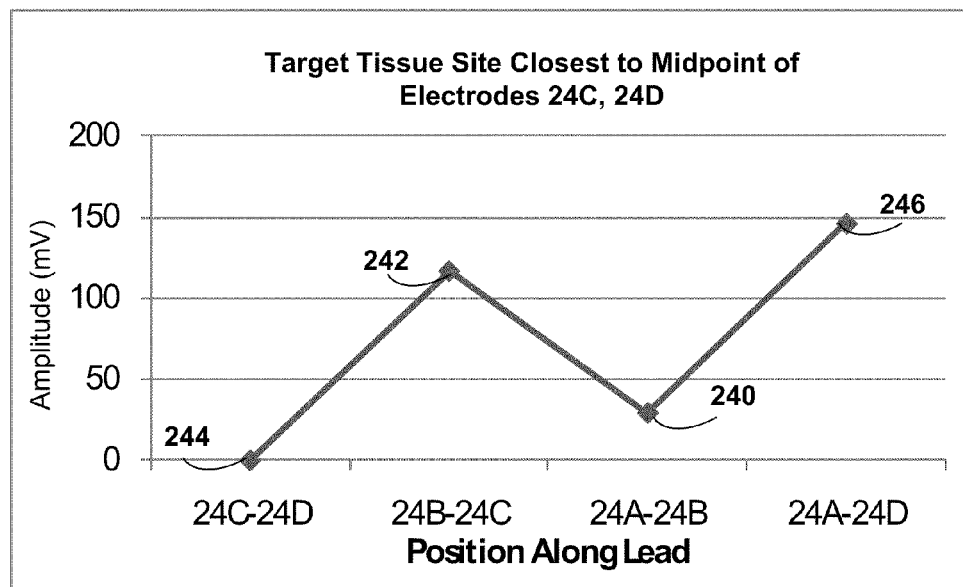

FIG. 11D illustrates a scenario in which electrode combination 24A-24B has a relative value 240 of approximately 29.3284 milliVolts (mV), electrode combination 24B-24C has a relative value 242 of approximately 116.865 mV, electrode combination 24C-24D has a relative value 244 of 0 mV, and electrode combination 24A-24D has a relative value 246 of approximately 146.193 mV. In this scenario, relative value 244 is not greater than relative value 242, so the criteria associated with block 178 of the technique shown in FIG. 10 are not met. Also, relative value 242 is not less than relative value 240, so the criteria associated with block 182 of the technique shown in FIG. 10 are not met. However, because relative value 244 is less than relative value 240, processor 40 selects electrodes 24C and 24D as closest to the target tissue site in step 188. Specifically, the target tissue site is closest to the midpoint between electrodes 24C and 24D.

Figure 11E:
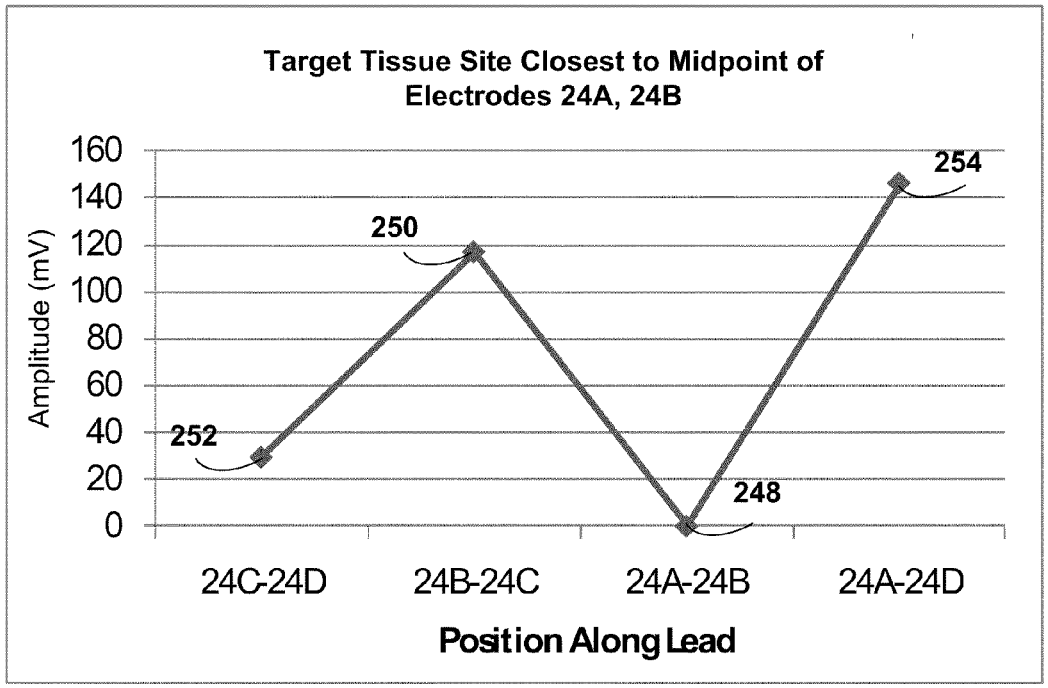

FIG. 11E illustrates a scenario in which electrode combination 24A-24B has a relative value 248 of 0 milliVolts (mV), electrode combination 24B-24C has a relative value 250 of approximately 116.865 mV, electrode combination 24C-24D has a relative value 252 of approximately 29.3284 mV, and electrode combination 24A-24D has a relative value 254 of approximately 146.193 mV. In this scenario, relative value 252 is not greater than relative value 250, so the criteria associated with block step 178 of the technique shown in FIG. 10 are not met. Also, relative value 250 is not less than relative value 248, so the criteria associated with block 182 of the technique shown in FIG. 10 are not met. Additionally, relative value 252 is not less than relative value 248, so the criteria of step 186 are not met. However, relative value 252 is greater than relative value 248 and processor 40 selects electrodes 24A and 24B as closest to the target tissue site in step 188. Specifically, processor 40 determines that, based on algorithm 60, the target tissue site (e.g., associated with high beta band activity) is closest to the midpoint between electrodes 24A and 24B.

Figure 11F:
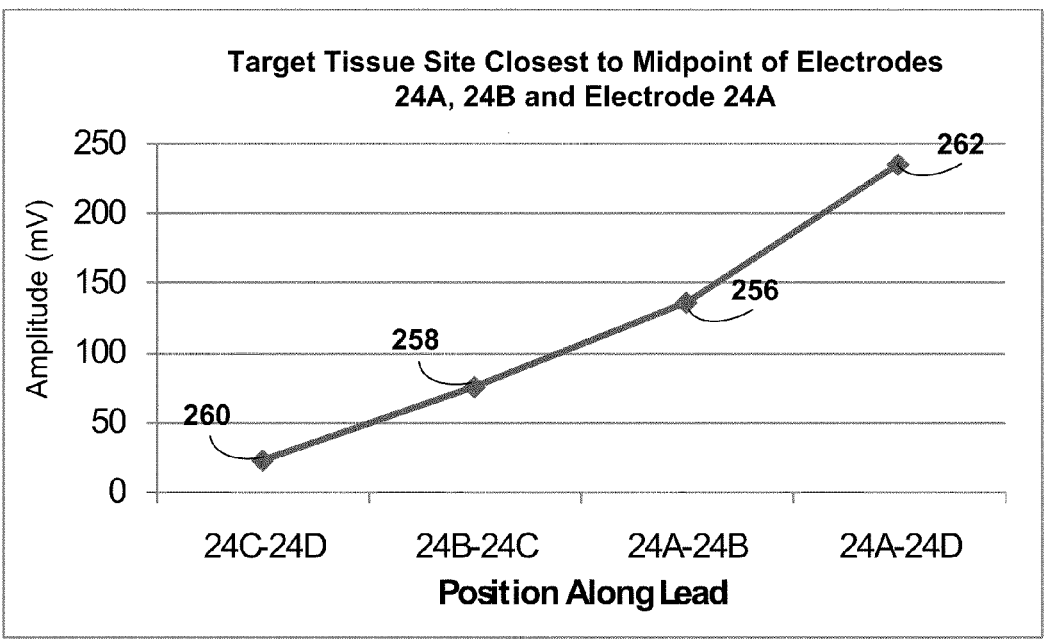

FIG. 11F illustrates a scenario in which electrode combination 24A-24B has a relative value 256 of approximately 136.272 milliVolts (mV), electrode combination 24B-24C has a relative value 258 of approximately 75.7807 mV, electrode combination 24C-24D has a relative value 260 of approximately 23.1054 mV, and electrode combination 24A-24D has a relative value 262 of approximately 235.158 mV. In this scenario, relative value 260 is not greater than relative value 258, so the criteria associated with block 178 of the technique shown in FIG. 10 are not met. However, relative value 260 is less than relative value 258 and relative value 258 is less than relative value 256, so the criteria associated with block 182 of the technique shown in FIG. 10 are met and processor 40 selects electrode 24A as closest to the target tissue site. Specifically, processor 40 determines, based on algorithm 60, that the target tissue site is closest to the midpoint of electrodes 24A and 24B and electrode 24A.

Figure 11G:
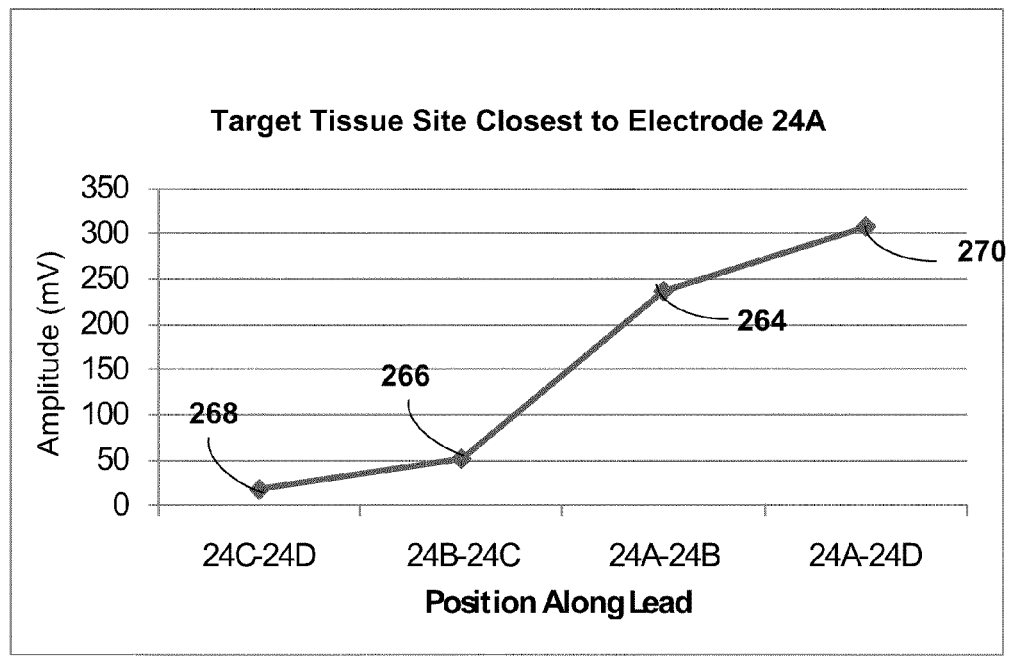

FIG. 11G illustrates a scenario in which electrode combination 24A-24B has a relative value 264 of approximately 236.578 milliVolts (mV), electrode combination 24B-24C has a relative value 266 of approximately 52.5311 mV, electrode combination 24C-24D has a relative value 268 of approximately 18.6721 mV, and electrode combination 24A-24D has a relative value 270 of approximately 307.781 mV. In this scenario, relative value 268 is not greater than relative value 266 and relative value 266 is not greater than relative value 264, so the criteria associated with block 178 of the technique shown in FIG. 10 are not met. However, relative value 268 is less than relative value 266 and relative value 266 is less than relative value 264, so the criteria associated with block 182 are met, and, as a result, processor 40 selects electrode 24A as being the sense electrode closest to the target tissue site.

Figure 11H:
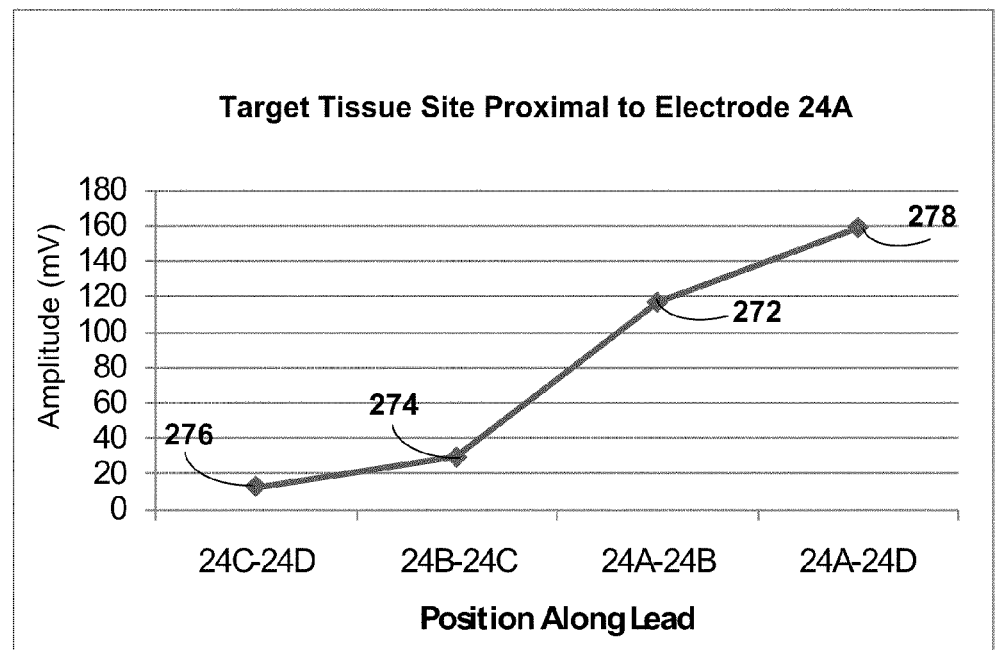

FIG. 11H illustrates a scenario in which electrode combination 24A-24B has a relative value 272 of approximately 116.865 milliVolts (mV), electrode combination 24B-24C has a relative value 274 of approximately 29.3284 mV, electrode combination 24C-24D has a relative value 276 of approximately 12.9243 mV, and electrode combination 24A-24D has a relative value 278 of approximately 159.117 mV. In this scenario, relative value 276 is not greater than relative value 274 and relative value 274 is not greater than relative value 272, so the criteria associated with block 178 of the technique shown in FIG. 10 are not met. However, relative value 276 is less than relative value 274 and relative value 274 is less than relative value 272, so the criteria associated with block 182 of the technique shown in FIG. 10 are met and processor 40 selects electrode 24A as closest to the target tissue site. Specifically, processor 40 determines that, based on execution of algorithm 60, the target tissue site is located proximal to electrode 24A.

Figure 12A:
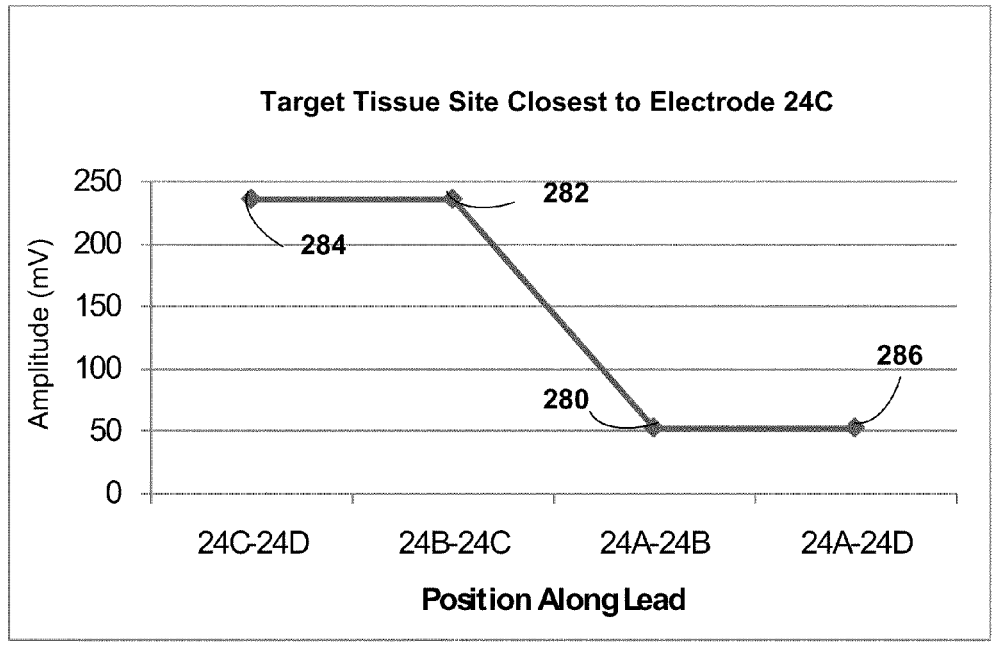

FIG. 12A-12E are graphs illustrating the relative beta band power levels in scenarios in which electrode combination 24A-24D has the lowest relative value of the relative beta band power level, which correspond to blocks 196-206 in the technique shown in FIG. 10. For example, FIG. 12A illustrates a scenario in which electrode combination 24A-24B has a relative value 280 of approximately 52.311 milliVolts (mV), electrode combination 24B-24C has a relative value 282 of approximately 236.578 mV, electrode combination 24C-24D has a relative value 284 of approximately 236.578 mV, and electrode combination 24A-24D has a relative value 286 of approximately 52.5311 mV. Because relative value 286 is not equal to zero, the criteria associated with block 196 (FIG. 10) is not satisfied. However, relative value 282 is greater than relative value 280, so processor 40 selects electrode 24C as being the electrode closest to the target tissue site.

Figure 12B:
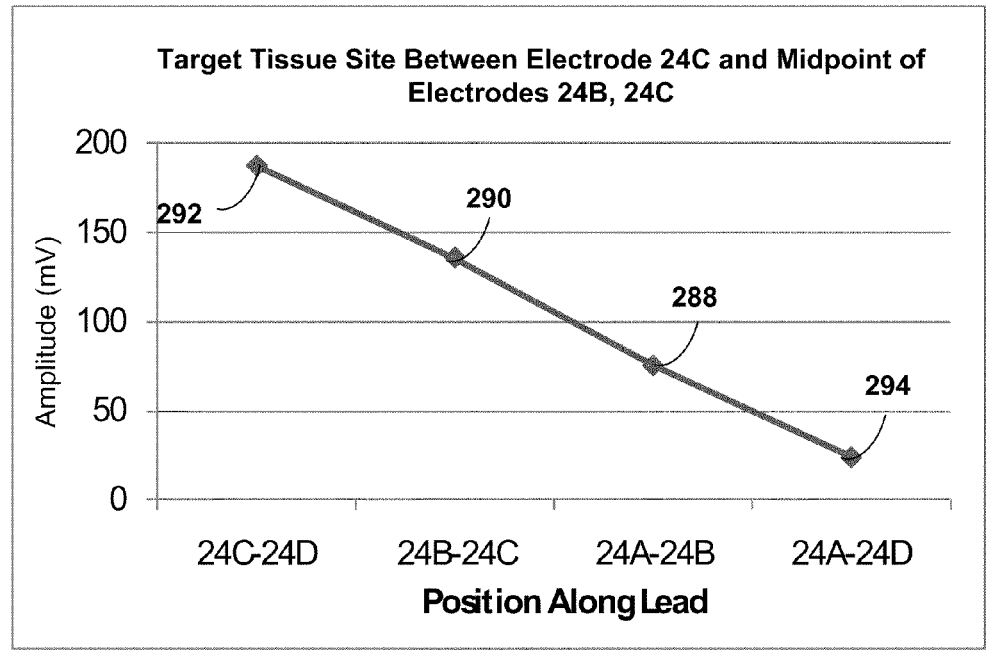

FIG. 12B illustrates a scenario in which electrode combination 24A-24B has a relative value 288 of approximately 75.7807 milliVolts (mV), electrode combination 24B-24C has a relative value 290 of approximately 136.272 mV, electrode combination 24C-24D has a relative value 292 of approximately 187.643 mV, and electrode combination 24A-24D has a relative value 294 of approximately 24.4097 mV. Because relative value 294 is not equal to zero, the criteria associated with block 196 in the technique shown in FIG. 10 is not satisfied. Because relative value 290 is greater than relative value 288, processor 40 selects electrode 24C as being the electrode closest to the target tissue site. Specifically, the results of implementing algorithm 60 indicate that the target tissue site is between electrode 24C and the midpoint of electrodes 24B and 24C.

Figure 12C:
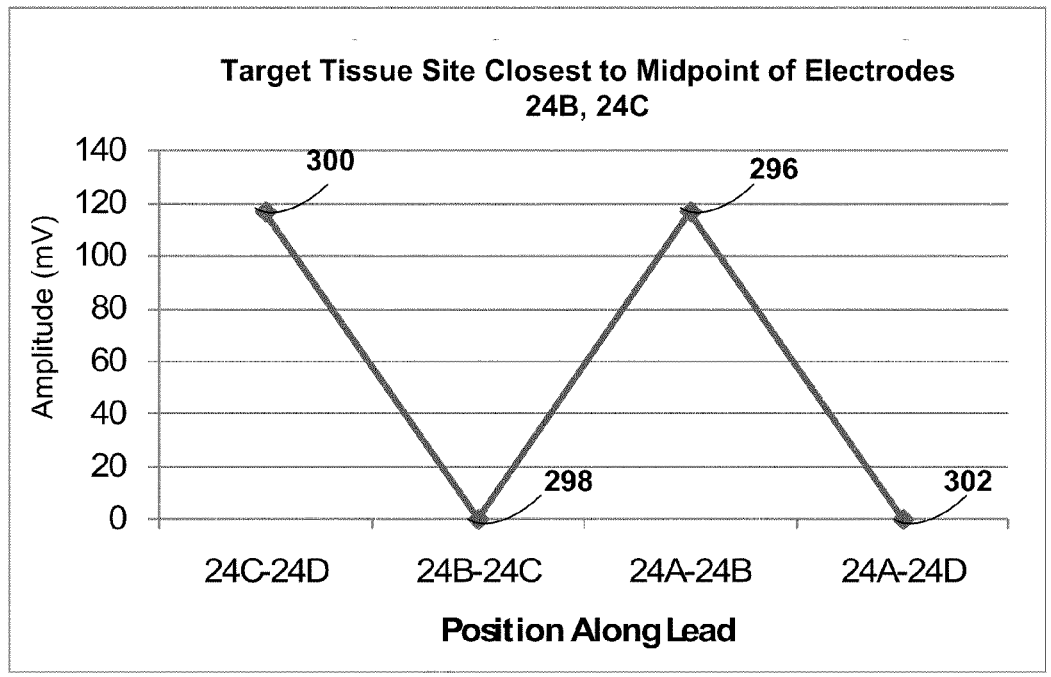

FIG. 12C illustrates a scenario in which electrode combination 24A-24B has a relative value 296 of approximately 116.865 milliVolts (mV), electrode combination 24B-24C has a relative value 298 of approximately 0 mV, electrode combination 24C-24D has a relative value 300 of approximately 116.865, and electrode combination 24A-24D has a relative value 302 of approximately 0 mV. Because amplitude 302 of the relative beta band power level of a signal sensed with electrodes 24A and 24D has a value of approximately zero, the criteria at associated with block 196 of the technique shown in FIG. 10 is satisfied. As previously indicated, amplitude 302 also indicates the relative value of the relative beta band powers of the bioelectrical signals sensed in a unipolar configuration with each of the electrodes 24A, 24D. As a result, processor 40 selects electrodes 24B and 24C as being closest to the target tissue site.

Figure 12D:
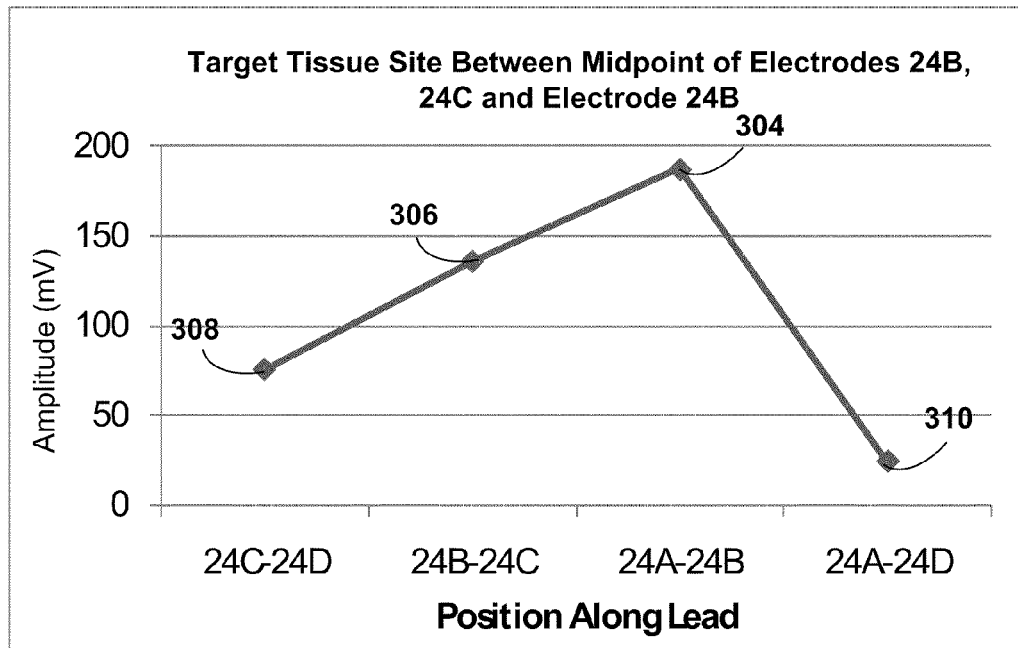

FIG. 12D illustrates a scenario in which a relative value 304 indicating a magnitude of a difference between the beta band power level of bioelectrical brain signals sensed via electrodes 24A and 24B has is approximately 187.643 milliVolts (mV), electrode combination 24B-24C has a relative value 306 of approximately 136.272 mV, electrode combination 24C-24D has a relative value 308 of approximately 75.7807 mV, and electrode combination 24A-24D has a relative value 310 of approximately 24.4097 mV. Because relative value 310 is not equal to zero, the criteria associated with block 196 of the technique shown in FIG. 10 is not satisfied. In addition, because relative value 306 is not greater than relative value 304, the criteria associated with block 200 of the technique shown in FIG. 10 are not satisfied. Thus, because relative value 306 is less than relative value 304, processor 40, while implementing algorithm 60, selects electrode 24B as the electrode closest to the target tissue site. Specifically, processor 40, while implementing algorithm 60, determines that the target tissue site is between the midpoint of electrodes 24B and 24C and electrode 24B.

Figure 12E:
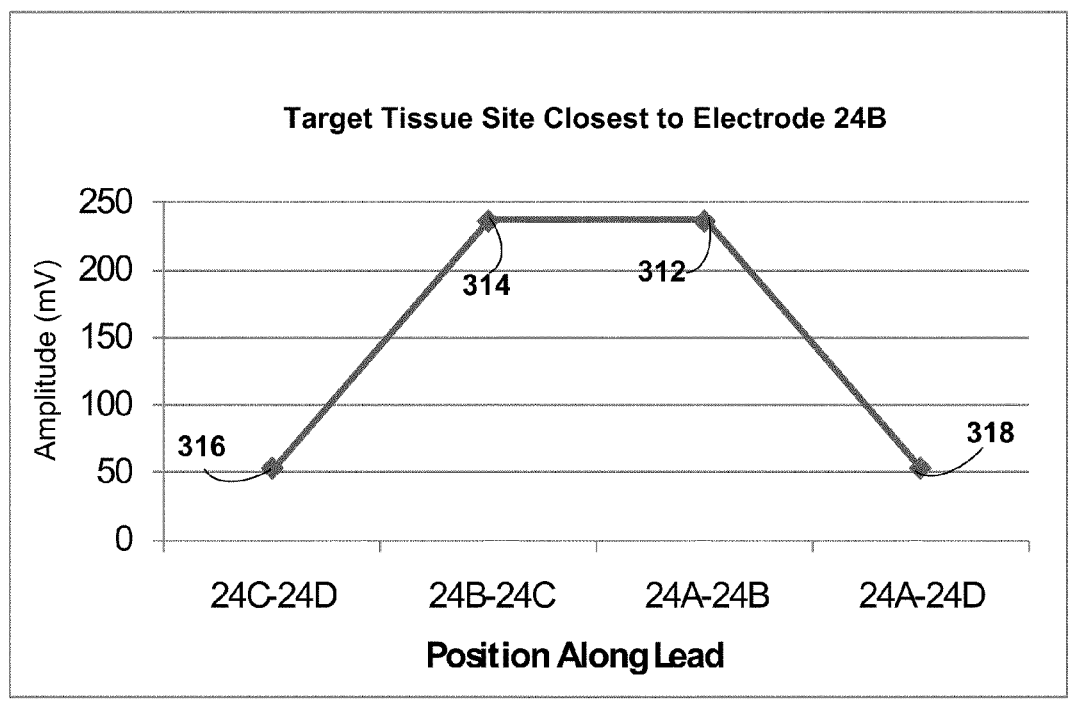

FIG. 12E illustrates a scenario in which the target tissue site is closest to electrode 24B. Electrode combination 24A-24B has a relative value 312 of approximately 236.578 milliVolts (mV), electrode combination 24B-24C has a relative value 314 of approximately 236.578 mV, electrode combination 24C-24D has a relative value 316 of approximately 52.5311 mV, and electrode combination 24A-24D has a relative value 318 of approximately 52.5311 mV. Because relative value 318 is not equal to zero and relative value 314 is not greater than relative value 312, processor 40 selects electrode 24B as being as closest to the target tissue site.

Figure 13A:
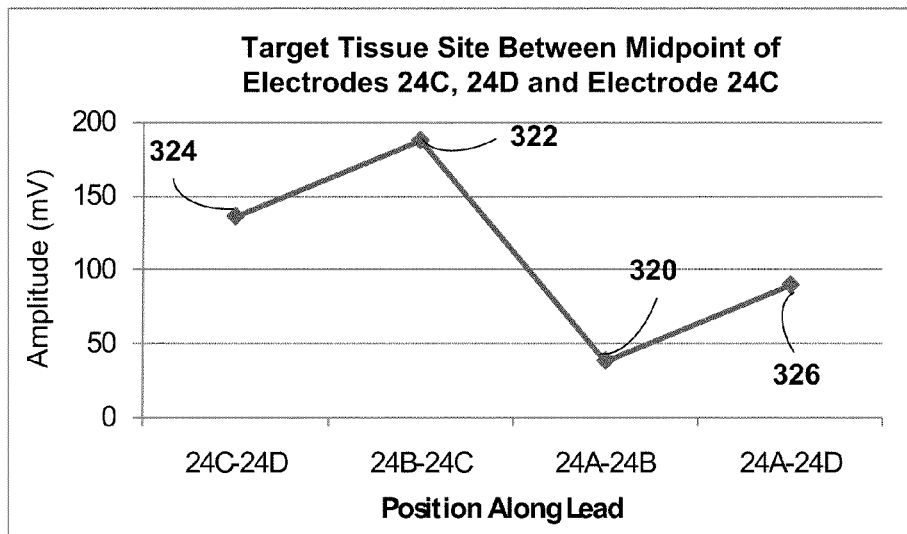
Figure 13B:
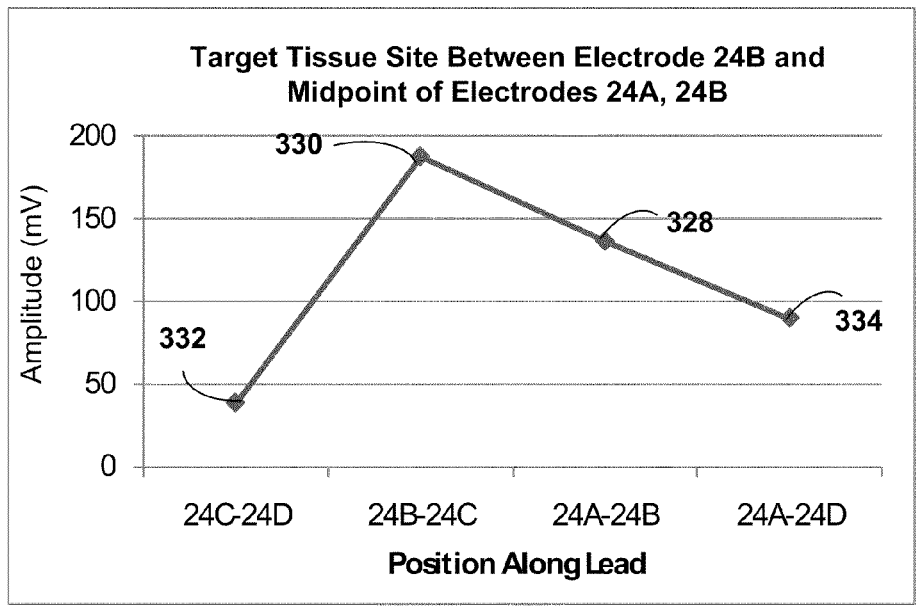

FIGS. 13A and 13B are graphs illustrating scenarios in which electrode combination 24A-24D has neither the lowest relative value nor the highest relative value and in which electrode combination 24B-24C has the highest relative value, which correspond to blocks 208-214 in FIG. 10. For example, FIG. 13A illustrates a scenario in which electrode combination 24A-24B has a relative value 320 of approximately 38.442 milliVolts (mV), electrode combination 24B-24C has a relative value 322 of approximately 187.643 mV, electrode combination 24C-24D has a relative value 324 of approximately 136.272 mV, and electrode combination 24A-24D has a relative value 326 of approximately 89.8152 mV. Because relative value 324 is greater than relative value 320, processor 40 selects electrode 24C as closest to the target tissue site. Specifically, the target tissue site is between the midpoint of electrodes 24C and 24D and electrode 24C.

FIG. 13B illustrates a scenario in which processor 40 determines that the target tissue site is between electrode 24B and a midpoint between electrodes 24A and 24B. In the example shown in FIG. 13B, electrode combination 24A-24B has a relative value 328 of approximately 136.272 milliVolts (mV), electrode combination 24B-24C has a relative value 330 of approximately 187.643 mV, electrode combination 24C-24D has a relative value 332 of approximately 28.4442 mV, and electrode combination 24A-24D has a relative value 334 of approximately 89.8152 mV. Because relative value 332 is not greater than relative value 328, processor 40 selects electrode 24C as being closest to the target tissue site. Specifically, processor 40 determines that, while implementing algorithm 60, the target tissue site is between electrode 24B and the midpoint of electrodes 24A and 24B.

Figure 14:
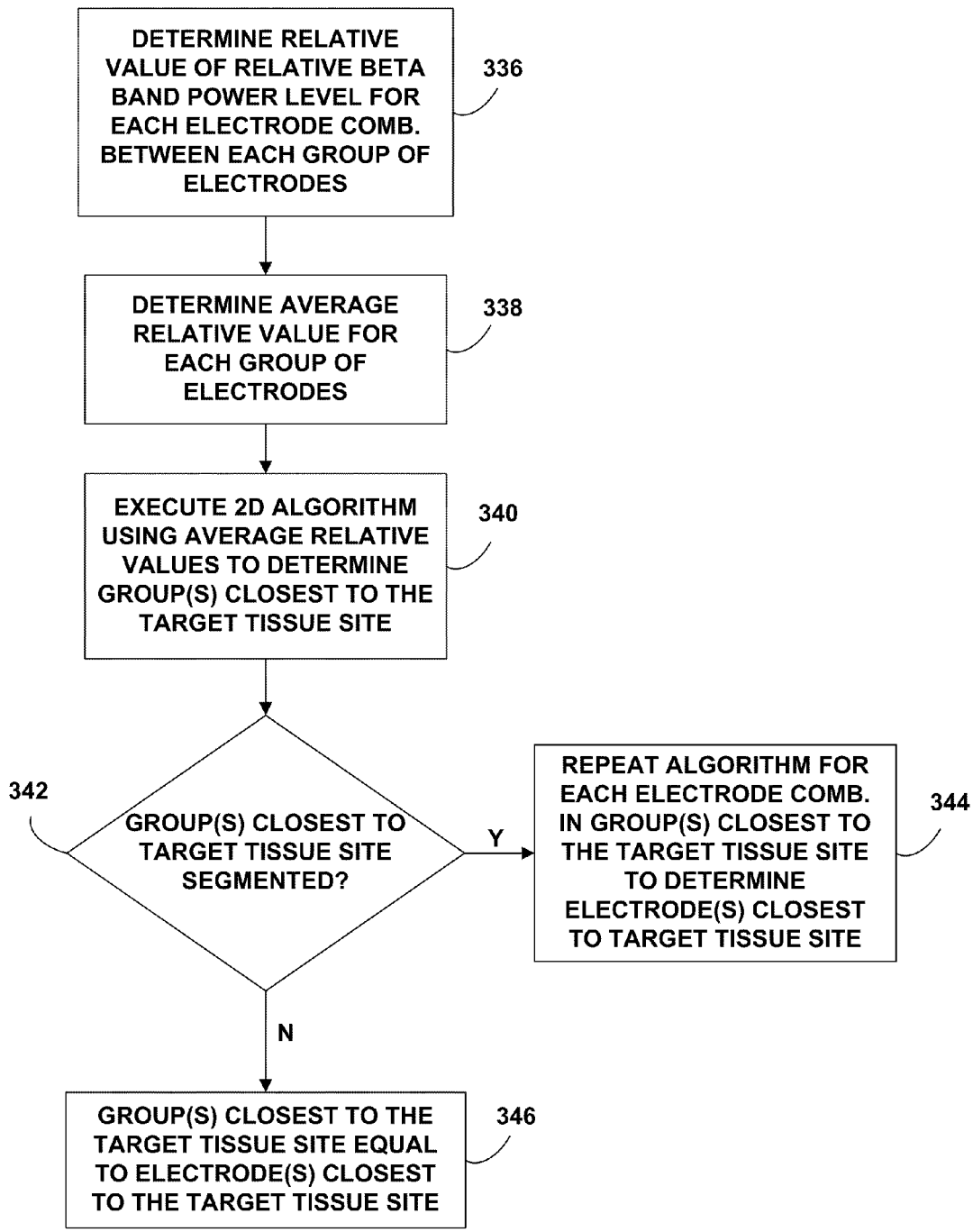
FIG. 14 is a flow diagram illustrating an example technique for determining the electrode or electrodes closest to a target tissue site for a lead comprising groups of segmented electrodes.

FIG. 14 is a flow diagram illustrating an example technique for determining which electrode or electrodes are closest to a target tissue site for a lead comprising groups of segmented electrodes, such as lead 62 (FIGS. 4A, 4B). In this example, the technique is described with respect to lead 62 which comprises groups of electrodes 64 including groups of segmented electrodes 68 and 70. In other examples, however, the technique may be applicable to a lead with any combination and configuration of groups of ring electrodes and segmented electrodes. As with FIGS. 9A-9C and 10, algorithm 60 may include instructions that cause processor 40 to carry out each of the steps of the technique illustrated in FIG. 14. However, in other examples, the technique may be carried out by a different processor, such as processor 74 of programmer 14.

In general, FIG. 14 illustrates a technique that may provide a more robust indication of the location of the target tissue site within brain 28 than the techniques illustrated in FIGS. 9A-B and 10. For example, in addition to determining the position of the target tissue site along the longitudinal axis of a lead, the technique illustrated in FIG. 14 includes determining the location of a target tissue site relative to a side of lead 62 (e.g., as indicated by a direction nonparallel to a longitudinal axis of lead 62, such as a direction substantially perpendicular to the longitudinal axis). Determining the position of the target tissue site in a first direction, as indicated by the longitudinal axis of the lead, and subsequently in a second direction, as indicated by a direction in which the segmented electrodes are displaced from one another, may provide additional information about the target tissue site location, facilitating selection of a stimulation electrode combination that provides more efficacious therapy to patient 12.

Processor 40 determines the relative values of the relative beta band power level for each electrode combination between each group of electrodes (336). Specifically, processor 40 determines the relative values for each of electrode combinations 72-70A, 72-70B, 72-70C, 70A-68A, 70B-68B, 70C-68C, 68A-66, 68B-66, 68C-66, and 72-66. Processor determines an average relative value for each group of electrodes (338). In order to determine the average value for group of electrode combinations including electrodes 72-70, i.e., comprised of the most distal group electrodes, processor 40 determines the average of the relative values for electrode combinations 72-70A, 72-70B, and 72-70C. In order to determine the average relative value for group of electrode combinations 70-68, i.e., the middle groups of electrodes, processor 40 determines the average of the relative values for electrode combinations 70A-68A, 70B-68B, and 70C-68C. In order to determine the average relative value for group of electrode combinations 68-66, i.e., the most proximal groups of electrodes, processor 40 determines the average of the relative values for electrode combinations 68A-66, 68B-66, and 68C-66. Processor 40 may not determine an average relative value for electrode combination 72-66, i.e., the most proximal and most distal groups of electrodes, because groups of electrodes 72 and 66 each comprise only one ring electrode.

Next, processor 40 executes algorithm 60 to determine the group or groups (i.e., 66, 68, 70, and 72) of electrodes closest to the target tissue site (340). The process is similar to that shown in FIG. 10, except that processor 40 compares the average relative values for combinations of groups of electrodes 72-70, 70-68, and 68-66 and the relative value for combination 72-66 instead of the relative values for each electrode combination. Once processor 40 has selected the group or groups of electrodes closest to the target tissue site based on algorithm 60, processor 40 determines whether the selected group or groups comprise a segmented array of electrodes, i.e., groups 68 or 70 (342). If processor 40 determines that the selected group or groups determined be closest to the target tissue site comprises a segmented array of electrodes, processor 40 executes algorithm 60 for each electrode in the selected group or groups of electrodes to select the specific electrode that is closest to the target tissue site (344). For example, if processor 40 determines that group of electrodes 68 is closest to the target tissue site, processor 40 determines the relative values for the relative beta band power levels of the electrode combinations 68A-68B, 68B-68C, and 68C-68A of the group. Processor 40 then determines which of electrodes 68A, 68B, and 68C are closest to the target tissue site based on the relative values. The determination of which of the electrodes 68A, 68B, and 68C of the group of segmented electrodes sharing a position along a longitudinal axis of the lead is closest to the target tissue site determines the location of the target tissue site in a different direction relative to the first determination for determining which group of electrodes is closest to the target tissue site. For example, determining which group of electrodes is closest to the target tissue site includes determining which position along the longitudinal axis of lead 62 is closest to the target tissue site. Determining which of electrodes 68A, 68B, and 68C is closest to the target tissue site may include determining which position around the perimeter of lead 62 at the longitudinal position of electrodes 68 is closest to the target tissue site. Determining the position of the target tissue site in two directions, e.g., the longitudinal position and the position around the perimeter, may provide a more robust indication of the position of the target tissue site along lead 62 than determining the position of the target tissue site in only one direction.

If, on the other hand, processor 40 determines that the selected group or groups of electrodes do not comprise segmented electrodes, processor 40 determines that the electrode closest to the target tissue site is the group or groups closest to the target tissue site (346). For example, if processor 40 selects group of electrodes 72 as closest to the target tissue site, processor 40 consequently selects electrode 72 as the electrode closest to the target tissue site because group of electrodes 72 comprises only electrode 72.

FIGS. 15A, 15B, 16A, 16B, 17A, 17B, 18A, 18B, 19A, and 19B illustrate graphs of values for the relative beta band power levels of electrode combinations and groups of electrodes 66, 68, 70, and 72 of lead 62 (FIGS. 4A and 4B). As shown in FIGS. 4A and 4B, electrodes 66 and 72 are ring electrodes and electrodes 68 and 70 each comprise three segmented electrodes. FIGS. 15A, 16A, 17A, 18A, and 19A each illustrate the relative values for each electrode combination within groups of electrodes 66, 68, 70, and 72. FIGS. 15B, 16B, 17B, 18B, and 19B illustrate the average relative values for the groups of electrodes that are used to select the group of electrodes closest to the target tissue site.

Figure 15A:
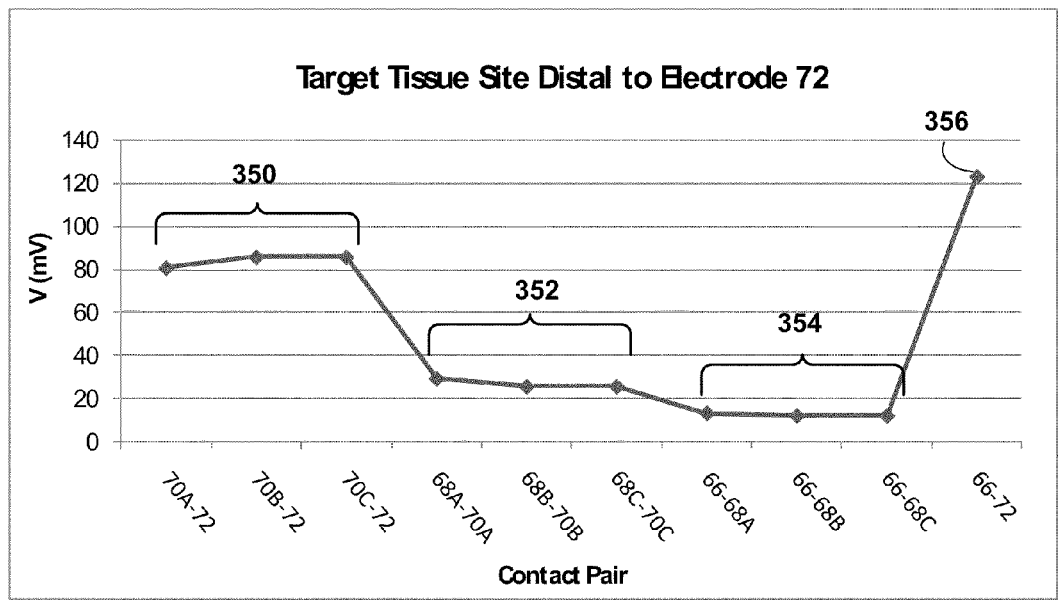
FIGS. 15A-15B, 16A-16B, 17A-17B, 18A-18B, 19A-19B, and 20A-20E are graphs illustrating the relative values of beta band power levels for electrode combinations when a target tissue site is located closest to different electrodes along a lead with two groups of ring electrodes and two groups of segmented electrodes.

FIG. 15A illustrates relative values 350 for each electrode combination 70A-72, 70B-72, and 70C-72 in a first group of electrode combinations, relative values 352 for each electrode combination 68A-70A, 68B-70B, and 68C-70C in a second group of electrode combinations, relative values 354 for each electrode combination 66-68A, 66-68B, and 66-68C in a third group of electrode combinations, and relative value 356 for the electrode combination 66-72 in a fourth group of electrode combinations. The first, second, third, and fourth group of electrode combinations are distributed along a longitudinal axis of lead 62, such that no two groups of electrode combinations have a common axial position (e.g., a position along the longitudinal axis of lead 62).

Figure 15B:
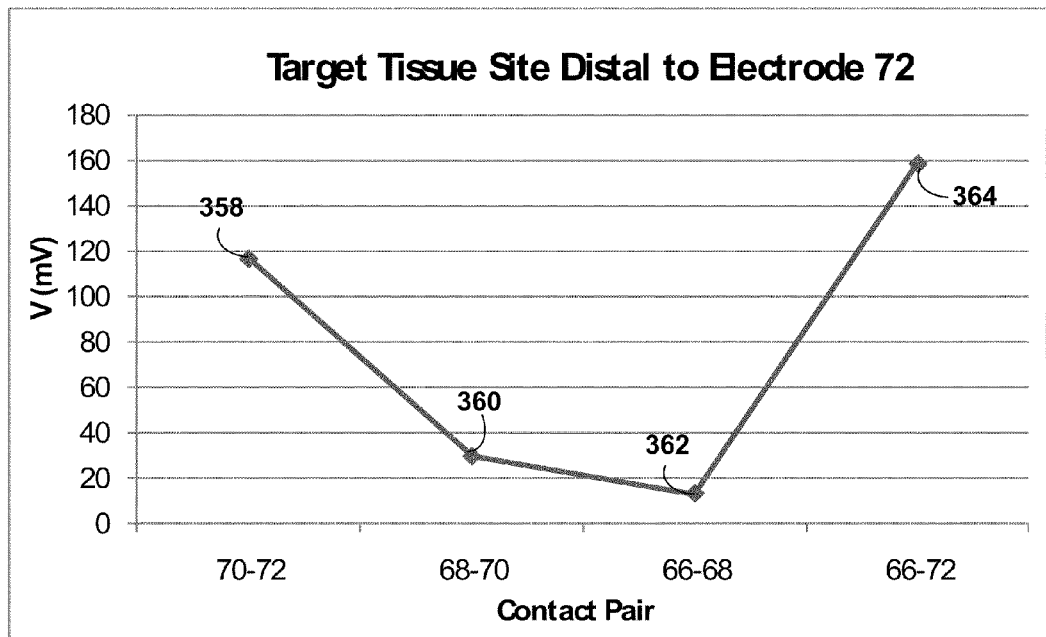

As described above with respect to FIG. 14, the relative values for each of the electrode combinations are determined and the average relative value for each group of electrodes is determined based on the relative values for each of the electrode combinations in the group in order to determine the group of electrodes closest to the target tissue site. Thus, FIG. 15B illustrates the average relative values 358, 360, and 362 determined from relative values 350, 352, and 354. For example, average relative value 358 is determined by determining the average value of relative values 350, e.g., the average of the relative values for each of electrode combinations 70A-72, 70B-72, and 70C-72 in the example shown in FIG. 15A. Relative value 364 is equal to relative value 356 because electrode combination 66-72 comprises two ring electrodes and no groups of segmented electrodes. An algorithm, such as algorithm 60 described above with respect to FIG. 10, may then be used to determine the group of electrodes that is closest to the target tissue site based on the average relative values 358, 360, and 362 and the relative value 364. In the example shown in FIGS. 15A and 15B, processor 40 of IMD 16 determines that group of electrodes 72 is closest to the target tissue site. Specifically, algorithm 60 indicates that the target tissue site is distal to group of electrodes 72.

Figure 16A:
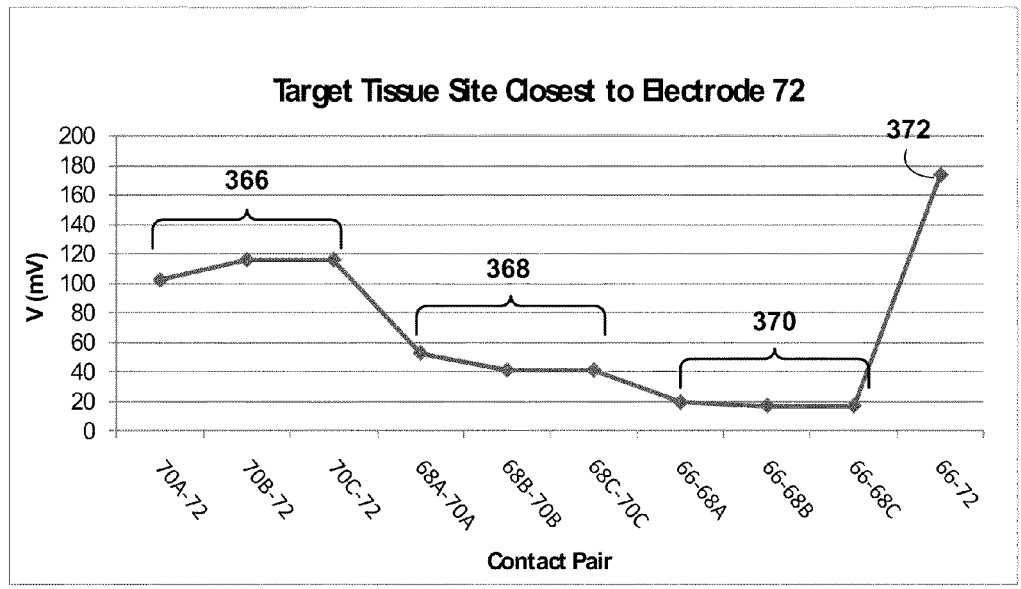
Figure 16B:
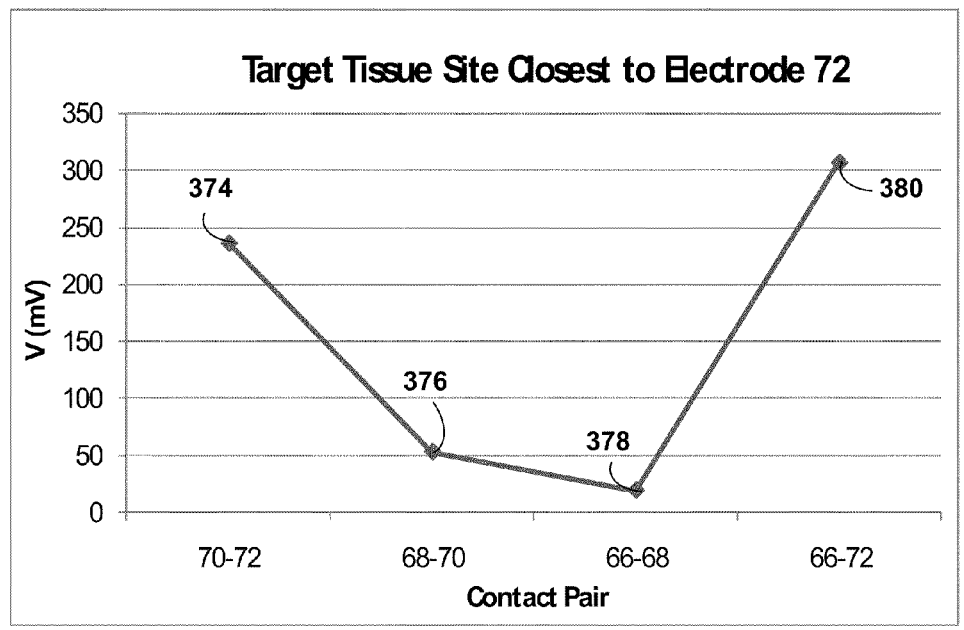

FIGS. 16A and 16B are graphs illustrating a scenario in which the target tissue site is closest to electrode 72. FIG. 16A illustrates relative values 366 for a first group of electrode combinations 70A-72, 70B-72, and 70C-72, relative values 368 for a second group of electrode combinations 68A-70A, 68B-70B, and 68C-70C, relative values 370 for a third group of electrode combinations 66-68A, 66-68B, and 66-68C, and relative value 372 for a fourth group comprising electrode combination 66-72. FIG. 16B illustrates the average relative values 374, 376, and 378 determined from relative values 366, 368, and 370. For example, average relative value 374 is determined by calculating the average value of relative values 366, i.e., the average of the relative values for each of electrode combinations 70A-72, 70B-72, and 70C-72 in the first group of electrode combinations. Relative value 380 is the same as relative value 372 because the electrode combination 66-72 comprises two ring electrodes and no groups of segmented electrodes. An algorithm such as algorithm 60 may then be used to determine the group of electrodes that is closest to the target tissue site based on the average relative values 366, 368, and 370 and the relative value 372. In this case, processor 40 determines that, based on algorithm 60 shown in FIG. 10, group of electrodes 72 is closest to the target tissue site.

Figure 17A:
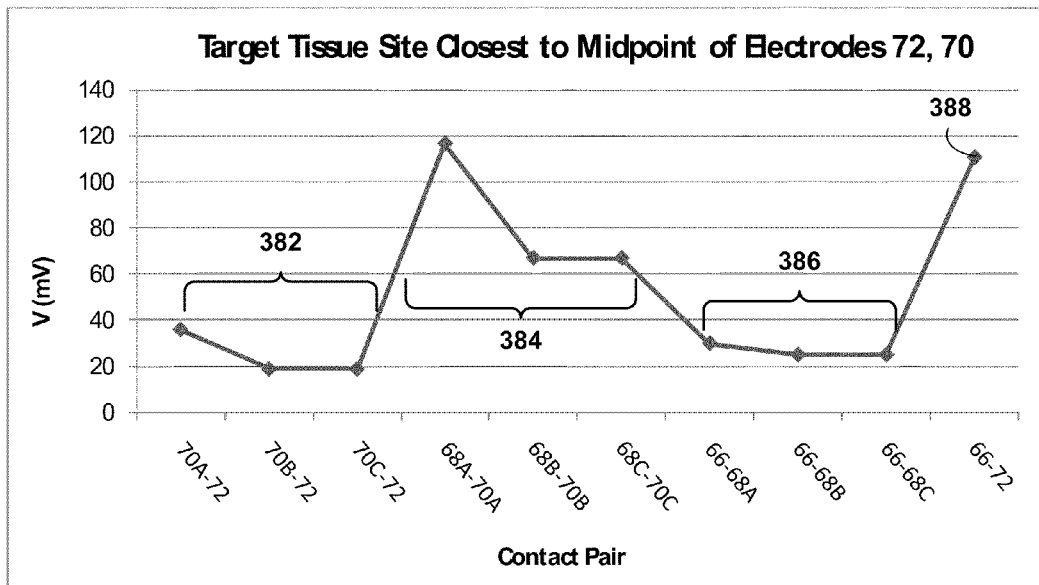
Figure 17B:
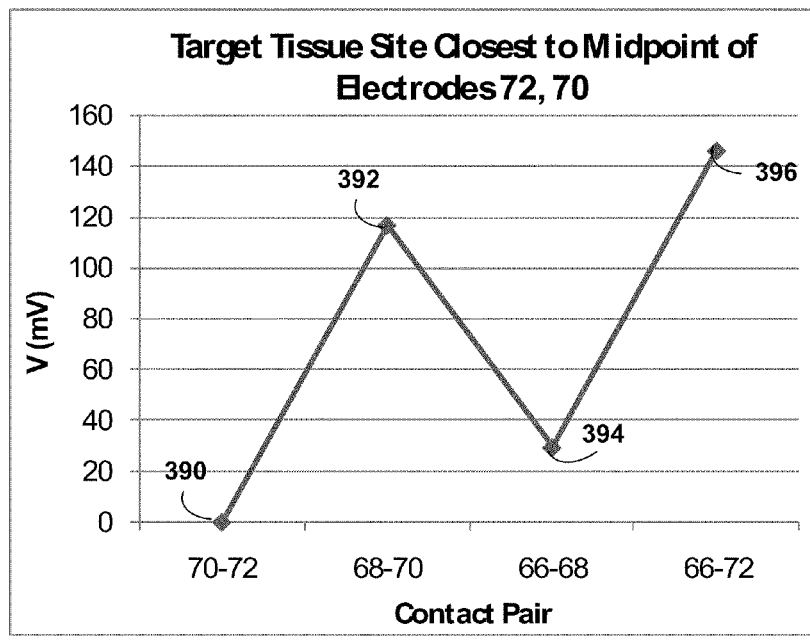

FIGS. 17A and 17B illustrate graphs for a scenario in which electrode 72 is determined to be closest to a target tissue site using the algorithm described with respect to FIG. 10. FIG. 17A illustrates relative values 382 for electrode combinations 70A-72, 70B-72, and 70C-72 in a first group of electrode combinations, relative values 384 for electrode combinations 68A-70A, 68B-70B, and 68C-70C in a second group of electrode combinations, relative values 386 for electrode combinations 66-68A, 66-68B, and 66-68C in a third group of electrode combinations, and relative value 388 for electrode combination 66-72 in a fourth group of electrode combinations. FIG. 17B illustrates the average relative values 390, 392, and 394 determined from relative values 382, 384, and 386. For example, average relative value 390 is determined by calculating the average value of each of the relative values in group 382, i.e., the average of the relative values for each of electrode combinations 70A-72, 70B-72, and 70C-72. Relative value 388 is the same as relative value 396 because the electrode combination 66-72 comprises two ring electrodes and no groups of segmented electrodes. Processor 40 can implement an algorithm, such as algorithm 60 described with respect to FIG. 10, to determine the group of electrodes that is closest to the target tissue site based on the average relative values 390, 392, and 394 and the relative value 396. In this case, executing the algorithm results in selecting groups of electrodes 72 and 70 as closest to the target tissue site. Specifically, the target tissue site is closest to the midpoint of groups of electrodes 72 and 70.

Figure 18A:
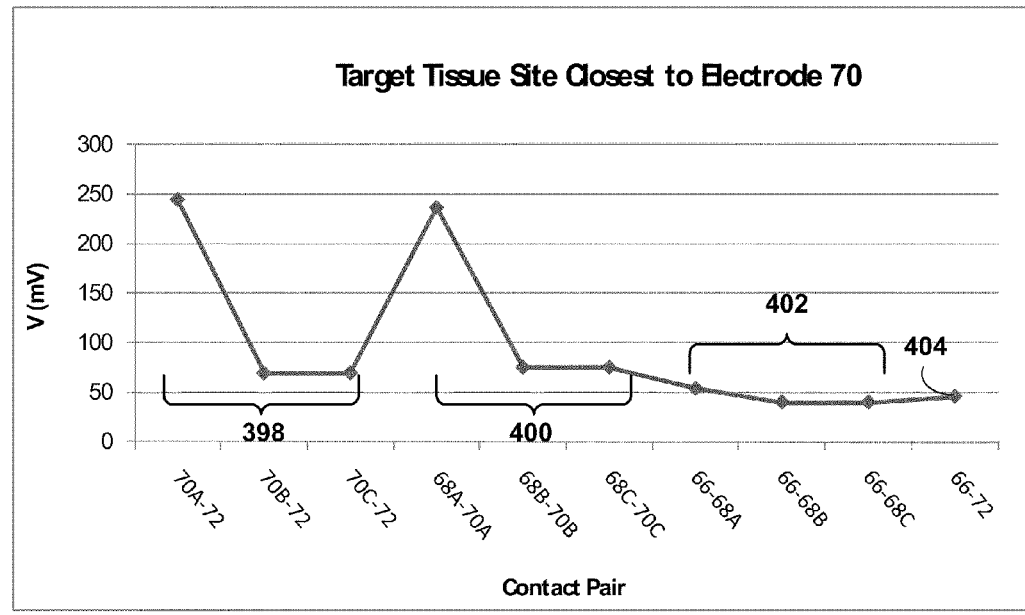
Figure 18B:
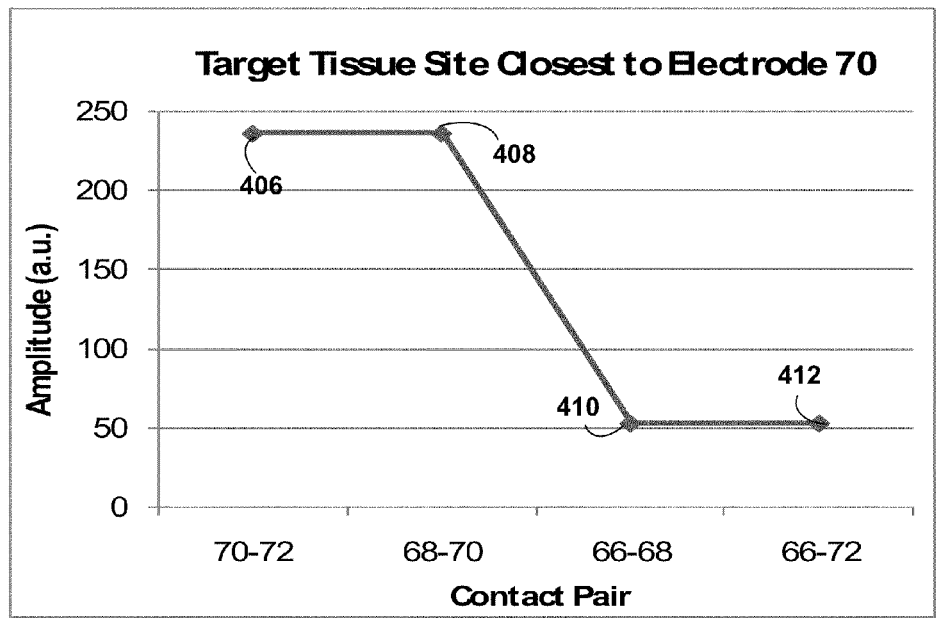

FIGS. 18A and 18B illustrate graphs for a scenario in which electrode 70 is determined to be closest to a target tissue site using the algorithm described with respect to FIG. 10. FIG. 18A illustrates relative values 398 for electrode combinations 70A-72, 70B-72, and 70C-72 in a first group of electrode combinations, relative values 400 for electrode combinations 68A-70A, 68B-70B, and 68C-70C in a second group of electrode combinations, relative values 402 for electrode combinations 66-68A, 66-68B, and 66-68C in a third group of electrode combinations, and relative value 404 for electrode combination 66-72 in a fourth group of electrode combinations. FIG. 18B illustrates the average relative values 406, 408, and 410 determined from each of the relative values in groups 398, 400, and 402. For example, average relative value 406 is determined by calculating the average value of relative values 398, i.e., the average of the relative values for each of electrode combinations 70A-72, 70B-72, and 70C-72. Relative value 404 is the same as relative value 412 because the electrode combination 66-72 comprises two ring electrodes and no groups of segmented electrodes. Processor 40 can implement an algorithm, such as algorithm 60 described with respect to FIG. 10, to determine the group of electrodes that is closest to the target tissue site based on the average relative values 406, 408, and 410 and the relative value 412. In this case, executing the algorithm results in selecting group of electrodes 70 as closest to the target tissue site.

Figure 19A:
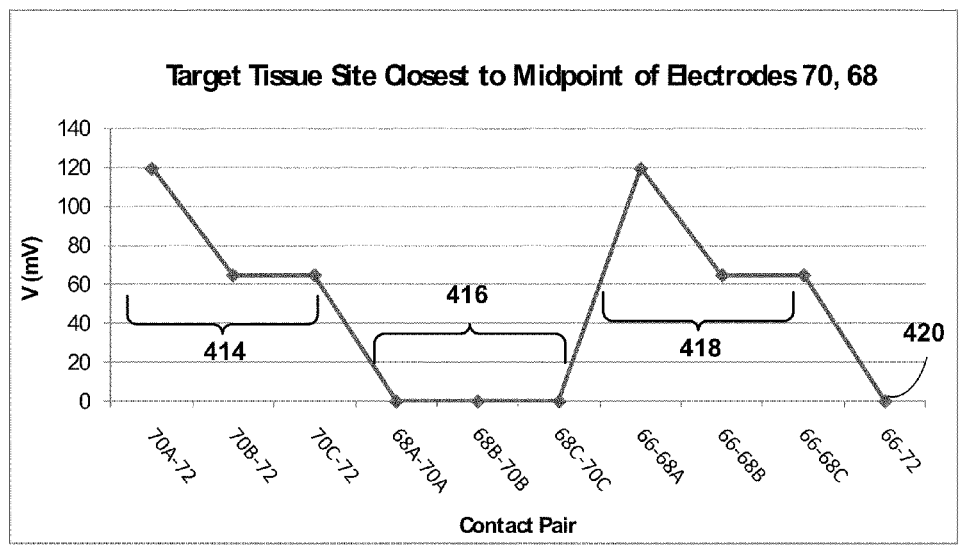
Figure 19B:
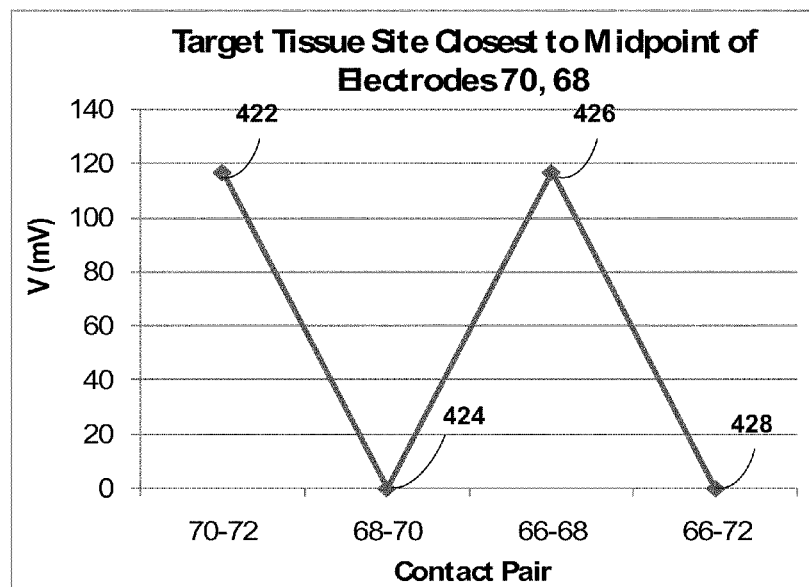

FIGS. 19A and 19B illustrate graphs for a scenario in which a target tissue site is determined to be near a midpoint of electrodes 70, 68 using the algorithm described with respect to FIG. 10. FIG. 19A illustrates relative values 414 for electrode combinations 70A-72, 70B-72, and 70C-72 in a first group of electrode combinations, relative values 416 for electrode combinations 68A-70A, 68B-70B, and 68C-70C in a second group of electrode combinations, relative values 418 for electrode combinations 66-68A, 66-68B, and 66-68C in a third group of electrode combinations, and relative value 420 for electrode combination 66-72 in a fourth group of electrode combinations. FIG. 19B illustrates the average relative values 422, 424, and 426 determined from each of the relative values in groups of relative values 414, 416, and 418. For example, average relative value 422 is determined by calculating the average value of relative values 414, i.e., the average of the relative values for each of electrode combinations 70A-72, 70B-72, and 70C-72. Relative value 428 is the same as relative value 420 because the electrode combination 66-72 comprises two ring electrodes and no groups of segmented electrodes. Processor 40 of IMD 16 can implement an algorithm, such as algorithm 60 described with respect to FIG. 10, to determine the group of electrodes that is closest to the target tissue site based on the average relative values 422, 422, and 424 and the relative value 428. In this case, executing the algorithm results in selecting groups of electrodes 70 and 68 as closest to the target tissue site. Specifically, the target tissue site is closest to the midpoint of groups of electrodes 70 and 68.

In accordance with the technique shown in FIG. 14, after determining which group of electrodes is closest to a target tissue site, and, therefore, determining the relative location of the target tissue site in a direction substantially parallel to a longitudinal axis of lead 62, processor 40 of IMD 16 (or a processor of another device, such as programmer 14) can determine which side of lead 62 (e.g., as indicated by a direction nonparallel to a longitudinal axis of lead 62, such as a direction substantially perpendicular to the longitudinal axis) is closest to the target tissue site. Identifying the location of the target tissue site in at least two directions (referred to herein as a three-dimensional algorithm) is useful for selecting stimulation electrodes from a plurality of electrodes including at least two segmented electrodes.

FIGS. 20A-20E illustrate graphs of relative values used to determine the side of the lead closest to the target tissue site, where different "sides" of lead 62 are indicated by a respective one of segmented (or partial ring) electrodes 70A, 70B, 70C. In the examples of FIGS. 20A-20E, group of electrodes 70 is used to determine whether the target tissue site is closest to the side of the lead containing electrode 70A, 70B, or 70C. In other examples, however, a different group of electrodes, e.g., group of electrodes 68, may be used to determine the side of the lead closest to the target tissue site.

Figure 20A:
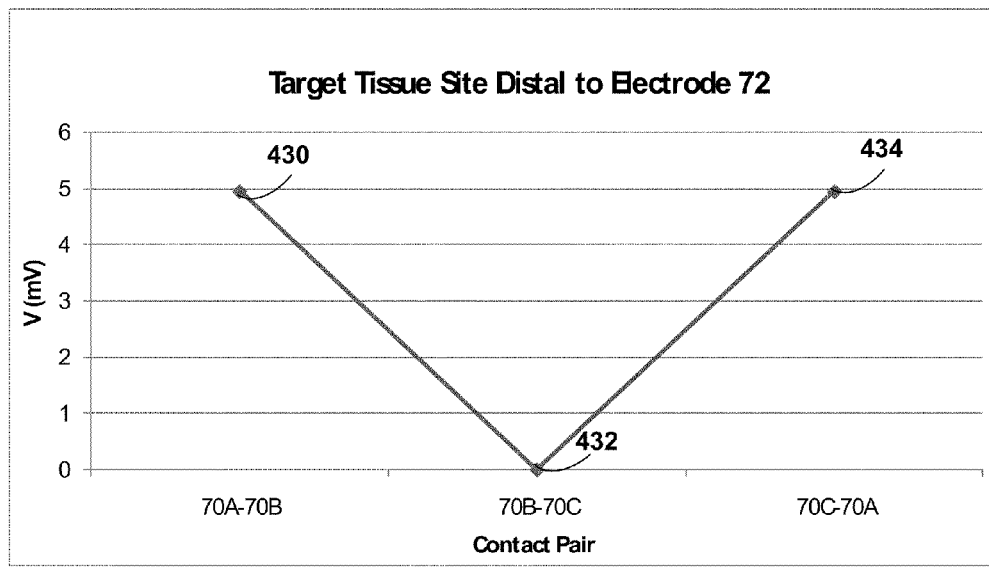

FIG. 20A illustrates a scenario in which the target tissue site has been determined to be located distal to the group of electrodes comprising electrode 72. Although the target tissue site is located relatively far from group of electrodes 70, group of electrodes 70 is used to determine the side of the lead 62 closest to the target tissue site because group of electrodes 70 comprises electrodes on three different sides of the lead 62, in contrast to group of electrode 72 which comprises only one ring electrode that extends around the entire perimeter of lead 62. Alternatively, group of electrodes 68, which also comprises three segmented electrodes, may be used. As shown in FIG. 20A, electrode combination 70A-70B has a relative value 430 of approximately 4.96 mV, electrode combination 70B-70C has a relative value 432 of approximately 0 mV, and electrode combination 70C-70A has a relative value 434 of approximately 4.96 mV. Because relative value 432 is substantially equal to zero and relative values 430 and 434 are substantially equal, i.e., the distribution of electrical potential between electrode combinations 70A-70B and 70C-70A are substantially symmetrical, processor 40 determines that, based on the algorithm described with respect to FIG. 14, the target tissue site is located closest to the side of lead 62 containing electrode 70A. In this case, the target tissue site is located closest to group of electrodes 72, and, thus, relatively far from group of electrodes 70. Consequently, relative values 430 and 434 have a relatively low amplitude value in comparison to scenarios in which the target tissue site is located closer to group of electrodes 70.

Figure 20B:
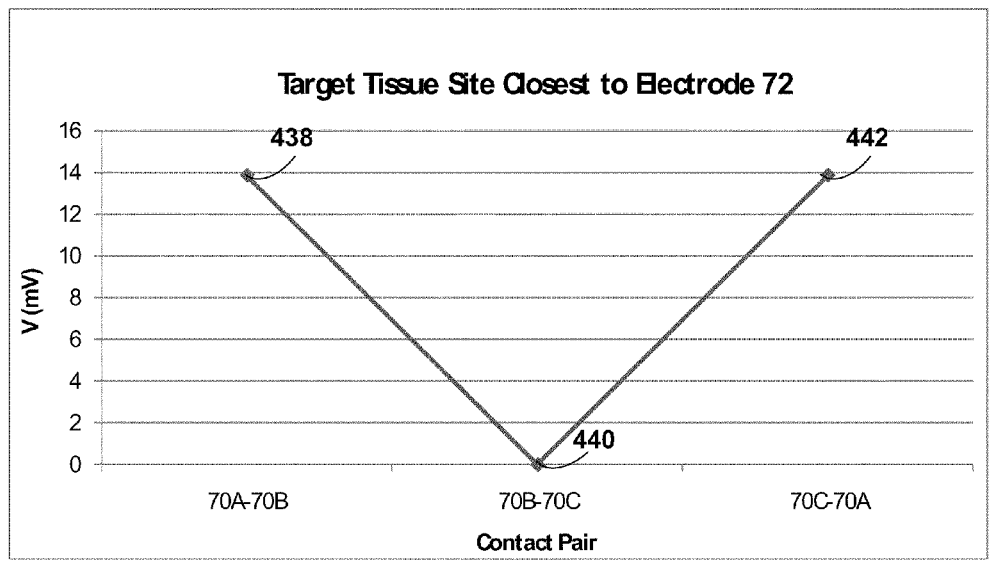

FIG. 20B illustrates a scenario in which the target tissue site has been determined to be located closest to group of electrodes 72. As with the scenario illustrated in FIG. 20A, although the target tissue site is located relatively far from group of electrodes 70, group of electrodes 70 is used to determine the side of the lead 62 closest to the target tissue site because group of electrodes 70 comprises electrodes on three different sides of the lead 62, in contrast to group of electrode 72 which comprises only one ring electrode around the entire perimeter of lead 62. Alternatively, group of electrodes 68, which also comprises three electrodes, may be used. As shown in FIG. 20B, electrode combination 70A-70B has a relative value 438 of approximately 13.87 mV, electrode combination 70B-70C has a relative value 440 of approximately 0 mV, and electrode combination 70C-70A has a relative value 442 of approximately 13.87 mV. Because relative value 440 is substantially zero and relative values 438 and 442 are substantially equal, i.e., the distribution of electrical potential between electrode combinations 70A-70B and 70C-70A are symmetrical, processor 40 determines that, based on the algorithm described with respect to FIG. 14, the target tissue site is located closest to the side of lead 62 containing electrode 70A. In this case, the target tissue site is located closest to group of electrodes 72, and, thus, relatively far from group of electrodes 70. Consequently, relative values 438 and 442 have a relatively low amplitude value in comparison to scenarios in which the target tissue site is located closer to group of electrodes 70. However, in comparison to the scenario illustrated in FIG. 20A, the target tissue site is located closer to group of electrodes 70 and, thus, the amplitude of relative values 438 and 442 is higher than in the scenario illustrated in FIG. 20A.

Figure 20C:
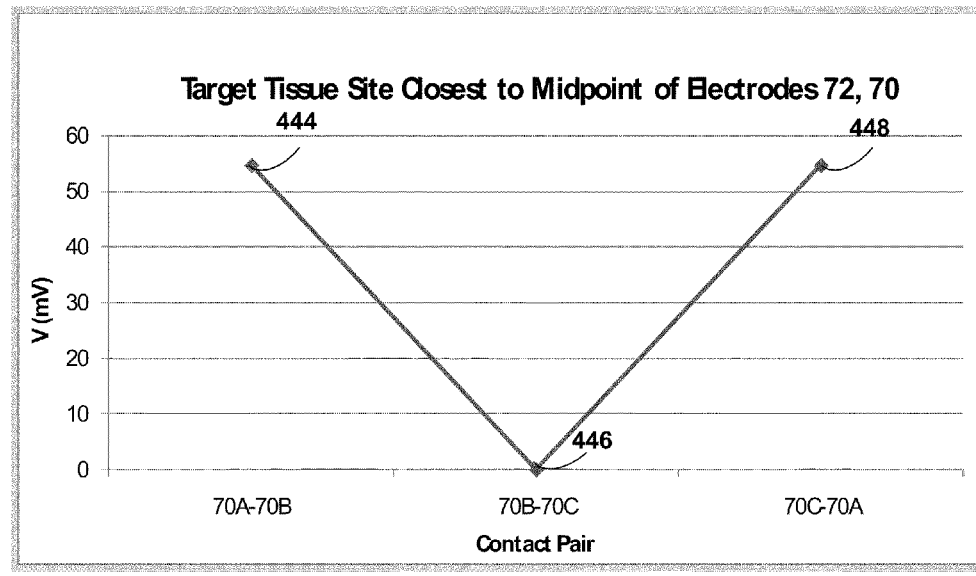

FIG. 20C illustrates a scenario in which the target tissue site has been determined to be located closest the midpoint of groups of electrodes 72 and 70, e.g., based on the algorithm described with respect to FIG. 10. As shown in FIG. 20C, electrode combination 70A-70B has a relative value 444 of approximately 50.78 mV, electrode combination 70B-70C has a relative value 446 of approximately 0 mV, and electrode combination 70C-70A has a relative value 448 of approximately 50.78 mV. Because relative value 446 is substantially equal to zero and relative values 444 and 448 are substantially equal, i.e., the distribution of electrical potential between electrode combinations 70A-70B and 70C-70A are substantially symmetrical, processor 40 determines that the target tissue site is located closest to the side of lead 62 containing electrode 70A. In this case, the target tissue site is located closest to the midpoint of groups of electrodes 72 and 70, and, thus, closer to group of electrodes 70 than in either of the scenarios illustrated in FIGS. 20A and 20B. Consequently, the amplitudes values of relative values 444 and 448 are higher than the corresponding amplitude values in the scenarios illustrated in FIGS. 20A and 20B.

Figure 20D:
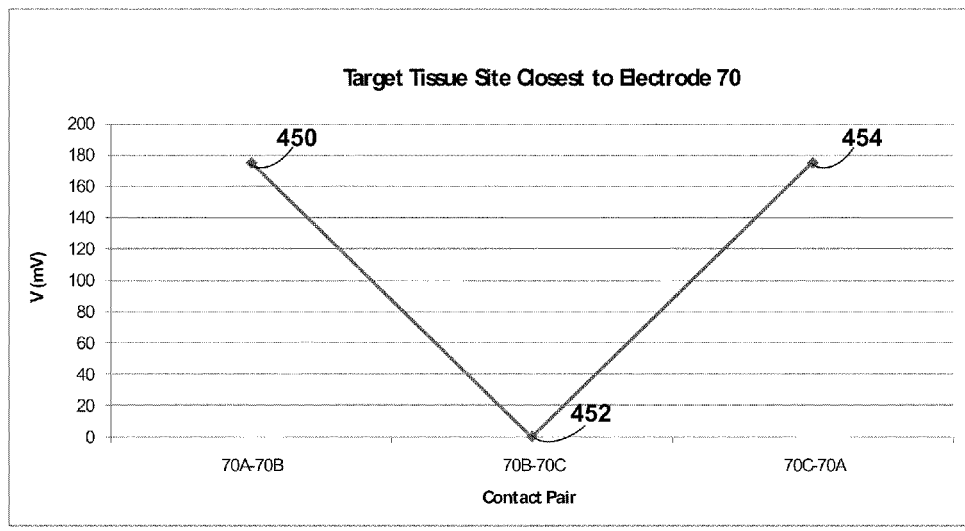

FIG. 20D illustrates a scenario in which the target tissue site has been determined to be located closest to group of electrodes 70. As shown in FIG. 20D, electrode combination 70A-70B has a relative value 450 of approximately 175.42 mV, electrode combination 70B-70C has a relative value 452 of approximately 0 mV, and electrode combination 70C-70A has a relative value 454 of approximately 175.42 mV. Because relative value 452 is substantially equal to zero and relative values 450 and 454 are substantially equal, i.e., the distribution of electrical potential between electrode combinations 70A-70B and 70C-70A are substantially symmetrical, processor 40 determines that the target tissue site is located closest to the side of lead 62 containing electrode 70A. In this case, the target tissue site is located closest to group of electrodes 70. Consequently, the amplitudes values of relative values 450 and 454 are higher than the corresponding amplitude values in the scenarios illustrated in FIGS. 20A, 20B, and 20C.

Figure 20E:
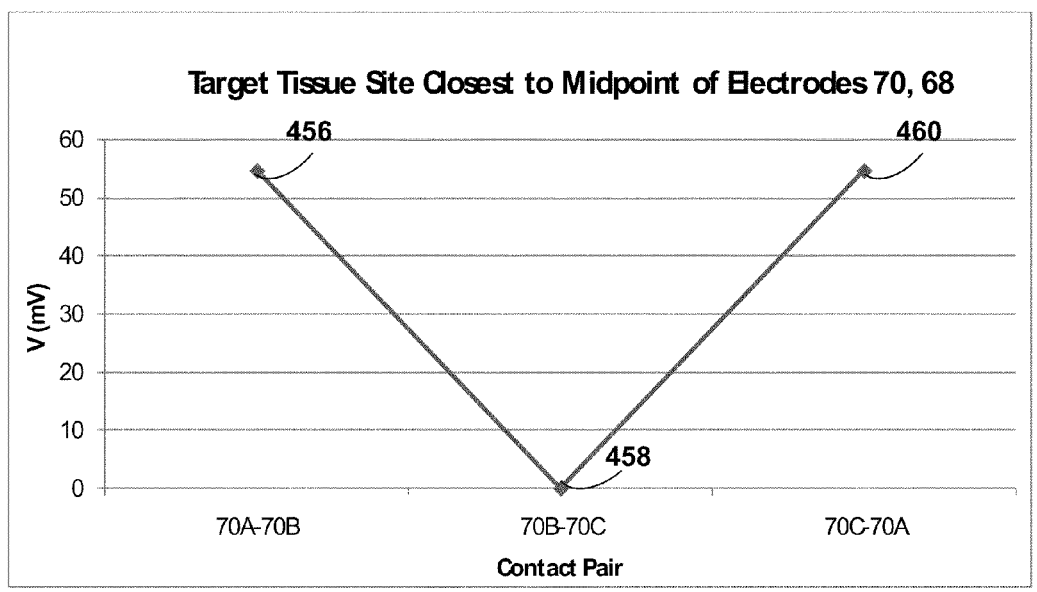

FIG. 20E illustrates a scenario in which the target tissue site has been determined to be located closest to the midpoint of groups of electrodes 70 and 68, e.g., based on the algorithm described with respect to FIG. 10. As shown in FIG. 20E, electrode combination 70A-70B has a relative value 456 of approximately 54.78 mV, electrode combination 70B-70C has a relative value 458 of approximately 0 mV, and electrode combination 70C-70A has a relative value 460 of approximately 54.78 mV. Because relative value 458 is substantially equal to zero, i.e., relative value 458 has the lowest relative value, and relative values 456 and 460 are substantially equal, i.e., the distribution of electrical potential between electrode combinations 70A-70B and 70C-70A are substantially symmetrical, it can be determined that the target tissue site is located closest to the side of lead 62 containing electrode 70A. In this case, the target tissue site is located closest to the midpoint of groups of electrodes 70 and 68, and, thus, farther from group of electrodes 70 than in the scenario illustrated in FIG. 20D. Consequently, the amplitudes values of relative values 456 and 460 are lower than the corresponding amplitude values in the scenario illustrated in FIG. 20D, where the target tissue site is located closest to group of electrodes 70.

In some examples, the target tissue site may be located between two of electrodes 70A, 70B, and 70C. For example, the target tissue site may be located between electrodes 70A and 70B, and closer to electrode 70A than electrode 70B. In this case, the difference in tissue electrical potential sensed by electrodes 70A and 70B is smaller than the difference in electrical potential sensed by electrodes 70C and 70A because electrode 70C is located much farther away from the target tissue site than electrode 70B. In this case, the relative value for the electrode combination 70C-70A is slightly greater than the relative value for the electrode combination 70B-70C. However, the relative value for the electrode combination 70B-70C is the lowest relative value. Thus, in this case, it can be determined that the target tissue site is once again located closest to electrode 70A. Similar analyses between bipolar electrical potential recordings may be performed if more electrode segments or multiple electrode arrays are used in order to localize the electrode closest to the source of activity.

In each of the examples described herein, processor 40 of IMD 16 or a processor of another device can automatically determine which electrode is closest to the target tissue site using the techniques described herein.

Figure 21:
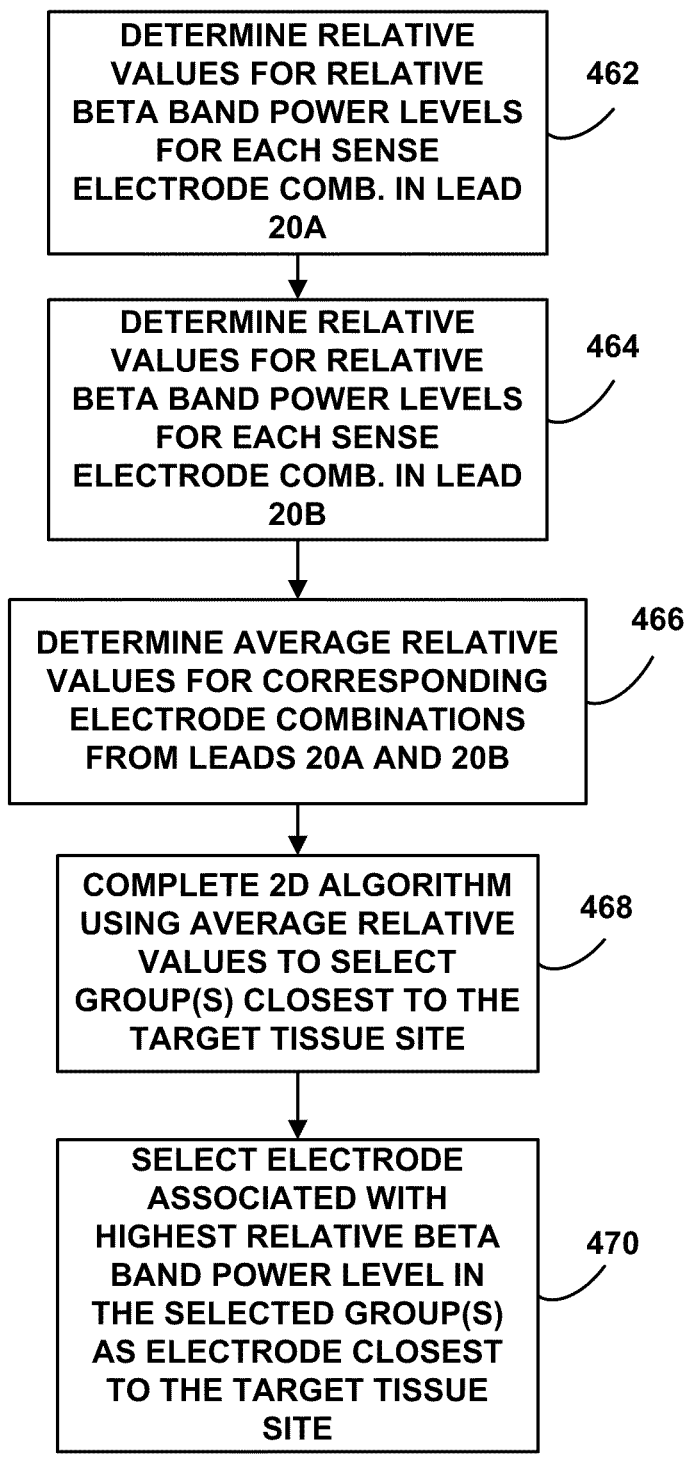
FIG. 21 is a flow diagram illustrating an example technique for determining the electrode or electrodes closest to a target tissue site for an IMD comprising multiple leads each comprising groups of electrodes.

FIG. 21 is a flow diagram illustrating an example technique for determining the electrode or electrodes closest to the target tissue site for an IMD comprising multiple leads each comprising groups of electrodes, such as leads 20A and 20B comprising electrodes 24 and 26, respectively (FIG. 3). In this example, the technique is described with respect to leads 20A and 20B. In other examples, however, the technique may be applicable to an IMD with any combination and configuration of leads and electrodes. As with FIG. 14, memory 42 of IMD 16 can store algorithm 60 that stores instructions that, when executed by processor 40, causes processor 40 (alone or in combination with another processor) to carry out each of the steps of the technique illustrated in FIG. 21. However, in other examples, the technique may be carried out by a different processor, such as processor 74. With respect to FIG. 21, electrodes at the same position along the longitudinal axis of leads 20A and 20B will be referred to as a group of electrodes. For example, a group D of electrodes may comprise electrodes 24D and 26D, which are at the same position along the longitudinal axis of the respective leads.

In accordance with the technique shown in FIG. 21, processor 40 determines the relative values of the relative beta band power level for each electrode combination that includes electrodes 24 of lead 20A, i.e., electrode combinations 24A-24B, 24B-24C, 24C-24D, and 24A-24D (462). Next, processor 40 determines the relative values for each electrode combination of lead 20B, i.e., electrode combinations 26A-26B, 26B-26C, 26C-26D, and 26A-26D (464). After processor 40 has determined the relative values for each electrode combination, processor 40 determines an average value for the relative values for corresponding electrode combinations from leads 20A and 20B (466). For example, with respect to leads 20A, 20B, processor 40 determines an average A-B relative value for electrode combinations 24A-24B and 26A-26B, an average B-C relative value for electrode combinations 24B-24C and 26C-26D, an average C-D relative value for electrode combinations 24C-24D and 26C-26D, and an average A-D relative value for electrode combinations 24A-24D and 26A-26D.

Processor 40 then applies algorithm 60 using the average A-B, B-C, C-D, and A-D relative values to determine the group or groups of electrodes, i.e., A, B, C, or D, closest to the target tissue site (468). The determination of the group of electrodes closest to the target tissue site indicates the relative location of the target tissue site in a first direction that is substantially parallel to a longitudinal axis of at least one of leads 20A, 20B (or both of leads 20A, 20B if the longitudinal axes of leads 20A, 20B are positioned parallel to each other). After processor 40 selects the group or groups of electrodes closest to the target tissue site, processor 40 determines which of the electrodes 24 or 26 was used to sense the bioelectrical brain signal within the selected group has the highest relative beta band power level, and processor 40 selects the electrode associated with the highest relative beta band power level as closest to the target tissue site (470).

For each of the techniques illustrated in FIGS. 7A, 7B, 9A, 9B, 9C, 10, 14, and 21, processor 40 (or a processor of another device, such as programmer 14) may, in some examples, automatically rank each electrode based on its location relative to the target tissue site. The rank can indicate, for example, which electrode may deliver the most efficacious stimulation therapy delivery to patient 12, or may simply indicate which electrode is closest to the target tissue site.

For example, with respect to the technique illustrated in FIG. 10, processor 40 may determine that the target tissue site is located closest to electrode 24C, as with the scenario illustrated in FIG. 12A. After determining that the target tissue site is closest to electrode 24C, processor 40 may generate a suggestion that at least a substantial portion of the electrical stimulation therapy (e.g., approximately 100%), as indicated by various factors including current or voltage amplitude, should be delivered via electrode 24C. Processor 40 may also rank electrode 24C as the highest or most effective electrode, e.g., number one. Alternatively or additionally, processor 40 may automatically adjust electrical stimulation parameters based on determining that the majority of electrical stimulation therapy should be delivered via electrode 24C.

In another example, processor 40 may determine that the target tissue site is located between electrodes 24B and 24C and closest to electrode 24C, e.g., between the midpoint of electrodes 24B and 24C and electrode 24C, as with the scenario illustrated in FIG. 12B. After determining that the target tissue site is between electrodes 24B and 24C and closest to electrode 24C, processor 40 may generate a corresponding suggestion for the distribution of electrical stimulation therapy delivery. For example, processor 40 may determine that the largest percentage of electrical stimulation therapy, e.g., approximately 75%, should be delivered via electrode 24C and that a relatively smaller percentage of electrical stimulation therapy, e.g., approximately 25%, should be delivered via electrode 24B because the target tissue site is located close to both electrode 24B and 24C, but closest to electrode 24C.

Processor 40 may also rank electrode 24C as the highest (e.g., stimulation electrode closest to the target tissue site), and may rank electrode 24B as the next highest stimulation electrode. Processor 40 may rank electrodes 24A and 24D as the lowest or least effective stimulation electrodes, e.g., number three or numbers three and four. Alternatively The order of electrodes may or may not indicate which electrode may provide the most efficacious stimulation therapy. For example, although electrode 24C is closest to a target tissue site, it may later be determined that stimulation therapy delivered via electrode 24C results in side effects not present when stimulation therapy is delivered via electrode 24B. In such a case, the clinician or processor 40, based on user input indicating the side effects, may select the next-highest electrode or a different electrode to deliver stimulation.

In some examples, processor 40 automatically adjusts electrical stimulation parameters based on determining that the majority of electrical stimulation therapy should be delivered via electrode 24C and a relatively smaller percentage of electrical stimulation therapy should be delivered via electrode 24B. For example, processor 40 may select the stimulation parameters to distribute the distribution of current or voltage between electrodes, e.g., as described in further detail below with respect to Table 3. A clinician or other user may use the table to adjust electrical stimulation parameters and/or to make other observations that may be useful in providing the patient with effective electrical stimulation therapy.

In some examples, the relative distribution of current or voltage between the electrodes selected to be closest to a target tissue site may be predetermined and processor 40 may select the relative distribution of current or voltage between the electrodes based on where the target tissue site is located relative to the selected electrodes. For example, memory 42 (FIG. 3) of IMD 16 or a memory of another device can associate different power distributions between electrodes with different locations of the target tissue site. As an example, if the target tissue site is determined to be between first and second electrode, but closest to the first electrode, the predetermined distribution of stimulation signal power delivered by the first and second electrodes may be about 75% and about 25%, respectively, or about 80% and 20% respectively. Other percentages are contemplated. Processor 40 can also determine the relative power distribution between more than two electrodes.

In another example, processor 40 (or a processor of another device, such as programmer 14) may determine that the target tissue site is located between electrodes 24B and 24C, e.g., at the midpoint of electrodes 24B and 24C, as with the scenario illustrated in FIG. 12C. Processor 40 may generate a corresponding suggestion for distribution of electrical stimulation therapy. For example, processor 40 may determine that approximately equal percentages of electrical stimulation therapy, e.g., approximately 50%, should be delivered via both of electrodes 24B and 24C because the target tissue site is located approximately halfway between electrodes 24B and 24C. Processor 40 may also rank electrodes 24B and 24C as the highest or most effective stimulation electrodes, e.g., number one or numbers one and two. Processor 40 may rank electrodes 24A and 24D as the lowest or least effective stimulation electrodes. Alternatively or additionally, processor 40 may automatically adjust electrical stimulation parameters based on determining that approximately equal percentages of electrical stimulation should be delivered via electrodes 24B and 24C.

TABLE 3

| | Electrode rank | |
|---|---|---|
| Rank | Electrode | Suggested Distribution (%) |
| 1 | 24C | 75 |
| 2 | 24B | 25 |
| 3 | 24A | 0 |
| 3 | 24D | 0 |

In examples in which sensing module 46 senses bioelectrical brain signals in a unipolar sensing configuration, processor 40 (or a processor of another device, such as programmer 14) may determine a rank of electrodes based on comparisons between the relative beta band power levels of the bioelectrical brain signals sensed by each unipolar electrode combination. For example, processor 40 may analyze a spectrogram, e.g., the spectrogram shown in FIG. 2, to determine the relative beta band power level of a bioelectrical brain signal sensed by a respective one of the electrodes 24A, 24B, 24C, and 24D in a unipolar configuration. Processor 40 may then compare the relative beta band power levels sensed by each of the electrodes to one another and determine the rank of each electrode based on the relative beta band power levels. For example, processor 40 may rank the electrode that sensed the bioelectrical brain signal with the highest beta band power level as the highest stimulation electrode (e.g., closest to the target tissue site) and the electrode that sensed the bioelectrical brain signal with the lowest beta band power level as the lowest stimulation electrode. Processor 40 (or a processor of another device, such as programmer 14) may generate a suggestion for the distribution of electrical stimulation therapy between electrodes 24A-24D based on comparing the beta band power levels.

For example, processor 40 can determine that if electrode 24C sensed a bioelectrical brain signal having a beta band (or other selected frequency band) power level that is three times greater than the beta band power level of a bioelectrical brain signal sensed by electrode 24B, processor 40 can suggest that 75% of the power of the electrical stimulation signal be delivered via electrode 24C and 25% of the power of the electrical stimulation signal be delivered via electrode 24B. Other distributions are also contemplated and need not necessarily be proportional to the ratio of power levels in a selected frequency band. The power of a stimulation signal can be a function of, for example, the voltage or current amplitude. Therefore, the relative voltage or current amplitude of stimulation signals delivered via a plurality of electrodes can be selected based on the ratio of power levels within a selected frequency band of bioelectrical brain signals sensed by the electrodes in a unipolar configuration.

In some examples, providing a rank of each stimulation electrode may facilitate patient-specific electrical stimulation therapy delivery. For example, in some examples, delivery of electrical stimulation via the highest-ranked electrode combination may cause undesirable side effects. A clinician or user may access the rank of electrodes in order to choose a different electrode combination that may cause fewer side effects but may still be located relatively close to the target tissue site. In other examples, processor 40 may access the rank of electrodes in order to automatically modify the stimulation electrode combination based on feedback from the patient regarding effects of a particular stimulation electrode combination.

The techniques illustrated herein, such as the techniques illustrated in FIGS. 7B, 9A, 9B, 9C, 10, 14, and 21, have been described with respect to sensing bioelectrical signals with electrode combinations in a unipolar configuration and then converting the unipolar bioelectrical signal data into bipolar bioelectrical signal data via the relative values. For example, with respect to the technique shown in FIG. 7B, processor 40 controls sensing module 46 to sense a first bioelectrical signal with electrode 24A (FIG. 3) and a reference (e.g., a housing electrode), a second bioelectrical signal with electrode 24B and a reference, a third bioelectrical signal with electrode 24C and a reference, and a fourth bioelectrical signal with electrode 24D and a reference. Then, processor 40 determines relative values indicating the difference in relative beta band power levels for bioelectrical signals sensed by each electrode combination, i.e., electrode combinations 24A-24B, 24B-24C, 24C-24D, and 24A-24D.

Figure 22:
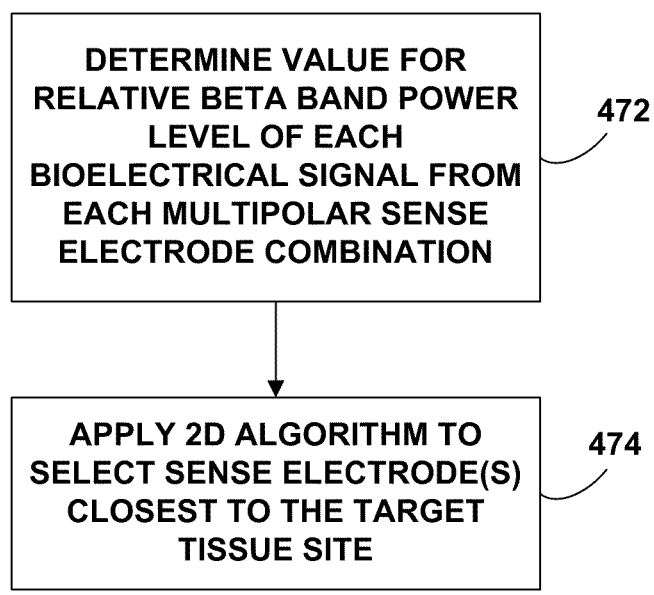
FIG. 22 is a flow diagram illustrating an example technique for selecting sense electrode combinations that are closest to a target tissue site based on bioelectrical brain signals sensed via multipolar sense electrode combinations.

As shown in FIG. 22, in other examples, rather than determining the relative value of the relative beta band power level for each combination of the first, second, third, and fourth bioelectrical signals, processor 40 senses bioelectrical brain signals in a bipolar configuration (e.g., with combinations of electrodes 24) and determines the value of the relative beta band power level of the bioelectrical brain signal sensed via each bipolar electrode configuration (472). The relative beta band power level of the bioelectrical brain signal sensed via the bipolar electrode configuration is substantially equal to the relative value of the relative beta band power level of a bioelectrical brain signal sensed via the two electrodes of the bipolar configuration in a unipolar configuration. Processor 40 can then execute algorithm 60 to select the one or more sense electrodes closest to the target tissue site based on the value of the relative beta band power levels of the bioelectrical brain signals sensed via respective bipolar electrode configurations (474).

Figure 23:
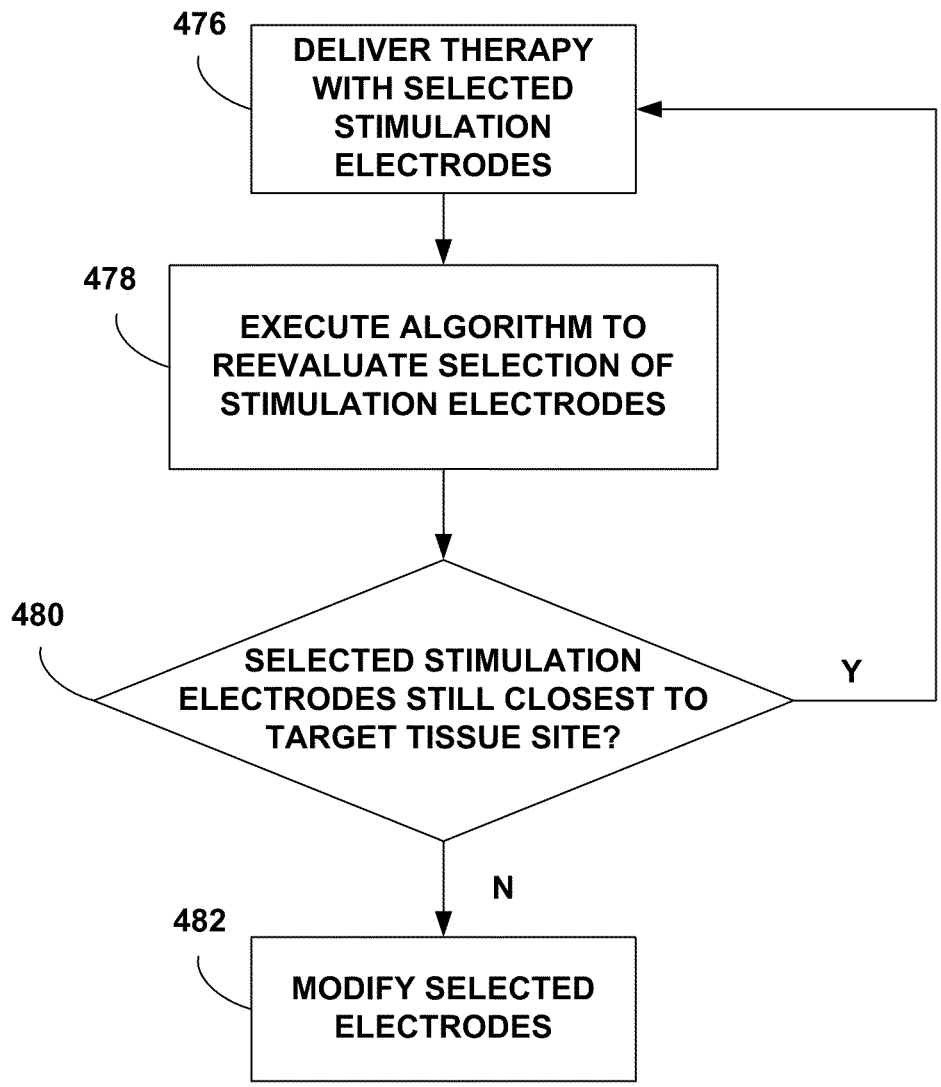
FIG. 23 is a flow diagram illustrating an example technique for evaluating selected stimulation electrodes.

FIG. 23 is a flow diagram illustrating an example technique for modifying stimulation electrode selection when electrical stimulation therapy is being delivered. Processor 40 may instruct stimulation generator 44 to deliver electrical stimulation therapy based on determining that one or more selected stimulation electrodes are closest to the target tissue site (476). During therapy delivery (e.g., chronic therapy delivery), processor 40 can periodically asses the positions of the one or more selected one or more stimulation electrodes in order to ensure that electrical stimulation therapy is delivered to the appropriate location within brain 28 of patient 12. For example, processor 40 may execute algorithm 60 after a particular amount of time (e.g., a predetermined and stored amount of time, or a random time) has passed or after a particular amount of electrical stimulation has been delivered to determine the electrodes located closest to the target tissue site (478).

Processor 40 may determine whether the electrodes located closest to the target tissue site are the same as the selected stimulation electrodes (480). If the electrodes located closest to the target tissue site are the same as the selected stimulation electrodes, processor 40 may continue to deliver electrical stimulation therapy with the selected electrodes (476). If, on the other hand, processor 40 determines that the electrodes located closest to the target tissue site are no longer the selected stimulation electrodes, processor 40 may modify the selected stimulation electrodes in order to provide the most efficacious therapy to patient 12 (482).

The techniques described in this disclosure, including those attributed to programmer 14, IMD 16, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. While the techniques described herein are primarily described as being performed by processor 40 of IMD 16 and/or processor 70 of programmer 14, any one or more parts of the techniques described herein may be implemented by a processor of one of IMD 16, programmer 14, or another computing device, alone or in combination with each other.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various embodiments of have been described. These and other embodiments are within the scope of the following claims.

The invention claimed is:

1. A system comprising:
   a plurality of electrodes;
   a sensing module that senses a plurality of bioelectrical brain signals, each of the plurality of bioelectrical brain signals being sensed via at least one respective electrode of the plurality of electrodes; and
   a processor that determines a frequency domain characteristic for each of the plurality of bioelectrical signals; determines a plurality of relative values of the frequency domain characteristic, wherein each of the plurality of relative values is based on at least two of the frequency domain characteristics; determines whether a first relative value of the plurality of relative values is greater than or less than at least one other relative value of the plurality of relative values; in response to determining that the first relative value is greater than or less than the at least one other relative value, determines whether a second relative value of the plurality of relative values is greater than or less than another relative value of the plurality of relative values; determines whether a target tissue site is positioned between two electrodes of the plurality of electrodes based on determining whether the first relative value is greater than or less than at least one other relative value and based on determining whether the second relative value is greater than or less than another relative value; and selects at least one electrode of the plurality of electrodes for delivering stimulation to the patient based on determining whether the target tissue site is positioned between the two electrodes.

2. The system of claim 1, wherein the frequency domain characteristic comprises a power level of the respective bioelectrical signal in a selected frequency band.

3. The system of claim 2, wherein the selected frequency band comprises at least one of a beta band or a gamma band.

4. The system of claim 1, wherein the processor determines a greatest relative value of the frequency domain characteristic and selects the at least one electrode of the plurality of electrodes for delivering stimulation to the patient based on determining the greatest relative value of the frequency domain characteristic.

5. The system of claim 1, wherein the sensing module senses the plurality of bioelectrical signals with a plurality of unipolar electrode combinations.

6. The system of claim 5, wherein the processor determines a magnitude of a difference in the frequency domain characteristics of at least two bioelectrical signals in order to determine the plurality of relative values of the frequency domain characteristic.

7. The system of claim 1, wherein the sensing module senses the plurality of bioelectrical signals with a plurality of bipolar electrode combinations.

8. The system of claim 7, wherein the frequency domain characteristic of each bioelectrical signal indicates the relative values.

9. The system of claim 1, wherein the bioelectrical signals comprise a first set of bioelectrical signals, wherein at least three electrodes of the plurality of electrodes comprise a common position along a longitudinal axis of a lead,
wherein the sensing module senses a second set of bioelectrical signals within the brain of the patient with at least one electrode of the at least three electrodes, and
wherein the processor determines a frequency domain characteristic for each of the bioelectrical signals of the second set of bioelectrical signals and selects one of the electrodes of the at least three electrodes for delivering stimulation to the patient based on the frequency domain characteristics of the bioelectrical signals of the second set of bioelectrical signals.

10. The system of claim 1, wherein the two electrodes of the plurality of electrodes comprise electrodes with which bioelectrical brain signals used to determine the second relative value were sensed, wherein the processor determines whether the target tissue site is positioned between the two electrodes by at least determining that the second relative value is the lowest relative value of the plurality of relative values.

11. The system of claim 1, wherein the two electrodes of the plurality of electrodes comprises a first electrode and a second electrode, wherein the processor determines that the target tissue site is located closer to the first electrode than the second electrode and selects electrical stimulation parameter values based on determining that the target tissue site is located closer to the first electrode than the second electrode.

12. The system of claim 11, wherein the processor selects electrical stimulation parameter values based on determining that the target tissue site is located closer to the first electrode than the second electrode by at least selecting electrical stimulation parameter values to unevenly distribute delivery of electrical stimulation therapy between the first and second electrodes.

13. The system of claim 12, wherein the processor selects electrical stimulation parameter values to unevenly distribute delivery of electrical stimulation therapy between the first and second electrodes by at least selecting electrical stimulation parameter values to distribute a stimulation signal power between the first and second electrodes.

14. The system of claim 13, wherein the processor selects electrical stimulation parameter values to distribute a stimulation signal power between the first and second electrodes by at least selecting electrical stimulation parameter values to deliver a first percentage of the stimulation signal power via the first electrode and a second percentage of the stimulation signal power via the second electrode, wherein the first percentage and the second percentage total one hundred percent of the stimulation signal power, and wherein the first percentage and the second percentage are unequal.

15. The system of claim 1, wherein the two electrodes of the plurality of electrodes comprises a first electrode and a second electrode, the plurality of bioelectrical brain signals comprises a first bioelectrical brain signal sensed via the first electrode and a second bioelectrical brain signal sensed via the second electrode, wherein the processor determines the frequency domain characteristic for each bioelectrical brain signal by at least determining a first frequency domain characteristic of the first bioelectrical brain signal and a second frequency domain characteristic of the second bioelectrical brain signal, wherein the processor selects electrical stimulation parameter values to distribute delivery of electrical stimulation therapy between the first and second electrodes based on a ratio of the first and second frequency domain characteristics.

16. A system comprising:
a plurality of electrodes;
a sensing module that senses a first group of bioelectrical signals in a brain of a patient via a first group of electrodes comprising at least one electrode from the plurality of electrodes; a second group of bioelectrical signals in the brain of the patient via a second group of electrodes comprising at least one electrode from the plurality of electrodes; a third group of bioelectrical signals in the brain of the patient via a third group of electrodes comprising at least one electrode from the plurality of electrodes; and a fourth group of bioelectrical signals in the brain of the patient via a fourth group of electrodes comprising at least one electrode from the plurality of electrodes; and
a processor that determines a frequency domain characteristic for each of the bioelectrical signals within each of the first, second, third, and fourth groups of bioelectrical signals; determines a first relative value of the frequency domain characteristic based on the frequency domain characteristics for the first and second groups of bioelectrical signals; determines a second relative value of the frequency domain characteristic based on the frequency domain characteristics for the second and third groups of bioelectrical signals; determines a third relative value of the frequency domain characteristic based on the frequency domain characteristics for the third and fourth groups of bioelectrical signals; determines a fourth relative value of the frequency domain characteristic based on the frequency domain characteristics for the first and fourth groups of bioelectrical signals; if the fourth relative value is greater than the first, second, and third relative values, and if at least one of the first relative value is not greater than the second relative value or the second relative value is not greater than the third relative value, and if at least one of the first relative value is not less than the second relative value or the second relative value is not less than the third relative value, then the processor determines whether the first relative value is less than the third relative value; and selects at least one electrode from at least one of the first, second, third, or fourth groups of electrodes for delivering stimulation to a target tissue site of the patient based on the first, second, third, and fourth relative values, wherein the processor selects the at least one electrode by selecting at least one electrode from at least one of the first or second groups of electrodes if the first relative value is less than the third relative value.

17. The system of claim 16, wherein the first group of electrodes is located at a first position along a longitudinal axis of a lead, the second group of electrodes is located at a second position proximal to the first position along the longitudinal axis of the lead, the third group of electrodes is located at a third position proximal to the second position along the longitudinal axis of the lead, and the fourth group of electrodes is located at a fourth position proximal to the third position along the longitudinal axis of the lead.

18. The system of claim 16, wherein the processor selects at least one electrode from at least one of the first, second, third, or fourth groups of electrodes for delivering stimulation to a target stimulation site of the patient based on the first, second, third, and fourth relative values based on determining whether at least one of the first, second, third, or fourth groups of electrodes is closest to the target tissue site based on the first, second, third, and fourth relative values.

19. The system of claim 16, wherein, if the processor determines that the fourth relative value is greater than the first, second, and third relative values, then the processor determines whether the first relative value is greater than the second relative value and whether the second relative value is greater than the third relative value and selects at least one electrode from the first group of electrodes if the first relative value is greater than the second relative value and the second relative value is greater than the third relative value.

20. The system of claim 16, wherein, if the processor determines that the fourth relative value is greater than the first, second, and third relative values, then the processor determines whether the first relative value is less than the second relative value and whether the second relative value is less than the third relative value and selects at least one electrode from the fourth group of electrodes if the first relative value is less than the second relative value and the second relative value is less than the third relative value.

21. The system of claim 16, wherein, if the processor determines that the fourth relative value is greater than the first, second, and third relative values, and that at least one of the first relative value is not greater than the second relative value or the second relative value is not greater than the third relative value, and that at least one of the first relative value is not less than the second relative value or the second relative value is not less than the third relative value, then the processor determines whether the first relative value is greater than the third relative value and selects at least one electrode from the third or fourth group of electrodes if the first relative value is greater than the third relative value.

22. The system of claim 16, wherein, if the processor determines that the fourth relative value is less than the first, second, and third relative values, then the processor determines whether the fourth relative value substantially equals zero and selects at least one electrode from the second or third group of electrodes if the fourth relative value substantially equals zero.

23. The system of claim 16, wherein, if the processor determines that the fourth relative value is less than the first, second, and third relative values, then the processor determines whether the second relative value is greater than the third relative value and selects at least one electrode from the second group of electrodes if the second relative value is greater than the third relative value.

24. The system of claim 16, wherein, if the processor determines that the fourth relative value is less than the first, second, and third relative values, and that the fourth relative value does not equal zero, and that the second relative value is not greater than the third relative value, then the processor determines whether the third relative value is greater than the second relative value and selects at least one electrode from the third group of electrodes if the third relative value is greater than the second relative value.

25. The system of claim 16, wherein, if the processor determines that the second relative value is greater than the first, third, and fourth relative values, then the processor determines whether the first relative value is greater than the third relative value and selects at least one electrode from the second group of electrodes if the first relative value is greater than the third relative value.

26. The system of claim 16, wherein, if the processor determines that the second relative value is greater than the first, third, and fourth relative values, then the processor determines whether the first relative value is less than the third relative value and selects at least one electrode from the third group of electrodes if the first relative value is less than the third relative value.

27. The system of claim 16, wherein the first group of bioelectrical signals comprises a first bioelectrical signal and the first group of electrodes comprises a first electrode, the second group of bioelectrical signals comprises a second bioelectrical signal and the second group of electrodes comprises a second electrode, the third group of bioelectrical signals comprises a third bioelectrical signal and the third group of electrodes comprises a third electrode, and the fourth group of bioelectrical signals comprises a fourth bioelectrical signal and the fourth group of electrodes comprises a fourth electrode, and wherein, if the processor determines that the fourth relative value is greater than the first, second, and third relative values, then the processor at least one of:

determines whether the first relative value is greater than the second relative value and whether the second relative value is greater than the third relative value and selects the first electrode if the first relative value is greater than the second relative value and the second relative value is greater than the third relative value, determines whether the first relative value is less than the second relative value and whether the second relative value is less than the third relative value and selects the fourth electrode if the first relative value is less than the second relative value and the second relative value is less than the third relative value, determines whether at least one of the first relative value is not greater than the second relative value or the second relative value is not greater than the third relative value, and whether at least one of the first relative value is not less than the second relative value or the second relative value is not less than the third relative value, wherein the processor determines whether the first relative value is less than the third relative value if at least one of the first relative value is not greater than the second relative value or the second relative value is not greater than the third relative value, and at least one of the first relative value is not less than the second relative value or the second relative value is not less than the third relative value, and selects at least one of the first or second electrodes if the first relative value is less than the third relative value, or determines whether at least one of the first relative value is not greater than the second relative value or the second relative value is not greater than the third relative value, and whether at least one of the first relative value is not less than the second relative value or the second relative value is not less than the third relative value, wherein the processor determines whether the first relative value is greater than the third relative value if at least one of the first relative value is not greater than the second relative value or the second relative value is not greater than the third relative value, and at least one of the first relative value is not less than the second relative value or the second relative value is not less than the third relative value, and selects at least one of the third or fourth electrodes if the first relative value is greater than the third relative value.

28. The system of claim 16, wherein the first group of bioelectrical signals comprises a first bioelectrical signal and the first group of electrodes comprises a first electrode, the second group of bioelectrical signals comprises a second bioelectrical signal and the second group of electrodes comprises a second electrode, the third group of bioelectrical signals comprises a third bioelectrical signal and the third group of electrodes comprises a third electrode, and the fourth group of bioelectrical signals comprises a fourth bioelectrical signal and the fourth group of electrodes comprises a fourth electrode, and wherein if the processor determines that the fourth relative value is less than the first, second, and third relative values, then the processor at least one of:
- determines whether the fourth relative value substantially equals zero and selects at least one of the second or third electrodes if the fourth relative value substantially equals zero,
- determines whether the second relative value is greater than the third relative value and selects the second electrode if the second relative value is greater than the third relative value, or
- determines whether the fourth relative value does not equal zero, and that the second relative value is not greater than the third relative value, and determines whether the third relative value is greater than the second relative value if the fourth relative value does not equal zero and second relative value is not greater than the third relative value, and selects the third electrode if the third relative value is greater than the second relative value.

29. The system of claim 16, wherein the first group of bioelectrical signals comprises a first bioelectrical signal and the first group of electrodes comprises a first electrode, the second group of bioelectrical signals comprises a second bioelectrical signal and the second group of electrodes comprises a second electrode, the third group of bioelectrical signals comprises a third bioelectrical signal and the third group of electrodes comprises a third electrode, and the fourth group of bioelectrical signals comprises a fourth bioelectrical signal and the fourth group of electrodes comprises a fourth electrode, and wherein if the processor determines that the second relative value is greater than the first, third, and fourth relative values, then the processor determines whether the first relative value is greater than the third relative value and selects the second electrode if the first relative value is greater than the third relative value, or determines whether the first relative value is less than the third relative value and selects the third electrode if the first relative value is less than the third relative value.

30. The system of claim 16, wherein:
- the first group of bioelectrical signals comprises a first bioelectrical signal and the first group of electrodes comprises a first electrode,
- the second group of bioelectrical signals comprises a second bioelectrical signal, a third bioelectrical signal, and a fourth bioelectrical signal and the second group of electrodes comprises a second electrode, a third electrode, and a fourth electrode,
- the third group of bioelectrical signals comprises a fifth bioelectrical signal, a sixth bioelectrical signal, and a seventh bioelectrical signal and the third group of electrodes comprises a fifth electrode, a sixth electrode, and a seventh electrode, and
- the fourth group of bioelectrical signals comprises an eighth bioelectrical signal and the fourth group of electrodes comprises an eighth electrode.

31. The system of claim 30, wherein the processor determines the first relative value of the frequency domain characteristic based on the frequency domain characteristics for the first and second groups of bioelectrical signals by at least:
- determining a fifth relative value of the frequency domain characteristic based on the frequency domain characteristics for the first and second bioelectrical signals;
- determining a sixth relative value of the frequency domain characteristic based on the frequency domain characteristics for the first and third bioelectrical signals;
- determining a seventh relative value of the frequency domain characteristic based on the frequency domain characteristics for the first and fourth bioelectrical signals;
- determining a first average value based on the fifth, sixth, and seventh relative values, wherein the first relative value comprises the first average value, wherein the processor determines the second relative value of the frequency domain characteristic based on the frequency domain characteristics for the second and third groups of bioelectrical signals by at least:
- determining an eighth relative value of the frequency domain characteristic based on the frequency domain characteristics for the second and fifth bioelectrical signals;
- determining a ninth relative value of the frequency domain characteristic based on the frequency domain characteristics for the third and sixth bioelectrical signals;
- determining a tenth relative value of the frequency domain characteristic based on the frequency domain characteristics for the fourth and seventh bioelectrical signals; and
- determining a second average value based on the eighth, ninth, and tenth relative values, wherein the second relative value comprises the second average value, wherein the processor determines the third relative value of the frequency domain characteristic based on the frequency domain characteristics for the third and fourth groups of bioelectrical signals by at least:
- determining an eleventh relative value of the frequency domain characteristic based on the frequency domain characteristics for the fifth and eighth bioelectrical signals;
- determining a twelfth relative value of the frequency domain characteristic based on the frequency domain characteristics for the sixth and eighth bioelectrical signals;
- determining a thirteenth relative value of the frequency domain characteristic based on the frequency domain characteristics for the seventh and eighth bioelectrical signals; and
- determining a third average value based on the eleventh, twelfth, and thirteenth relative values, wherein the third relative value comprises the third average value, and wherein the processor determines the fourth relative value of the frequency domain characteristic based on the frequency domain characteristics for the first and fourth groups of bioelectrical signals by at least determining a fourteenth relative value of the frequency domain characteristic based on the frequency domain characteristics for the first and eighth bioelectrical signals, wherein the fourth relative value comprises the fourteenth relative value.

32. The system of claim 30, wherein if the processor determines that the fourth relative value is greater than the first, second, and third relative values, then the processor at least one of:

determines whether the first relative value is greater than the second relative value and whether the second relative value is greater than the third relative value and selects the first electrode if the first relative value is greater than the second relative value and the second relative value is greater than the third relative value, determines whether the first relative value is less than the second relative value, and determines whether the second relative value is less than the third relative value, and selects the eighth electrode if the first relative value is less than the second relative value and the second relative value is less than the third relative value, determines whether at least one of the first relative value is not greater than the second relative value or the second relative value is not greater than the third relative value, determines whether at least one of the first relative value is not less than the second relative value or the second relative value is not less than the third relative value, and if at least one of the first relative value is not greater than the second relative value or the second relative value is not greater than the third relative value, and at least one of the first relative value is not less than the second relative value or the second relative value is not less than the third relative value, the processor determines whether the first relative value is less than the third relative value, and selects at least one electrode from at least one of the first or second groups of electrodes if the first relative value is less than the third relative value, or determines whether at least one of the first relative value is not greater than the second relative value or the second relative value is not greater than the third relative value, and determines whether at least one of the first relative value is not less than the second relative value or the second relative value is not less than the third relative value, wherein the processor determines whether the first relative value is greater than the third relative value if at least one of the first relative value is not greater than the second relative value or the second relative value is not greater than the third relative value, and selects at least one electrode from the third group of electrodes or the eighth electrode if the first relative value is greater than the third relative value.

33. The system of claim 30, wherein if the processor determines that the fourth relative value is less than the first, second, and third relative values, then the processor at least one of:

determines whether the fourth relative value substantially equals zero, and selects at least one of the second electrode, the third electrode, the fourth electrode, the fifth electrode, the sixth electrode, or the seventh electrode if the fourth relative value substantially equals zero, determines whether the second relative value is greater than the third relative value and selects the second electrode if the second relative value is greater than the third relative value, or determines whether the fourth relative value does not equal zero, and that the second relative value is not greater than the third relative value, and determines whether the third relative value is greater than the second relative value if the fourth relative value does not equal zero and second relative value is not greater than the third relative value, and selects the third electrode if the third relative value is greater than the second relative value.

34. The system of claim 30, wherein, the processor determines whether the second relative value is greater than the first, third, and fourth relative values, and at least one of:

determines whether the first relative value is greater than the third relative value, and selects at least one electrode from the second group of electrodes if the first relative value is greater than the third relative value or determines whether the first relative value is less than the third relative value, and selects at least one electrode from the third group of electrodes if the first relative value is less than the third relative value.

35. The system of claim 30, wherein the processor selects at least one electrode from the second group of electrodes by at least:

determining a fifteenth relative value of the frequency characteristic based on the second and third bioelectrical signals;

determining a sixteenth relative value of the frequency characteristic based on the third and fourth bioelectrical signals;

determining a seventeenth relative value of the frequency characteristic based on the fourth and second bioelectrical signals; and selecting at least one of the second, third or fourth electrodes based on the fifteenth, sixteenth, and seventeenth relative values.

36. The system of claim 35, wherein the processor selects at least one of the second, third or fourth electrodes based on the fifteenth, sixteenth, and seventeenth relative values by at least:

determining whether the fifteenth relative value is substantially equal to the seventeenth relative value;

determining whether the sixteenth relative value is substantially equal to zero; and selecting the second electrode if the fifteenth relative value is substantially equal to the seventeenth relative value and the sixteenth relative value is substantially equal to zero.

37. The system of claim 35, wherein the processor selects at least one of the second, third or fourth electrodes based on the fifteenth, sixteenth, and seventeenth relative values by at least:

determining whether the fifteenth relative value is substantially equal to zero;

determining whether the sixteenth relative value is less than the seventeenth relative value; and selecting at least one of the second or third electrodes if the fifteenth relative value is substantially equal to zero and the sixteenth relative value is less than the seventeenth relative value.

38. The system of claim 30, wherein the processor selects at least one electrode from the third group of electrodes by at least:

determining an eighteenth relative value of the frequency characteristic based on the fifth and sixth bioelectrical signals;

determining a nineteenth relative value of the frequency characteristic based on the sixth and seventh bioelectrical signals;

determining a twentieth relative value of the frequency characteristic based on the seventh and fifth bioelectrical signals; and selecting at least one of the fifth, sixth, or seventh electrodes based on the eighteenth, nineteenth, and twentieth relative values.

39. The system of claim 38, wherein the processor selects at least one of the fifth, sixth, or seventh electrodes based on the eighteenth, nineteenth, and twentieth relative values by at least:

determining whether the eighteenth relative value is substantially equal to the twentieth relative value;
determining whether the nineteenth relative value is substantially equal to zero; and
selecting the sixth electrode if the eighteenth relative value is substantially equal to the twentieth relative value and the nineteenth relative value is substantially equal to zero.

40. The system of claim 38, wherein the processor selects at least one of the fifth, sixth, or seventh electrodes based on the eighteenth, nineteenth, and twentieth relative values by at least:
determining whether the eighteenth relative value is substantially equal to zero;
determining whether the nineteenth relative value is less than the twentieth relative value; and
selecting at least one of the fifth or sixth electrodes if the eighteenth relative value is substantially equal to zero and the nineteenth relative value is less than the twentieth relative value.

41. The system of claim 16, wherein:
the first group of bioelectrical signals comprises a first bioelectrical signal, a second bioelectrical signal, and a third bioelectrical signal and the first group of electrodes comprises a first electrode, a second electrode, and a third electrode,
the second group of bioelectrical signals comprises a fourth bioelectrical signal, a fifth bioelectrical signal, and a sixth bioelectrical signal and the second group of electrodes comprises a fourth electrode, a fifth electrode, and a sixth electrode,
the third group of bioelectrical signals comprises a seventh bioelectrical signal, an eighth bioelectrical signal, and a ninth bioelectrical signal and the third group of electrodes comprises a seventh electrode, an eighth electrode, and a ninth electrode, and
the fourth group of bioelectrical signals comprises a tenth bioelectrical signal, an eleventh bioelectrical signal, and a twelfth bioelectrical signal and the fourth group of electrodes comprises a tenth electrode, an eleventh electrode, and a twelfth electrode.

42. The system of claim 16, wherein the processor selects at least one electrode from at least one of the first, second, third, or fourth groups of electrodes for delivering stimulation to the target tissue site of the patient based on the first, second, third, and fourth relative values by at least selecting a first electrode and a second electrode, and wherein the processor determines that the target tissue site is located closer to the first electrode than the second electrode based on at least one of the first, second, third, and fourth relative values; and selects electrical stimulation parameter values based on determining that the target tissue site is located closer to the first electrode than the second electrode.

43. The system of claim 16, wherein the processor selects at least one electrode from at least one of the first, second, third, or fourth groups of electrodes for delivering stimulation to the target tissue site of the patient based on the first, second, third, and fourth relative values by at least selecting a first electrode and a second electrode, and wherein the first, second, third, and fourth group of bioelectrical brain signals comprises a first bioelectrical brain signal sensed via the first electrode and a second bioelectrical brain signal sensed via the second electrode, wherein the processor determines the frequency domain characteristic for each of the bioelectrical brain signals by at least determining a first frequency domain characteristic of the first bioelectrical brain signal and a second frequency domain characteristic of the second bioelectrical brain signal, and wherein the processor selects electrical stimulation parameter values to distribute delivery of electrical stimulation therapy between the first and second electrodes based on a ratio of the first and second frequency domain characteristics.

44. The system of claim 16, wherein the processor selects at least one electrode from at least one of the first, second, third, or fourth groups of electrodes for delivering stimulation to the target tissue site of the patient based on the first, second, third, and fourth relative values by at least selecting a first electrode and a second electrode, and wherein the processor selects electrical stimulation parameter values to unevenly distribute delivery of electrical stimulation therapy between the first and second electrodes.

45. The system of claim 16, wherein the first, second, third, and fourth group of bioelectrical brain signals comprises a first bioelectrical brain signal sensed via a first electrode of the plurality of electrodes and a second bioelectrical brain signal sensed via a second electrode of the plurality of electrodes, wherein the processor determines the frequency domain characteristic for each of the bioelectrical brain signals by at least determining a first frequency domain characteristic of the first bioelectrical brain signal and a second frequency domain characteristic of the second bioelectrical brain signal, and wherein the processor selects electrical stimulation parameter values to deliver a first portion of the electrical stimulation therapy via the first electrode and a second portion of the electrical stimulation therapy via the second electrode, wherein the first portion of the electrical stimulation is proportional to the first frequency domain characteristic, and wherein the second portion of the electrical stimulation is proportional to the second frequency domain characteristic.

46. The system of claim 16, wherein the processor ranks the first and second electrodes based on at least one of the first, second, third, and fourth relative values; and selects electrical stimulation parameter values for delivery of electrical stimulation therapy via the first and second electrodes based on the ranking.

47. The system of claim 46, wherein the processor determines that the first electrode is closer to the target tissue site than the second electrode based on at least one of the first, second, third, and fourth relative values and ranks the first and second electrodes by at least ranking the first electrode higher than the second electrode.

48. A system comprising:
means for sensing a plurality of bioelectrical brain signals, each of the plurality of bioelectrical brain signals being sensed via at least one respective electrode of a plurality of electrodes;
means for determining a frequency domain characteristic for each of the plurality of bioelectrical signals;
means for determining a plurality of relative values of the frequency domain characteristics, wherein each of the plurality of relative values is based on at least two of the frequency domain characteristics;
means for determining whether a first relative value of the plurality of relative values is greater than or less than at least one other relative value of the plurality of relative values;
means for determining whether a second relative value of the plurality of relative values is greater than or less than another relative value of the plurality of relative values, in response to the determination that the first relative value is greater than or less than the at least one other relative value;

means for determining whether a target tissue site is positioned between two electrodes of the plurality of electrodes based on the determination of whether the first relative value of the plurality of relative values is greater than or less than at least one other relative value and based on the determination of whether the second relative value is greater than or less than another relative value; and means for selecting at least one electrode of the plurality of electrodes for delivering stimulation to the patient based on the determination of whether the target tissue site is positioned between the two electrodes.

49. The system of claim 48, wherein the means for sensing a plurality of bioelectrical brain signals via at least one respective electrode of the plurality of electrodes comprises means for sensing the plurality of bioelectrical brain signals with a plurality of unipolar electrode combinations, and wherein the means for determining a plurality of relative values of the frequency domain characteristics comprises means for determining a magnitude of a difference in the frequency domain characteristics of at least two bioelectrical signals in order to determine the plurality of relative values of the frequency domain characteristic.

50. The system of claim 48, wherein the means for sensing a plurality of bioelectrical brain signals via respective electrodes comprises means for sensing the plurality of bioelectrical brain signals with a plurality of bipolar electrode combinations, and the frequency domain characteristic of each bioelectrical brain signal indicates the relative values.

51. The system of claim 48, wherein the bioelectrical signals comprise a first set of bioelectrical signals, wherein at least three electrodes of the plurality of electrodes comprise a common position along a longitudinal axis of a lead,
wherein the means for sensing a plurality of bioelectrical brain signals comprises means for sensing a second set of bioelectrical signals within the brain of the patient with at least one electrode of the at least three electrodes, and
wherein the means for selecting at least one of the plurality of electrodes for delivering stimulation to the patient comprises means for determining a frequency domain characteristic for each of the bioelectrical signals of the second set of bioelectrical signals and means for selecting one of the electrodes of the at least three electrodes for delivering stimulation to the patient based on the frequency domain characteristics of the bioelectrical signals of the second set of bioelectrical signals.

52. The system of claim 48, wherein the two electrodes of the plurality of electrodes comprise electrodes with which bioelectrical brain signals used to determine the second relative value were sensed, wherein the means for determining whether a target tissue site is positioned between two electrodes comprises means determining that the second relative value is the lowest relative value of the plurality of relative values.

53. The system of claim 48, wherein the two electrodes of the plurality of electrodes comprises a first electrode and a second electrode, wherein the means for determining whether the target tissue site is positioned between two electrodes comprises means for determining that the target tissue site is located closer to the first electrode than the second electrode, the system further comprising means for selecting electrical stimulation parameter values based on determining that the target tissue site is located closer to the first electrode than the second electrode.

54. The system of claim 53, wherein the means for selecting electrical stimulation parameter values comprises means for selecting electrical stimulation parameter values to unevenly distribute delivery of electrical stimulation therapy between the first and second electrodes.

55. A system comprising:
means for sensing a first group of bioelectrical signals in a brain of a patient via a first group of electrodes comprising at least one electrode from the plurality of electrodes, a second group of bioelectrical signals in the brain of the patient via a second group of electrodes comprising at least one electrode from the plurality of electrodes, a third group of bioelectrical signals in the brain of the patient via a third group of electrodes comprising at least one electrode from the plurality of electrodes, and a fourth group of bioelectrical signals in the brain of the patient via a fourth group of electrodes comprising at least one electrode from the plurality of electrodes;
means for determining a frequency domain characteristic for each of the bioelectrical signals within each of the first, second, third, and fourth groups of bioelectrical signals;
means for determining a first relative value of the frequency domain characteristic based on the frequency domain characteristics for the first and second groups of bioelectrical signals, a second relative value of the frequency domain characteristic based on the frequency domain characteristics for the second and third groups of bioelectrical signals, a third relative value of the frequency domain characteristic based on the frequency domain characteristics for the third and fourth groups of bioelectrical signals, a fourth relative value of the frequency domain characteristic based on the frequency domain characteristics for the first and fourth groups of bioelectrical signals;
means for determining whether the first relative value is less than the third relative value if the fourth relative value is greater than the first, second, and third relative values, and if at least one of the first relative value is not greater than the second relative value or the second relative value is not greater than the third relative value, and if at least one of the first relative value is not less than the second relative value or the second relative value is not less than the third relative value; and
means for selecting an electrode from at least one of the first, second, third, or fourth groups of electrodes for delivering stimulation to a target tissue site of the patient based on the first, second, third, and fourth relative values, wherein the means for selecting selects the at least one electrode by selecting at least one electrode from at least one of the first or second groups of electrodes if the first relative value is less than the third relative value.

56. The system of claim 55, wherein the first, second, third, and fourth group of bioelectrical brain signals comprises a first bioelectrical brain signal sensed via a first electrode of the plurality of electrodes and a second bioelectrical brain signal sensed via a second electrode of the plurality of electrodes, wherein the means for determining a frequency domain characteristic comprises means for determining the frequency domain characteristic for each of the bioelectrical brain signals by at least determining a first frequency domain characteristic of the first bioelectrical brain signal and a second frequency domain characteristic of the second bioelectrical brain signal, the system further comprising means for selecting electrical stimulation parameter values to deliver a first portion of the electrical stimulation therapy via the first electrode and a second portion of the electrical stimulation therapy via the second electrode, wherein the first portion of the electrical stimulation is proportional to the first frequency domain characteristic, and wherein the second portion of the electrical stimulation is proportional to the second frequency domain characteristic.

57. The system of claim 55, further comprising:
   means for ranking the first and second electrodes based on at least one of the first, second, third, and fourth relative values; and
   means for selecting electrical stimulation parameter values for delivery of electrical stimulation therapy via the first and second electrodes based on the ranking.

58. A non-transitory computer-readable storage medium comprising instructions that cause a programmable processor to:
   determine a frequency domain characteristic for each bioelectrical signal of a plurality of bioelectrical signals sensed in a brain of a patient with at least one respective electrode of a plurality of electrodes;
   determine a plurality of relative values of the frequency domain characteristic, wherein each of the plurality of relative values is based on at least two of the frequency domain characteristics;
   determine whether a first relative value of the plurality of relative values is greater than or less than at least one other relative value of the plurality of relative values;
   in response to determining that the first relative value is greater than or less than the at least one other relative value, determine whether a second relative value of the plurality of relative values is greater than or less than another relative value of the plurality of relative values;
   determine whether a target tissue site is positioned between two electrodes of the plurality of electrodes based on the determination of whether the first relative value is greater than or less than at least one other relative value and based on the determination of whether the second relative value is greater than or less than another relative value; and
   select at least one electrode of the plurality of electrodes for delivering stimulation to the patient based on determining whether the target tissue site is positioned between the two electrodes.

59. The non-transitory computer-readable storage medium of claim 58, wherein the two electrodes of the plurality of electrodes comprise electrodes with which bioelectrical brain signals used to determine the second relative value were sensed, the computer-readable storage medium further comprising instructions that cause the programmable processor to:
   determine that the second relative value is the lowest relative value of the plurality of relative values; and
   determine whether a target tissue site is positioned between the two electrodes based on determining that the second relative value is the lowest relative value of the plurality of relative values.

60. The non-transitory computer-readable storage medium of claim 58, wherein the two electrodes of the plurality of electrodes comprises a first electrode and a second electrode, the computer-readable storage medium further comprising instructions that cause the programmable processor to:
   determine that the target tissue site is located closer to the first electrode than the second electrode; and
   select electrical stimulation parameter values based on determining that the target tissue site is located closer to the first electrode than the second electrode.

61. The non-transitory computer-readable storage medium of claim 60, further comprising instructions that cause the programmable processor to select the electrical stimulation parameter values by at least selecting electrical stimulation parameter values to unevenly distribute delivery of electrical stimulation therapy between the first and second electrodes.

62. A non-transitory computer-readable storage medium comprising instructions that cause a programmable processor to:
   determine a frequency domain characteristic for each bioelectrical brain signal of a first group of bioelectrical signals in a brain of a patient with a first group of electrodes, a second group of bioelectrical signals in the brain of the patient with a second group of electrodes, a third group of bioelectrical signals in the brain of the patient with a third group of electrodes, and a fourth group of bioelectrical signals in the brain of the patient with a fourth group of electrodes;
   determine a first relative value of the frequency domain characteristic based on the frequency domain characteristics for the first and second groups of bioelectrical signals;
   determine a second relative value of the frequency domain characteristic based on the frequency domain characteristics for the second and third groups of bioelectrical signals;
   determine a third relative value of the frequency domain characteristic based on the frequency domain characteristics for the third and fourth groups of bioelectrical signals;
   determine a fourth relative value of the frequency domain characteristic based on the frequency domain characteristics for the first and fourth groups of bioelectrical signals;
   if the fourth relative value is greater than the first, second, and third relative values, and if at least one of the first relative value is not greater than the second relative value or the second relative value is not greater than the third relative value, and if at least one of the first relative value is not less than the second relative value or the second relative value is not less than the third relative value, then determine whether the first relative value is less than the third relative value; and
   select at least one electrode from the first, second, third, or fourth groups of electrodes for delivering stimulation to a target tissue site of the patient based on the first, second, third, and fourth relative values, wherein selecting the at least one electrode comprises selecting the at least one electrode from at least one of the first or second groups of electrodes if the first relative value is less than the third relative value.

63. The non-transitory computer-readable storage medium of claim 62, wherein the first, second, third, and fourth group of bioelectrical brain signals comprises a first bioelectrical brain signal sensed via a first electrode of the plurality of electrodes and a second bioelectrical brain signal sensed via a second electrode of the plurality of electrodes, the computer-readable storage medium further comprising instructions that cause the programmable processor to:
   determine the frequency domain characteristic for each of the bioelectrical brain signals by at least determining a first frequency domain characteristic of the first bioelectrical brain signal and a second frequency domain characteristic of the second bioelectrical brain signal; and
   select electrical stimulation parameter values to deliver a first portion of the electrical stimulation therapy via the first electrode and a second portion of the electrical stimulation therapy via the second electrode, wherein the first portion of the electrical stimulation is proportional to the first frequency domain characteristic, and wherein the second portion of the electrical stimulation is proportional to the second frequency domain characteristic.

64. The non-transitory computer-readable storage medium of claim 62, further comprising instructions that cause the programmable processor to:
rank the first and second electrodes based on at least one of the first, second, third, and fourth relative values; and
select electrical stimulation parameter values for delivery of electrical stimulation therapy via the first and second electrodes based on the ranking.

65. A system comprising:
a plurality of electrodes;
a sensing module that senses a plurality of bioelectrical brain signals via at least one electrode of the plurality of electrodes; and
a processor that determines a frequency domain characteristic for each of the plurality of bioelectrical signals; determines a plurality of relative values of the frequency domain characteristic, wherein each of the plurality of relative values is based on at least two of the frequency domain characteristics; determines that a first relative value of the plurality of relative values is less than a second relative value of the plurality of relative values, wherein the first relative value is based on frequency domain characteristics of a first pair of bioelectrical brain signals sensed by a first pair of electrodes, and wherein the second relative value is based on frequency domain characteristics of a second pair of bioelectrical brain signals sensed by a second pair of electrodes; and selects at least one electrode of the first pair of electrodes for delivering stimulation to the patient based on determining that the first relative value is less than the second relative value.

66. A system comprising:
means for determining a frequency domain characteristic for each bioelectrical brain signal of a plurality of bioelectrical signals sensed in a brain of a patient with a respective electrode;
means for determining a plurality of relative values of the frequency domain characteristic, wherein each of the plurality of relative values is based on at least two of the frequency domain characteristics;
means for determining that a first relative value of the plurality of relative values is less than a second relative value of the plurality of relative values, wherein the first relative value is based on frequency domain characteristics of a first pair of bioelectrical brain signals sensed by a first pair of electrodes, and wherein the second relative value is based on frequency domain characteristics of a second pair of bioelectrical brain signals sensed by a second pair of electrodes; and
means for selecting at least one electrode of the first pair of electrodes for delivering stimulation to the patient based on determining that the first relative value is less than the second relative value.

67. A non-transitory computer-readable storage medium comprising instructions that cause a programmable processor to:
determine a frequency domain characteristic for each bioelectrical brain signal of a plurality of bioelectrical signals sensed in a brain of a patient with a respective electrode;
determine a plurality of relative values of the frequency domain characteristic, wherein each of the plurality of relative values is based on at least two of the frequency domain characteristics;
determine that a first relative value of the plurality of relative values is less than a second relative value of the plurality of relative values, wherein the first relative value is based on frequency domain characteristics of a first pair of bioelectrical brain signals sensed by a first pair of electrodes, and wherein the second relative value is based on frequency domain characteristics of a second pair of bioelectrical brain signals sensed by a second pair of electrodes; and
select at least one electrode of the first pair of electrodes for delivering stimulation to the patient based on determining that the first relative value is less than the second relative value.

* * * * *